United States Patent [19]

Cronan, Jr.

[11] Patent Number: 5,252,466
[45] Date of Patent: Oct. 12, 1993

[54] FUSION PROTEINS HAVING A SITE FOR IN VIVO POST-TRANSLATION MODIFICATION AND METHODS OF MAKING AND PURIFYING THEM

[75] Inventor: John E. Cronan, Jr., Urbana, Ill.

[73] Assignees: Biotechnology Research and Development Corporation, Peoria; Board Of Trustees Of The University Of Illinois, Champaign, both of Ill.

[21] Appl. No.: 525,568

[22] Filed: May 18, 1990

Related U.S. Application Data

[63] Continuation-in-part of Ser. No. 354,266, May 19, 1989, abandoned.

[51] Int. Cl.⁵ .................... C12N 15/62; C12N 15/63
[52] U.S. Cl. .................... 435/69.7; 435/252.3; 435/320.1; 530/350
[58] Field of Search ............ 435/69.7, 252.3, 320.1; 530/350; 536/27

[56] References Cited

U.S. PATENT DOCUMENTS

| | | | |
|---|---|---|---|
| 4,366,246 | 12/1982 | Riggs | 435/69.8 |
| 4,546,082 | 10/1985 | Kurjan et al. | 435/172.3 |
| 4,582,810 | 4/1986 | Rosenstein | 436/528 |
| 4,588,684 | 5/1986 | Brake | 435/69.4 |
| 4,613,572 | 9/1986 | MacKay et al. | 435/252.33 |
| 4,704,362 | 11/1987 | Itakura et al. | 435/252.3 |
| 4,769,326 | 9/1988 | Rutter | 435/69.7 |
| 4,782,137 | 11/1988 | Hopp et al. | 530/328 |
| 4,839,293 | 6/1989 | Cantor et al. | 435/320 |
| 4,870,008 | 9/1989 | Brake | 435/69.4 |

FOREIGN PATENT DOCUMENTS

WO/86/02077  4/1986  PCT Int'l Appl.
WO/87/01391  3/1987  PCT Int'l Appl.
WO/87/05026  8/1987  PCT Int'l Appl.

OTHER PUBLICATIONS

P.N.A.S. 82:5617–5621, Sep. 1985, Murtif et al. Cloning and Expression of the 1.35 Biotin-Containing Subunit of Transcorboxylase.
Drucker et al., *J. Biol. Chem.*, 261, 9637–9643 (1986).
Sato et al., *Chem. Abstracts*, 111, 200 (abstract 226534z) (1989).
Berger et al., *The Journal of Biological Chemistry*, vol. 250, No. 3, pp. 927–933, Feb. 10, 1975.
Hoffman, et al., *Nucleic Acids Research*, vol. 15, No. 9, p. 3928 (1987).

(List continued on next page.)

*Primary Examiner*—Robert J. Hill, Jr.
*Assistant Examiner*—John D. Ulm
*Attorney, Agent, or Firm*—Willian Brinks Olds Hofer Gilson & Lione

[57] ABSTRACT

A hybrid DNA sequence encoding a fusion protein comprising: a first DNA sequence which encodes an amino acid sequence that allows for post-translation modification of the fusion protein; and a second DNA sequence joined end to end with the first DNA sequence and in the same reading frame, the second DNA sequence encoding a selected protein or polypeptide. Also, a vector comprising this hybrid DNA sequence, a host transformed with the vector, and a method of producing the fusion protein comprising culturing the transformed host under conditions permitting expression of the fusion protein. Further, a fusion protein comprising a selected protein or polypeptide and an amino acid sequence that allows for post-translation modification of the fusion protein. Finally, a method of isolating the modified fusion protein from a mixture of materials comprising: providing a binding partner that binds to the fusion protein only after it has been modified; contacting the modified fusion protein with the binding partner under conditions permitting binding; separating the modified fusion protein bound to the binding partner from the unbound materials in the mixture; and eluting the modified fusion protein.

9 Claims, 33 Drawing Sheets

OTHER PUBLICATIONS

Maina, et al., *Gene*, vol. 74, pp. 365-373 (1988).
Matuda, et al., *Biochemical and Biophysical Research Communications*, vol. 142, No. 3, pp. 953-957, Feb. 13, 1987.
Murtif, et al., *The Journal of Biological Chemistry*, vol. 262, No. 24, pp. 11813-11816, Aug. 25, 1987.
Nilsson, et al., *The EMBO Journal*, vol. 4, No. 4, pp. 1075-1080 (1985).
Thekkumkara et al., Biochemical and Biophysical Research Communications, vol. 145, No. 2, pp. 903-907 (1987).
Ullmann, *Gene*, vol. 29, pp. 27-31 (1984).
Hannestad et al., *Analytical Chemistry*, 126, 200-204 (1982).
Guest et al., *Journal of Molecular Biology*, 185, 743-754 (1985).
Alexander, et al., *Gene*, 31, 79-89 (1984).
Bai et al., *Eur. J. Biochem.*, 182, 239 (1989).
Barker and Campbell, *J. Bacteriology*, 143, 789-800 (1988).
Barker and Campbell, *J. Mol. Biol.*, 146, 4679 (1981).
Beaty and Lane, *J. Biol. Chem.*, 257, 924-929 (1982).
Berg et al., *Proc. Natl. Acad. Sci. USA*, 72, 3628-32 (1975).
Botstein et al., *Gene*, 8, 17 (1979).
Bradford, Howell, Aitken, James and Yeaman, *Biochem. J.*, 245, 919-922 (1987).
Buckel, *Meth. Enzymol.*, 125, 547-558 (1986).
Buoncristrani & Otsuka, *J. Biol. Chem.*, 263, 1013 (1988).
Carroll and Laufhon, *DNA Cloning*, vol. 3, pp. 89-111 (Glover ed., IRL Press, Oxford, U.K. 1987).
Casadaban, Martinez-Arias, Shapira and Chou, *Methods Enz.*, 100, 293-308 (1983).
Chambers, Prior, Barstow and Minton, *Gene*, 68, 139-149 (1988).
Chandler and Ballard, *Biochem. J.*, 251, 749 (1988).
Coppel, McNeilage, Surh, VandeWater, Spithill, Whittingham and Gershwin, *Proc. Natl. Acad. Sci. USA*, 85, 7317-7321 (1988).
Cronan, Narasimhan, and Rawlings, *Gene*, 70, 161-169 (1988).
Dakshinamurti et al., *Ann. N.Y. Acad. Sci.*, 447, 38 (1985).
Dimroth, *Meth. Enzymol.*, 125, 530-540 (1986).
Eisenberg, *Ann. N.Y. Acad. Sci.*, 447, 335-49 (1984).
Fall, *Meth. Enzymology*, 62, 390-98 (1979).
Fellay, Frey and Krisch, *Gene*, 52, 147-154 (1987).
Fujiwara, Okamura-Ikeda and Motokawa, *J. Biol. Chem.*, 261, 8836-8841 (1986).
Gershwin, Mackay, Sturgess and Coppel, *J. Immunol.*, 138, 3525-3531 (1987).
Gravel et al., *Arch. Biochem. Biophys.*, 201, 669-673 (1980).
Green, *Adv. Protein Chem.*, 29, 85-113 (1975).
Gross, *Methods in Enzymology*, 11, 238-55 (1967).
Guest et al., *J. Mol. Biol.*, 185, 743-54 (1985).
Hanahan, *J. Mol. Biol.*, 166, 557 (1983).
Hanemaaijer, Janssen, Kok and Veeger, *Eur. J. Biochem.*, 174, 593-599 (1988).
Hannestad et al., *Analytical Biochemistry*, 126, 200 (1982).
Hendrikson et al., *Anal. Biochem.*, 94, 366 (1979).
Hendrikson et al., *Proc. Nat'l Acad. Sci. USA*, 86, 2190 (1989).
Herbert and Guest, *Methods in Enzymology*, 18, 269-272 (1970).
Hoffman et al., *Nucleic Acid Research*, 15, 3928 (1987).
Johnstone, R. M., "Sulfhydryl Agents: Arsenicals," in *Metabolic* Inhibitors, A Comprehensive Treatise, vol. II, pp. 99-118 (Academic Press, New York 1963).
Laussermair et al., *J. Biol. Chem.*, 264, 14710-15 (1989).
Lim et al., *Archives Biochem. and Biophys.*, 258, 259-64 (1987).
Lipinska, Zylicz, Georgopoulas, *J. Bacteriol.*, 172, 1791-1797 (1990).
McAllister and Coon, *J. Biol. Chem.*, 241, 2855 (1966).
Mead et al., *Prot. Engineer*, 1, 67 (1986).
Mishina et al., *Eur. J. Biochem.*, 111, 79 (1980).
Murtif, Bahler and Samols, *Proc. Natl. Acad. Sci. USA*, 82, 5617-21 (1985).
Murtif and Samols, *The Journal of Biological Chemistry*, 262, 11813-16 (1987).
Nagai and Thorgersen, *Methods in Enzymology*, 153, 461-79 (1987).
Nikolau et al., *Anal. Biochem.*, 149, 448-53 (1985).
Packman, Borges and Perham, *Biochem. J.*, 252, 79-86 (1988).
Radford et al., *J. Biol. Chem.*, 264, 767-75 (1989).
Robinson et al., *J. Biol. Chem.*, 258, 6660-64 (1983).
Rock and Cronan, *Meth. Enzyol.*, 71, 341 (1981).

OTHER PUBLICATIONS

Rogers and Lichstein, *J. Bacteriology*, 100, 556 (1989).
Ruther and Muller-Hill, *The EMBO Journal*, 2, 1791–94 (1983).
Samols et al., *J. Biol. Chem.*, 263, 6461–64 (1988).
Sano and Cantor, *Proc. Nat'l Acad. Sci. USA*, 87, 142–146 (1990).
Schwarz et al., *J. Biol. Chem.*, 263, 9640–45 (1988).
Shenoy, et al., *FASEB J.*, 2, 2505–2511 (1988).
Silhavy and Beckwith, *Microbiol. Rev.*, 49, 398–418 (1985).
Spencer, Darlison, Stephens, Duckenfield and Guest, *Eur. J. Biochem.*, 141, 361–374 (1984).
Stephens, Darlison, Lewis and Guest, *Eur. J. Biochem.*, 133, 155–62 (1983).
Strauch and Beckwith, *Proc. Nat'l Acad. Sci. USA*, 85, 1576–80 (1988).
Strauch, Johnson, Beckwith, *J. Bacteriol.*, 171, 2689–2697 (1989).
Struhl and Davis, *J. Mol. Biol.*, 136, 309–332 (1980).
Struhl, *Nature*, 300, 284–287 (1982).
Sutton et al., *J. Biol. Chem.*, 252, 3934–3940 (1977).
Suzuki, Nishimura, Yasuda, Nishimura, Yamada, and Hirota, *Molecular and General Genetics*, 167, 1–19 (1978).
Swack et al., *Anal. Biochem.*, 87, 115 (1978).
Takai et al., *J. Biol. Chem.*, 263, 2651 (1988).
Takeshita et al., *Gene*, 61, 63 (1987).
Ullman and Perrin, The Lactose Operon, (Beckwith and Zipser, eds. 1970, Cold Spring Harbor Laboratory, Cold Spring Harbor, New York).
Ullman, *Gene*, 29, 27–31 (1984).
Viera and Messing, *Gene*, 19, 219 (1982).
Weber et al., *Science*, 234, 85 (1989).
Wilcheck and Bayer, *Anal. Biochem.*, 171, 1, 1988.
Wood and Barden, *Ann. Rev. Biochem.*, 46, 385–413 (1977).
Yanisch-Perron et al., *Gene*, 33, 103–119 (1985).
Cronan, *Cell*, 58, 427–29 (1989).
di Guan et al., *Gene*, 67, 21–30 (1988).
Guest et al., *Biochem. Soc. Transactions*, 12, 220 (1984).
Packman et al., *The EMBO J.*, 3, 1315–19 (1984).
Packman et al., *Biochem. J.*, 217, 219–227 (1984).

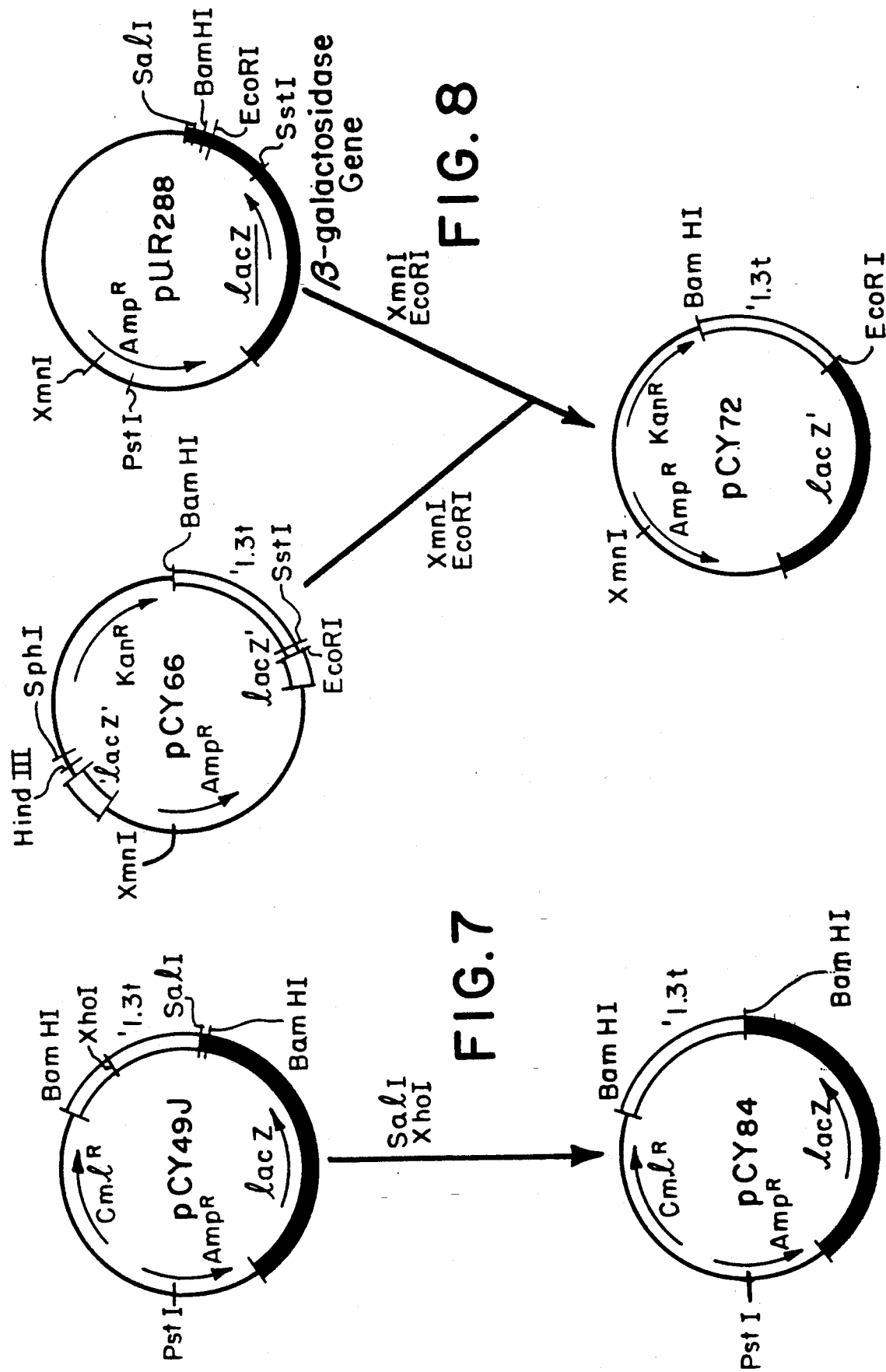

FIG.14

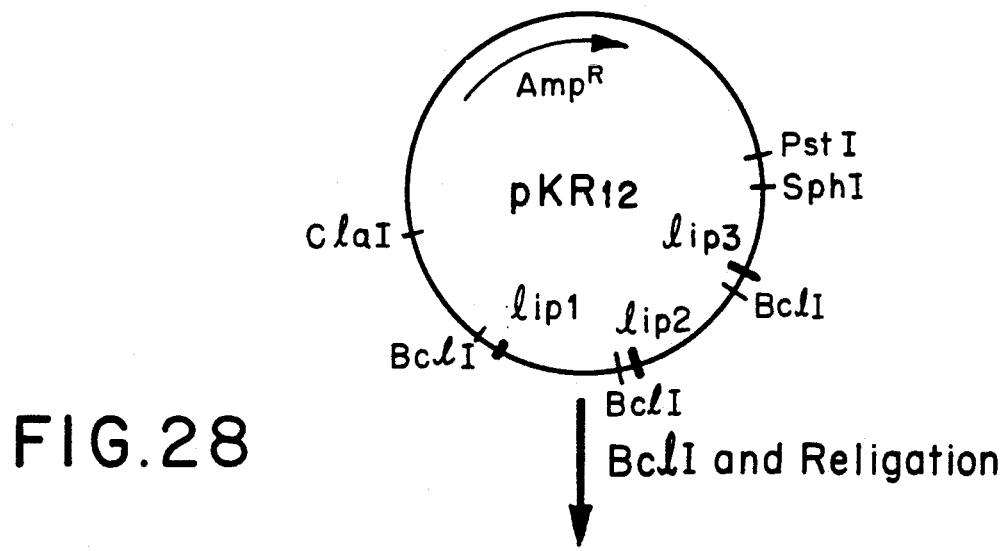
FIG.28
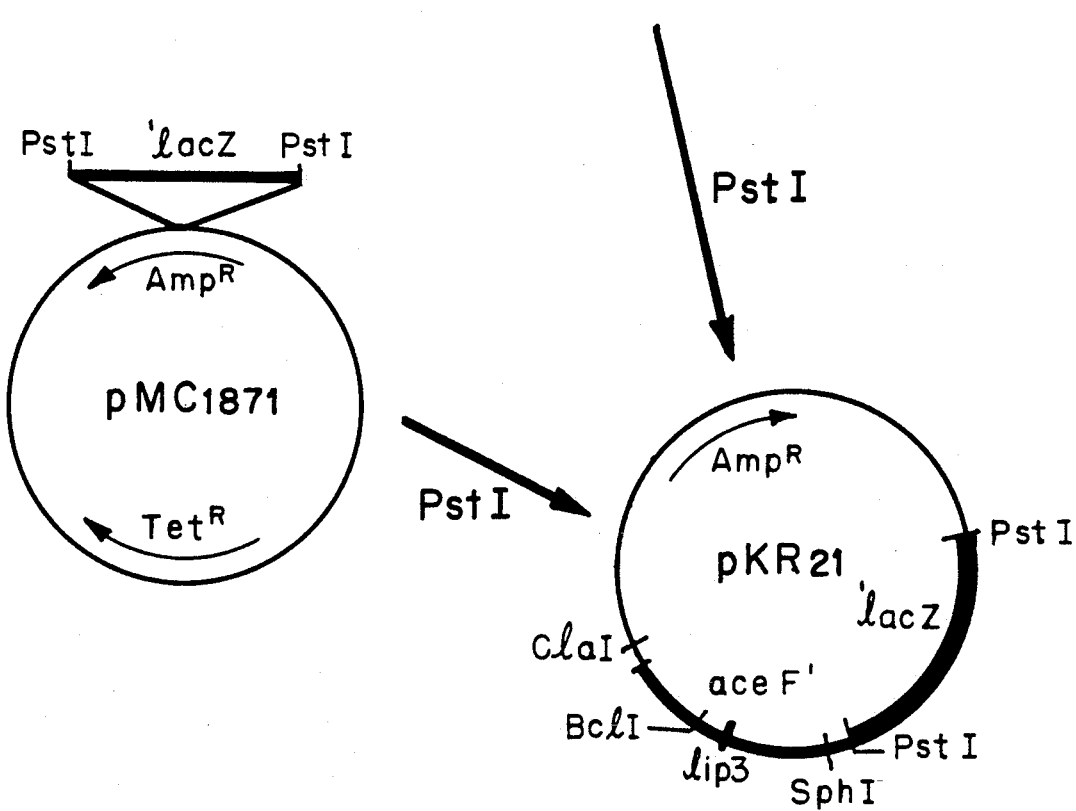

FIG. 31
KDa     1     2     3
200 —
97.4 —
68 —
43 —
29 —

FUSION PROTEINS HAVING A SITE FOR IN VIVO POST-TRANSLATION MODIFICATION AND METHODS OF MAKING AND PURIFYING THEM

The invention described herein was made in the course of work partially funded by Grant No. 2 RO1 AI15650 from the National Institutes of Health, U.S. Department of Health and Human Services. The U.S. government may have rights in this invention.

This application is a continuation-in-part of U.S. application Ser. No. 07/354,266, filed May 19, 1989, abandoned.

FIELD OF THE INVENTION

This invention relates to hybrid DNA sequences encoding fusion proteins comprising a protein or polypeptide of interest linked to an amino acid sequence which includes a post-translation modification site. The invention also relates to vectors containing the hybrid DNA sequences, to hosts transformed with these vectors and to the fusion proteins produced upon expression of the hybrid DNA in a suitable host. Finally, the invention comprises a method of purifying the fusion protein by utilizing binding partners that bind to the fusion protein only after it has been modified by the post-translation modification.

BACKGROUND OF THE INVENTION

Recent advances in molecular biology have made it possible to produce large amounts of heterologous proteins and polypeptides in bacterial, yeast, mammalian and other hosts. These processes rely on the construction of vectors comprising a DNA sequence coding for the desired protein or polypeptide operatively linked to expression control sequences. Suitable hosts are then transformed with these vectors to permit production of the desired product by fermentation under appropriate conditions. A further improvement of the above technology has made it possible to obtain secretion of the selected protein or polypeptide by forming a hybrid gene consisting of a DNA fragment which codes for the selected protein or polypeptide and a DNA sequence from an extracellular or periplasmic protein that is secreted.

To isolate the desired protein or polypeptide when it is not secreted from the host, the host cells must be disrupted and the protein or polypeptide isolated from other intracellular and extracellular proteins, cellular debris and other contaminants. Although a protein or polypeptide that is secreted is separated from intracellular proteins and cell debris, it must still be recovered from the culture medium or periplasmic space. Recovery of the desired protein or polypeptide in either situation generally involves a purification scheme that is time-consuming and less simple than desired. Such purification schemes also often result in loss of product or activity.

In particular, such purification schemes are generally empirical. For instance, when one of the various column separation techniques is used, all of the fractions must be assayed for the protein or polypeptide of interest. Also, many of the purification procedures are not specific, and a combination of methods must be used resulting in numerous steps. Activity and product may be lost due to the number of steps and time involved in such procedures.

One method utilized in purification schemes involves using recombinant DNA techniques to produce a fusion protein comprising the protein or polypeptide of interest linked to a reporter protein. Assay of the reporter protein is used to follow purification of the fusion protein or to provide a means of isolating the fusion protein.

Although numerous reporter proteins have been used, the paradigm of the method is fusion to $\beta$-galactosidase. Beta-galactosidase fusion proteins can be purified by conventional separation techniques based on charge, size, etc., with the progress of the separation being monitored by assaying for $\beta$-galactosidase activity, assaying for the ability of the fusion protein to complex with a second defective $\beta$-galactosidase resulting in $\beta$-galactosidase activity, or by the presence of $\beta$-galactosidase antigenic determinants by reaction with anti-$\beta$-galactosidase antibodies. Silhavy and Beckwith, *Microbiol. Rev.*, 49, 398-418 (1985); Ullman and Perrin, in *The Lactose Operon* (Beckwith and Zipser, eds., 1970, Cold Spring Harbor Laboratory, Cold Spring Harbor, N.Y.). Beta-galactosidase fusion proteins can also be purified on columns of immobilized anti-$\beta$-galactosidase antibodies or, if an active site is retained, on columns of an immobilized substrate analog. Silhavy and Beckwith, *Microbiol. Rev.*, 49, 398-418 (1985); Ullman, *Gene*, 29, 27-31 (1984).

Fusion to reporter proteins other than $\beta$-galactosidase often better facilitates purification since the reporter proteins can be chosen so that specific antibodies are not required. An example of such fusions are constructs in which the protein of interest is fused to protein A which binds to the Fc portion of IgG. Such fusions can be separated on columns of IgG. Nilsson et al., *The EMBO J.*, 4, 1075-80 (1985).

A complication of the methods for purification of the $\beta$-galactosidase and protein A fusion proteins using antibody, immunoglobulin or substrate columns is that harsh conditions are needed to disrupt the protein-protein or enzyme-substrate complexes retained on the purification columns. These conditions would be expected to at least partially denature the desired protein or polypeptide segment of the fusion protein. See Nilsson et al., *The EMBO J.*, 4, 1075-80 (1985); Ullman, *Gene*, 29, 27-31 (1984); Ullman and Perrin, in *The Lactose Operon* (Beckwith and Zipser, eds., 1970, Cold Spring Harbor Laboratory, Cold Spring Harbor, N.Y.).

Biotin is a small coenzyme (vitamin H) synthesized by plants, most bacteria and some fungi, which occurs primarily in a protein-bound state within the cell. Biotinated proteins play enzymatic roles in many essential metabolic carboxylation and decarboxylation reactions. Wood and Barden, *Ann. Rev. Biochem.*, 46, 385-413 (1977).

Biotin is bound to acceptor proteins by a covalent amide linkage between the biotin carboxyl group and a unique lysine amino group. Id. Biotin addition is a two-step reaction catalyzed by biotin ligase (also called biotin holoenzyme synthetase) (See FIG. 1). Biotin is first converted to biotinoyl-AMP which then reacts with the epsilon-amino group of the specific lysine residue of the acceptor protein to form biocytin. Biotination is a post-translation modification.

The sequences of the carboxyl terminal portions of biotin proteins from diverse biological sources show substantial homology, and biotin ligases will biotinate acceptor proteins from very different biological sources (e.g., bacteria versus higher eukaryotes). Murtif and Samols, *J. Biol. Chem.*, 262, 11813-16 (1987); Schwarz et al., *J. Biol. Chem.*, 263, 9640-45 (1988); McAllister and Coon, *J. Biol. Chem.*, 241, 2855 (1966). Of particular note in these sequences are: 1) the highly conserved tetrapeptide containing the biocytin, Samols et al., *J. Biol. Chem.*, 263, 6461-64 (1988); 2) the presence of a proline residue or short proline-rich region upstream of the biocytin, Id., Schwarz et al., *J. Biol. Chem.*, 263, 9640-45 (1988); and 3) the fact that the lysine residues of the proteins to which biotin binds are generally located 34 or 35 residues from the carboxyl terminal amino acid, although a few biotinated proteins have the coenzyme attached at sites farther away from the carboxyl terminus, Samols et al., *J. Biol. Chem.*, 263, 6461-64 (1988); Bai et al., *Eur. J. Biochem*, 182, 239 (1989); Takai et al., *J. Biol. Chem.*, 263, 2651 (1988).

FIG. 2 shows the amino acid sequences of the carboxyl terminal portions of several biotin proteins which have been compiled from published reports. The sequences are aligned at the lysine residue that becomes biotinated (arrow). The sequences shown are: *Escherichia coli* biotin carboxyl carrier protein (EC BCCP, a subunit of acetyl-CoA carboxylase); the 1.3S subunit of *Propionibacterium shermanii* transcarboxylase (PS 3S); *Saccharomyces cerevisiae* pyruvate carboxylase (YPYC); human pyruvate carboxylase (HPYC); and a sequence from tomato (TOM). The identity of the protein from tomato containing the biotination site is unknown. The segment was isolated by its biotin acceptor activity and homology to the *P. shermanii* sequence. Hoffman et al., *Nucleic Acid Research* 15, 3928 (1987).

In FIG. 2, the boxed residues are those residues which are conserved among the proteins. Additional comparisons of the sequences of biotinated proteins may be found in Samols et al., *J. Biol. Chem.*, 263, 6461-64 (1988) and Schwarz et al., *J. Biol. Chem.*, 263, 9640-45 (1988).

Studies have been made of the roles in biotination of certain sequences and amino acids located in the carboxyl terminal portions of biotin proteins. See Murtif and Samols, *J. Biol. Chem.*, 262, 11813-16 (1987); Samols et al., *J. Biol. Chem.*, 263, 6461-64 (1988). In particular, the 1.3S subunit of *Propionibacterium shermanii* transcarboxylase has been studied. It is 123 amino acids long. Biotin is attached to a lysine residue located 34 residues from the carboxyl terminus. A truncated 1.3S subunit polypeptide containing residues 19-123 is biotinated, while deletion of the penultimate amino acid (number 122) prevents biotination of the protein. Murtif and Samols, *J Biol. Chem.*, 262, 11813-16 (1987); Samols et al., *J. Biol. Chem.*, 263, 6461-64 (1988). Also, the methionine residues flanking the biocytin site are not necessary for biotination. Shenoy, et al., *FASEB J.*, 2, 2505-2511 (1988).

In addition to the covalent binding discussed above, biotin is non-covalently bound very tightly ($K_D 10^{-15}M$) and specifically by the proteins avidin and streptavidin. Streptavidin fusion proteins have been developed which exploit this non-covalent binding to biotin to purify the fusion protein. In particular, PCT applications WO 87/05026 and WO 86/02077 disclose that DNA sequences that code for streptavidin have been isolated, cloned and used to prepare recombinant DNA sequences coding for fusion proteins comprising a protein or polypeptide of interest fused to streptavidin. WO 86/02077 and WO 87/05026 further teach that the fusion protein may be isolated by contacting the fusion protein with biotin or a biotin derivative or analog. Other proteins or contaminants which do not bind to biotin can be washed away, and the fusion protein eluted from the biotin.

However, the conditions described in these applications for elution of the fusion protein from biotin or biotin derivatives are extremely harsh and would cause at least partial loss of activity and antigenic properties of the protein or polypeptide of interest. Also, streptavidin fusion proteins can be extremely lethal to the host cells producing them because of their binding to intracellular biotin and metabolically essential biotinated proteins. See Sano and Cantor, *Proc. Nat'l Acad. Sci. U.S.A.*, 87, 142-146 (1990).

Lipoylation is another post-translation modification. Lipoic acid is bound to acceptor proteins by means of a covalent amide linkage between the carboxyl group of the lipoic acid and an epsilon-amino group of a lysine residue of the protein. Stephens et al., *Eur. J. Biochem.*, 133, 481-89 (1983). This covalent attachment is catalyzed by the enzyme lipoate ligase.

The amino acid sequences of several lipoated proteins are known, and the amino acid sequences of the lipoylation sites of these proteins are substantially homologous throughout nature (see Table I below). It has also been shown that the lipoate ligase from one bacterium can lipoate the acceptor protein from unrelated bacteria both in vitro and in vivo.

TABLE I

COMPARISON OF AMINO ACID SEQUENCE OF VARIOUS LIPOYLATED PROTEINS

| Lipoylated Protein Source | Enzyme | | Sequence | Ref. |
|---|---|---|---|---|
| | | | + | |
| E. coli | E2p* | lip1 | LITVEGDKASMEVP | a |
| | | lip2 | LITVEGDKASMEVP | a |
| | | lip3 | LITVEGDKASMEVP | a |
| | E2o** | | LVEIETDKVVLEVP | b |
| B. stearo-thermophilus | E2p | | LCEVQNDKAVVEIP | c |
| A. vinelandii | E2p | lip1 | LVVLESAKASMEVP | d |
| | | lip2 | LIVLESDKASMEIP | d |
| | | lip3 | LIVLESDKASMEIP | d |
| | E2o | | LIVDLETDKVVMEVL | e |
| Bovine | E2p | | VETDKATVGF | f |
| Rat | E2p | | IETDKATIGFE | g |
| Human | E2p | lip1 | VETDKATVGFE | h |
| | | lip2 | IETDKATIGFE | h |
| Chicken | Glycine cleavage | | LESVKAASEL | i |

+ indicates lipoyl-lysine residue
*E2p = dihydrolipoamide acetyltransferase from pyruvate dehydrogenase
**E2o = dihydrolipoamide succinyltransferase from alpha-ketoglutarate dehydrogenase
a Stephens, Darlison, Lewis and Guest, Eur. J. Biochem., 133, 155-162 (1983).
b Spencer, Darlison, Stephens, Duckenfield and Guest, Eur. J. Biochem., 141, 361-374 (1984).
c Packman, Borges and Perham, Biochem. J., 252, 79-86 (1988).
d Hanemaaijer, Janssen, Kok and Veeger, Eur. J. Biochem. 174, 593-599 (1988).
e Westphal and Kok, Eur. J. Biochem., 187, 235-239 (1990).
f Bradford, Howell, Aitken, James and Yeaman, Biochem J., 245, 919-922 (1987).
g Gershwin, Mackay, Sturgess and Coppel, J. Immunol., 138, 3525-3531 (1987)
h Coppel, McNeilage, Surh, VandeWater, Spithill, Whittingham and Gershwin. Proc. Natl. Acad. Sci. USA, 85, 7317-7321 (1988).
i Fujiwara, Okamura-Ikeda and Motokawa, J. Biol. Chem., 261, 8836-8841 (1986)

The dihydrolipoamide acetyltransferase (E2p) component of the pyruvate dehydrogenase complex of *E. coli* contains three highly homologous sequences of about 100 amino acids each that are tandemly repeated to form the N-terminal half of the polypeptide chain. Id.; Guest et al., *J. Mol. Biol.*, 185, 743-54 (1985). All three of these sequences include a lysine that is a site for lipoylation, and the three sequences appear to form independently folded functional domains. Id. Each repeated sequence contains the lipoylation site in an invariant eighteen-residue sequence which is:

```
Ala — Glu — Gln — Ser — Leu — Ile — Thr —
Val — Glu — Gly — Asp — Lys (Lip) —
Ala — Ser — Met — Glu — Val — Pro.
```

Id.; Stephens et al., *Eur. J. Biochem.*, 133, 481–89 (1983). The three repeating sequences of E2p also contain lengthy C-terminal regions of about 20 to 30 amino acids that are unusually rich in alanine, proline and charged amino acids, and these regions provide conformational flexibility to the polypeptide. Radford et al., *J. Biol. Chem.*, 264, 767–75 (1989); Guest et al., *J. Mol. Biol.*, 185, 743–54 (1985).

SUMMARY OF THE INVENTION

The invention comprises novel fusion proteins. The fusion proteins are encoded by a hybrid DNA sequence comprising a first DNA sequence which encodes an amino acid sequence that allows for post-translation modification of the fusion protein, and a second DNA sequence joined end to end with the first DNA sequence and in the same reading frame, the second DNA sequence encoding a selected protein or polypeptide. The hybrid DNA sequence may further comprise a third DNA sequence that codes for a cleavage site that provides a means for cleaving the selected protein or polypeptide from the amino acid sequence that codes for the post-translation modification. The third DNA sequence is located between the first and second DNA sequences, and all three DNA sequences are in the same reading frame.

Preferred are hybrid DNA sequences wherein the first DNA sequence encodes an amino acid sequence that allows for post-translation biotination of the fusion protein, such as the amino acid sequence of the 1.3S subunit of *Propionibacterium shermanii* transcarboxylase, or fragments thereof that allow for post-translation biotination of the fusion protein. In particular, it has been found that a sequence that encodes the final 75 amino acids of the carboxyl terminus of the 1.3S subunit of *P. shermanii* transcarboxylase is biotinated, whereas a sequence that encodes the final 61 amino acids is not.

Also preferred are hybrid DNA sequences wherein the first DNA sequence encodes an amino acid sequence that allows for post-translation lipoylation of the fusion protein, such as the E2p subunit of the *E. coli* pyruvate dehydrogenase complex, or fragments thereof that allow for post-translation lipoylation of the fusion protein.

The invention also provides vectors comprising these hybrid DNA sequences and host cells transformed with the vectors. The vectors also preferably contain a DNA sequence coding for a signal or signal-leader sequence, or a fragment thereof, that provides for secretion of the fusion protein.

The invention also comprises a method of producing the fusion protein by culturing the transformed host under appropriate conditions to obtain expression of the fusion protein. Preferably the fusion protein is modified in vivo by the post-translation modification. Also, secretion of the fusion protein is obtained if a signal or signal-leader sequence is included.

The modified fusion protein may be purified from mixtures of materials such as cell extracts or the culture medium obtained upon culturing the transformed host by a method comprising: providing a binding partner that binds to the fusion protein only after it has been modified; contacting the modified fusion protein with the binding partner under conditions permitting binding; separating the modified fusion protein bound to the binding partner from the unbound materials in the mixture; and eluting the modified fusion protein. If the fusion protein contains a cleavage site, it may be cleaved while still bound to the binding partner or after being eluted from the binding partner.

The binding partner may be antibody or any compound which binds to the fusion protein only after it has been modified. For instance, when the fusion protein is a biotinated protein, the binding partner may be antibody to biotin, but is preferably selected from the group consisting of avidin, streptavidin, and derivatives and analogs thereof.

BRIEF DESCRIPTION OF THE DRAWINGS

FIG. 7: Illustrates the preparation of vector pCY84.

FIG. 8: Illustrates the preparation of vector pCY72.

FIG. 14: A typical fluorograph of biotinated fusion proteins and controls.

FIG. 28: Illustrates the preparation of vector pKR21.

FIG. 31: A fluorograph of lipoylated proteins prepared using a $^{35}$S-labeling procedure.

DETAILED DESCRIPTION OF THE PRESENTLY PREFERRED EMBODIMENTS

Figure 1:
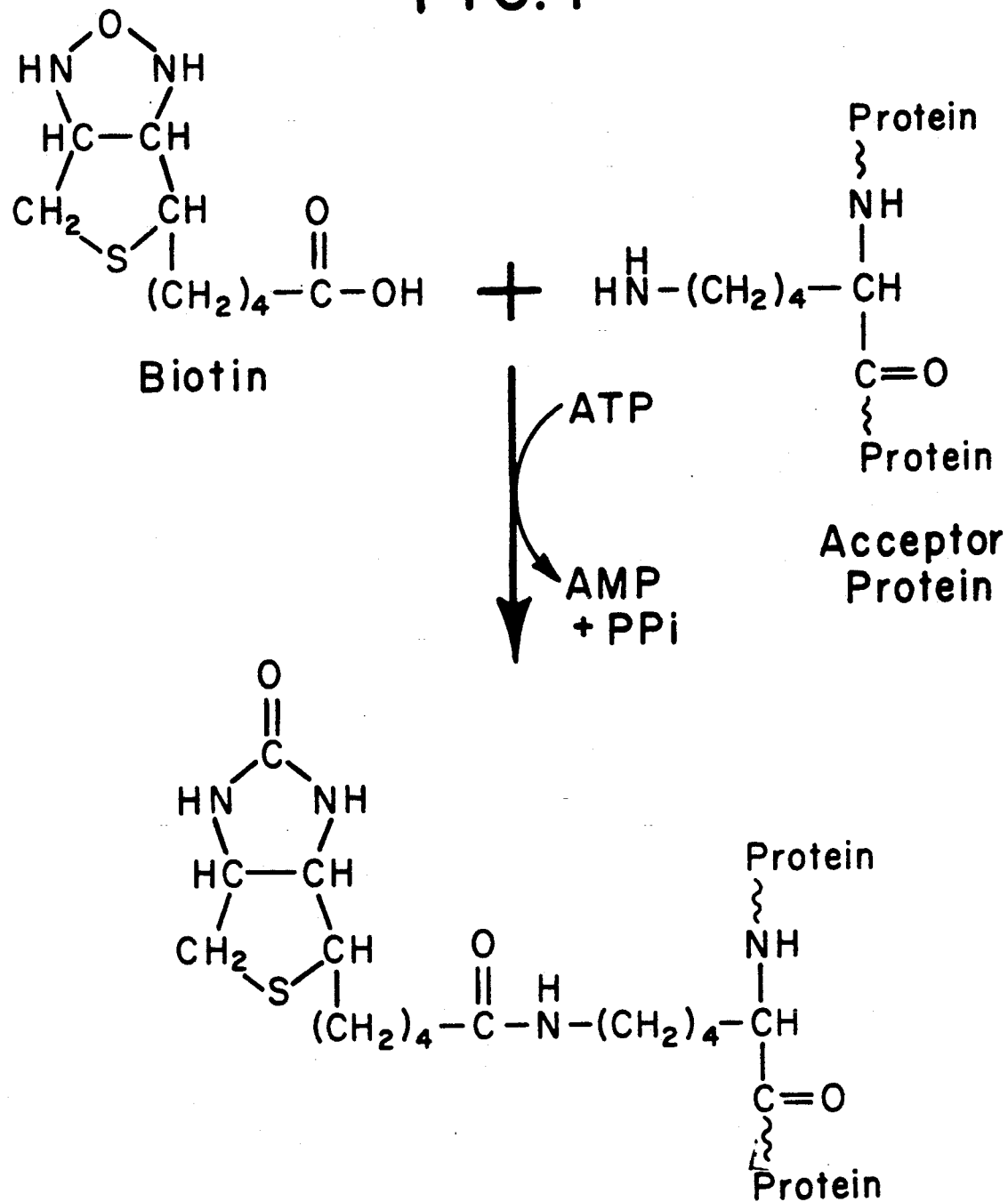
FIG. 1: Illustrates the addition of biotin to proteins by biotin ligase.

The hybrid DNA sequences of the invention comprise a first DNA sequence which encodes a site for post-translation modification. A post-translation modification is a modification that normally takes place within a cell whereby one or more chemical entities are covalently attached to an amino acid within the post-translation modification site by means of one or more enzymatic reactions. The site itself includes not only the amino acid that is modified, but any other amino acids, in the proper sequence, that are necessary to allow the post-translation modification to occur.

Although the term "post-translation" is used, the exact point during protein synthesis when such modifications occur is not yet known. Present evidence indicates that these modifications occur after the complete protein has been synthesized and released from the ribosome. For instance, Murtif and Samols have shown that the penultimate amino acid is essential to biotination (see Background section above). However, the possibility that the modifications occur, or are initiated, while protein synthesis is still occurring cannot be totally ruled out. As used herein, the term "post-translation" is intended to cover all of these possibilities.

The modification of the fusion protein preferably takes place in vivo by means of the reactions that normally occur within the host cell. When the modification is performed in vivo by the host cell, the fusion protein can be purified directly from a cell extract or from the cell culture medium using a binding partner that binds to the fusion protein only after the modification has taken place, as further described below.

However, where the modification of the fusion protein does not occur efficiently in the host cell, it may be necessary to modify in vitro that portion of the fusion proteins produced by the host cell that was not modified in vivo. The post-translation modification would be performed in vitro essentially the same as in vivo. The same post-translation modification site and enzymes recognizing this site would be used. For instance, a protein can be biotinated in vitro at the normal lysine residue using biotin ligases from many sources. The need to modify the fusion protein in vitro in this manner is expected to be very rare; it is expected that almost all fusion proteins will be modified efficiently in vivo.

The invention comprises any type of post-translation modification that provides a marker for the fusion protein that can be used, directly or indirectly, to identify the fusion protein or to isolate it from a mixture of other materials, including other proteins, such as those found in a cell extract or in medium in which the host cell has been cultured and which contains the fusion protein. The invention also comprises the use of two different post-translation modification sites on one fusion protein to further simplify purification.

Preferred are post-translation modifications that are utilized by the host cell to modify only a small number of proteins since this makes identification and isolation of the fusion protein easier. Examples of post-translation modifications utilized by cells to covalently modify only a few (one to five) proteins are biotination, attachment of 4-phosphopanthetheine, attachment of lipoic acid and attachment of flavins.

For example, E. coli has been shown to contain only one biotinated protein, the biotin carboxyl carrier protein (BCCP) component of acetyl-CoA carboxylase, two lipoated proteins and one protein that carries 4'-phosphopanthetheine. Fall, Meth. Enzymology, 62, 390 (1979); Perham et al., Biochem. Soc. Symp., 54, 67 (1987); Rock and Cronan, Meth. Enzymol., 71, 341 (1981). Other bacteria contain two or three biotinated proteins. Fall, Meth. Enzymol., 62, 390-98 (1979). Saccharomyces cerevisiae contains three to five biotinated proteins depending on growth conditions, whereas mammals and plants contain four such proteins. Chandler and Ballard, Biochem. J., 251, 749 (1988); Lim et al., Arch. Biochem. Biophys., 258, 219 (1987); Nikolau et al., Anal. Biochem., 149, 448-53 (1985); Robinson et al., J. Biol. Chem., 258, 6660-64 (1983). Also, all microorganisms, mammals and plants are believed to have at least two lipoated proteins (E2o and E2p) and probably three such proteins (the third protein being a lipoated protein involved in the glycine cleavage system).

The enzymology of the addition of biotin, 4-phosphopanthetheine and lipoic acid to proteins is understood, and all three of the modifications occur in virtually all cells. The sequences of proteins that are modified by these three compounds are known, and DNA sequences coding for post-translation modification sites can, therefore, be obtained using conventional methods such as preparing a cDNA or gDNA library which is screened for the correct sequences using hybridization probes. Indeed, the genes coding for some such proteins have already been cloned. Further, these modifications play roles in metabolism, so the modifying molecule is present on the surface of a modified protein, which aids in identification and purification of proteins carrying the modification.

All three modifying groups are also effective haptens, and antibodies specific to the modifying group can be prepared and used to purify the fusion proteins carrying the modification. Also, biotinated proteins can be identified and isolated easily by exploiting biotin's specific and strong affinity for avidin, streptavidin, and derivatives and analogs of those two compounds, all of which are relatively cheap and readily available as opposed to, for instance, antibodies to the biotinated protein. Similarly, lipoic acid is a dithiol which can be specifically and tightly bound by various metal compounds (e.g., arsenites and thallium compounds) that bind dithiols much more tightly than monothiols to provide a method of purifying fusion proteins modified with lipoic acid. The purification of the fusion proteins of the invention is discussed in greater detail below.

The DNA sequence coding for the post-translation modification site may be the sequence of a complete gene that codes for a protein which normally undergoes the post-translation modification of interest. It may also be a fragment of such a gene, provided the fragment codes for an amino acid sequence adequate to allow the post-translation modification to occur. Further, the DNA sequences of such genes or fragments may be varied, and totally synthetic sequences may be used, as long as a functional post-translation modification site is encoded.

The second DNA sequence of the hybrid DNA sequences of the invention codes for a selected protein or polypeptide of interest. The protein or polypeptide may be one that is normally made by the host (a "homologous" protein or polypeptide) or may be one that is not normally made by the host (a "heterologous" protein or polypeptide). In this manner, even a homologous protein or polypeptide may be tagged so that it can be identified or isolated by means of the post-translation modification.

Among the DNA sequences which are useful as the second DNA sequence are those which code for the following proteins or polypeptides: enzymes such as proteases and lipases; animal and human hormones such as human insulin, any of the various interferons, human growth hormone, bovine growth hormone, swine growth hormone, thyroid stimulating hormone, follicle stimulating hormone, vasopressin and prolactin; blood factors such as Factor VII, Factor VIII, erythropoietin and tissue plasminogen activator; lymphokines; globulins such as immunoglobulins; albumins; endorphins such as beta-endorphin and enkephalin; viral or bacterial antigens such as foot and mouth disease antigens, influenza antigenic protein and hepatitis core and surface antigens; rennin; *Bacillus thuringiensis* endotoxin; and other useful proteins and polypeptides of prokaryotic, eukaryotic or viral origin.

The hybrid DNA sequence coding for the fusion protein can be prepared and incorporated into a vector using conventional techniques known to those skilled in the art. First, the DNA sequences coding for the post-translation modification site and for the protein or polypeptide of interest are isolated. This may be accomplished by constructing a cDNA or gDNA library and screening for the DNA sequence of interest using appropriate hybridization probes. Of course, many genes and DNA sequences useful in the practice of the invention have already been isolated and cloned and are readily available. Further, many desired DNA sequences may be prepared by chemical synthesis if the DNA or amino acid sequence is known.

The hybrid DNA sequences of the invention are prepared by linking the DNA sequence coding for the post-translation modification site end to end to the DNA sequence coding for the protein or polypeptide of interest so that they are in the same reading frame. The DNA sequence coding for the post-translation modification site may be placed upstream or downstream from the DNA sequence coding for the protein or polypeptide of interest.

In a preferred embodiment, the hybrid DNA sequence also includes a third DNA sequence encoding a chemical or enzymatic cleavage site useful to separate the selected protein or polypeptide from the post-translation modification site. Such a cleavage site is built into the fusion protein by constructing the hybrid DNA sequence so that it has one or more codons that code for the desired cleavage site located between the DNA sequence encoding the post-translation modification site and the DNA sequence encoding the protein or polypeptide of interest, with all of the DNA sequences still in the same reading frame.

The cleavage site may be a site for proteolytic cleavage. Alternatively, where the selected protein or polypeptide of interest does not contain any methionine residues, the cleavage site may be methionine (encoded for by an ATG codon). The fusion protein may then be cleaved at the methionine residue by treatment with cyanogen bromide. Gross, *Methods in Enzymology*, 11, 238-55 (1967).

With respect to proteolytic cleavage sites, the cleavage site must be chosen so that cleavage does not occur in vivo or during purification due to proteases produced by the host cell. Also, the cleavage site is preferably unique enough so that it is present only on the fusion protein and not on other proteins produced by the host that are also modified by the post-translation modification. In this regard, the third DNA sequence can be designed so that it encodes a cleavage site recognized by a very specific protease such as Factor Xa which cleaves the peptide bond following ile-glu-gly-arg (Nagai and Thorgersen, *Methods in Enzymology*, 153, 461-79 (1987)), thrombin which cleaves fibrin, and elastase which cleaves elastin. It should be noted, however, that elastase from certain sources cleaves IgG, and the use of elastase may not be desirable where the fusion protein is isolated on an antibody column and cleavage on the column is desired.

The invention also includes a vector capable of expressing the fusion protein in an appropriate host. The vector comprises the hybrid DNA sequence that codes for the fusion protein operatively linked to appropriate expression control sequences. Methods of effecting this operative linking, either before or after the hybrid DNA sequence is inserted into the vector, are well known. Expression control sequences include promoters, activators, enhancers, operators, ribosomal binding sites, start signals, stop signals, cap signals, polyadenylation signals, and other signals involved with the control of transcription or translation.

The vector must contain a promoter and a transcription termination signal, both operatively linked to the hybrid DNA sequence. The promoter may be any DNA sequence that shows transcriptional activity in the host cell and may be derived from genes encoding homologous or heterologous proteins (preferably homologous) and either extracellular or intracellular proteins, such as amylases, glycoamylases, proteases, lipases, cellulases and glycolytic enzymes.

The promoter may be preceded by upstream activator and enhancer sequences. An operator sequence may also be included downstream of the promoter, if desired.

The vector should also have a translation start signal immediately preceding the hybrid DNA sequence, if the hybrid DNA sequence does not itself begin with such a start signal. There should be no stop signal between the start signal and the end of the hybrid DNA sequence.

Expression control sequences suitable for use in the invention are well known. They include those of the *E.coli* lac system, the *E.coli* trp system, the TAC system and the TRC system; the major operator and promotor regions of bacteriophage lambda; the control region of filamentaceous single-stranded DNA phages; the expression control sequences of other bacteria; promoters derived from genes coding for *Saccharomyces cerevisiae* TPI, ADH, PGK and alpha-factor; promoters derived from genes coding for *Aspergillus oryzae* TAKA amylase and *A. niger* glycoamylase, neutral alpha-amylase and acid stable alpha-amylase; promoters derived from genes coding for *Rhizomucor miehei* aspartic proteinase and lipase; and other sequences known to control the expression of genes of prokaryotic cells, eukaryotic cells, their viruses, or combinations thereof.

The vector must also contain one or more replication systems which allow it to replicate in the host cells. In particular, when the host is a yeast, the vector should contain the yeast 2u replication genes REP1-3 and origin of replication.

The vector should further include one or more restriction enzyme sites for inserting the hybrid DNA and other DNA sequences into the vector, and a DNA sequence coding for a selectable or identifiable phenotypic trait which is manifested when the vector is present in the host cell ("a selection marker").

Suitable vectors for use in the invention are well known. They include pUC (such as pUC8 and pUC4K), pBR (such as pBR322 and pBR328), pUR (such as pUR288), phage λ and YEp (such as YEp24) plasmids, other vectors described in the Examples below, and derivatives of of these vectors.

In a preferred embodiment, a DNA sequence encoding a signal or signal-leader sequence, or a functional fragment thereof, is included in the recombinant DNA vector between the translation start signal and the hybrid DNA sequence coding for the fusion protein. A signal or signal-leader sequence is a sequence of amino acids at the amino terminus of a polypeptide or protein which provides for secretion of the protein or polypeptide from the cell in which it is produced. Many such signal and signal-leader sequences are known.

By including a DNA sequence encoding a signal or signal-leader amino acid sequence in the vectors of the invention, the fusion protein encoded by the hybrid DNA sequence may be secreted from the cell in which it is produced. Preferably, the signal or signal-leader amino acid sequence is cleaved from the fusion protein during its secretion from the cell. If not, the fusion protein should preferably be cleaved from the signal or signal-leader amino acid sequence after isolation of the fusion protein.

Signal or signal-leader sequences suitable for use in the invention include *Saccharomyces cerevisiae* alpha factor (see U.S. Pat. Nos. 4,546,082 and 4,870,008), fragments of *S. cerevisiae* alpha factor, *S. cerevisiae* a factor (see U.S. Pat. No. 4,588,684), the yeast BAR1 secretion system (see U.S. Pat. No. 4,613,572), synthetic signal-leader sequences, *Kluyveromyces lactis* signal-leader sequence, and signal sequences which are normally part of precursors of proteins or polypeptides such as the precursor of interferon (see U.S. Pat. No. 4,775,622).

None of the known naturally-occurring proteins that are modified with biotin, 4-phosphopanthetheine or lipoic acid are secreted. This is to be expected since proteins modified by attachment of one of these three compounds are involved in cellular metabolism. Thus, including a signal or signal-leader sequence as part of the fusion protein is highly preferred when the post-translation modification involves the attachment of one of these three compounds to the fusion protein, since the only modified protein that would be secreted would be the fusion protein.

The resulting vector having the hybrid DNA sequence thereon is used to transform an appropriate host. This transformation may be performed using methods well known in the art.

Any of a large number of available and well-known host cells may be used in the practice of this invention. The host must be capable of performing the chosen post-translation modification. As pointed out above, almost all cells are capable of adding biotin, 4-phosphopanthetheine and lipoic acid to proteins.

The selection of a particular host is otherwise dependent upon a number of factors recognized by the art. These include, for example, compatibility with the chosen expression vector, toxicity to it of the fusion proteins encoded for by the hybrid DNA sequences, rate of transformation, ease of recovery of the fusion proteins, expression characteristics, biosafety and costs. A balance of these factors must be struck with the understanding that not all hosts may be equally effective for the expression of a particular hybrid DNA sequence or for the modification of the fusion protein by a particular post-translation modification.

Within these general guidelines, useful microbial hosts include bacteria (such as *E. coli* sp.), yeast (such as Saccharomyces sp.) and other fungi, insects, plants, mammalian (including human) cells in culture, or other hosts known in the art.

The host preferably is engineered so that none of its proteins other than the fusion protein is modified by the chosen post-translation modification. For instance, the proteins that are normally biotinated by yeast are not necessary for the growth of the yeast on certain supplemented media, and the genes that code for them can be deleted or otherwise rendered non-functional to create a yeast host that is capable of biotinating the fusion proteins of the invention, but which does not produce any other biotinated proteins. See Mishina et al., *Eur. J. Biochem.*, 111, 79 (1980). Similarly, the proteins that are normally lipoated by *E. coli* are not necessary for the growth of the bacteria on appropriately supplemented medium, and the genes that code for them can be deleted to create a bacterial host that can produce a lipoated fusion protein according to the invention as the only lipoated protein. Also, a temperature sensitive mutant *E. coli* strain has been developed which produces very little BCCP (the only biotinated protein normally produced by *E. coli*) when grown at high temperatures in the presence of fatty acids. This mutant strain, named fabE, is available from the Coli Genetic Stock Center, Yale University, New Haven, Conn.

The engineering of a suitable host must also take into consideration the possibility that the production of a fusion protein according to the invention could be harmful to cellular metabolism because of the decreased post-translation modification of endogenous proteins essential to cellular metabolism. For instance, toxicity could occur as a result of depletion of intracellular biotin, or because of the titration of the available biotin ligase activity, or both.

The potential problem of biotin depletion can be readily overcome by providing high concentrations of biotin in the growth medium. The biotin transport systems of *E. coli, Saccromyces cerevisiae* and mammalian tissue culture cells are able to transport biotin at sufficiently high rates to preclude biotin depletion. Barker & Campbell, *J. Bacteriology*, 143, 789 (1980); Rogers and Lichstein, *J. Bacteriology*, 100, 556 (1969); Dakshinamurti et al., *Ann. N.Y. Acad. Sci.*, 447, 38 (1985). There also is evidence that biotin at high concentrations can enter *E. coli* by diffusion. Barker & Campbell, *J. Bacteriology*, 143, 789 (1980).

Prolonged and high level expression of a biotinated fusion protein can result in deficient biotination of endogenous biotin proteins. In *E. coli*, the only endogenous biotinated protein is BCCP which catalyses an essential step in fatty acid synthesis. It has been found that high level expression of some fusion proteins according to the invention causes decreased biotination of BCCP, resulting in inhibition of the growth of the host cell (data not shown).

However, the gene (birA) encoding *E. coli* biotin ligase has been cloned, and multicopy plasmids carrying the birA gene are available. Barker & Campbell, *J. Mol. Biol.*, 146, 469 (1981); Buoncristrani & Otsuka, *J. Biol. Chem.*, 263, 1013 (1988). Such plasmids overproduce biotin ligase and can be used to overcome the possible growth inhibitory effects of fusion protein production, while increasing the yields of biotinated fusion proteins. In particular, Buoncristrani and Otsuka, *J. Biol. Chem.*, 263, 1013 (1988), reports that *E. coli* biotin ligase can be overproduced by >600-fold without deleterious effects on cellular growth. Using a similar plasmid, we have obtained quantitative biotination of very highly expressed (ca $3 \times 10^4$ molecules/cell) fusion proteins (see Example 8).

The *S. cerevisiae* ligase gene has not yet been cloned, although ligase-deficient mutants should allow cloning by genetic complementation. The *E. coli* ligase could be expressed in yeast or other heterologous systems to provide increased ligase levels. However, as noted above, the biotinated proteins in yeast are not necessary for the growth of the yeast, and the genes coding for them can be deleted or rendered non-functional.

To date, no problems with cellular metabolism have been noted in connection with the production of lipoylated proteins. Neither lipoic acid depletion nor titration of lipoate ligase seems to occur.

Next, the transformed host is cultured under conventional fermentation conditions so that the desired fusion protein is expressed. The fusion protein is also preferably modified in vivo by the post-translation modification.

The invention also includes a method of isolating the modified fusion protein from materials in a mixture comprising providing a binding partner that binds to the fusion protein only after it has been modified and contacting the modified fusion protein with the binding partner under conditions permitting binding. After the fusion protein is bound to the binding partner, the bound fusion protein is separated from other materials in the mixture (e.g., cell extract or culture medium), after which the fusion protein is eluted from the binding partner.

The post-translation modification site may be removed from the selected protein or polypeptide while the fusion protein is still bound to the binding partner or after it has been eluted. The post-translation modification site may be removed by a variety of means, but is preferably removed by means of the cleavage site described above.

The binding partner may be antibody. For instance, antibodies to biotin, to 4-phosphopanthetheine or to lipoic acid may be used to purify fusion proteins modified by attachment of these compounds. The antibody is preferably immobilized on a solid support. Methods of making and using antibodies to purify proteins are well known.

The binding partner may also be other compounds that bind to the fusion protein after it has been modified. As mentioned earlier, biotin is non-covalently bound very tightly ($K_D 10^{-15}$M) and specifically by avidin and streptavidin. This specific binding extends to biotin covalently linked to proteins in the manner discussed above, although with some decrease in the binding affinity ($K_D$ ca $10^{-11}$) due to steric hinderance. Thus, biotinated fusion proteins may be purified using avidin, streptavidin, or analogs or derivatives of these latter two compounds, as the binding partner. Analogs and derivatives of avidin and streptavidin include: subunits and fragments of avidin and streptavidin; avidin and streptavidin (whether full-size, subunit or fragment) having amino acid deletions, additions or substitutions; and chemically modified avidin and streptavidin. Any such analog or derivative is suitable as long as it retains the ability to specifically bind biotin.

The use of columns of immobilized avidin or streptavidin or their analogs or derivatives is the preferred means of purifying the biotinated fusion proteins of the invention since the risk of denaturation sometimes encountered using antibody columns is avoided. Such columns are also cheaper to use than are antibody columns. Further, avidin and streptavidin are more resistant to proteolysis and denaturation than antibodies, and the column life of avidin and streptavidin columns is longer than that of antibody columns.

Avidin and streptavidin columns can be prepared in same manner as other affinity columns such as antibody columns, and these methods are well known. For instance, avidin or streptavidin can be covalently coupled to Sepharose which has been activated with cyanogen bromide.

In a preferred embodiment of the method of the invention, a cell extract or culture medium containing a biotinated fusion protein having a cleavage site is passed over a column of immobilized avidin or streptavidin. Only the biotinated fusion protein and other biotinated proteins in the extract or medium are retained on the column. The fusion protein is then cleaved at the cleavage site so that the protein or polypeptide of interest may be eluted from the column, while the polypeptide containing the biotination site is retained on the column. If the cleavage site is chosen so that it is not present elsewhere on the fusion protein or on any of the other biotinated proteins, only the selected protein or polypeptide of interest will be eluted from the column. Although avidin and streptavidin are generally resistant to proteases, the cleavage site is also preferably not one found on avidin or streptavidin.

Although columns using avidin and streptavidin of normal affinity are preferred when cleaving the fusion protein on the column because they seem to withstand these procedures better, the extremely tight binding of the biotin moiety by avidin and streptavidin can be a disadvantage if elution of the complete biotinated fusion protein is desired. Binding of biotinated proteins by avidin and streptavidin is essentially irreversible by competition with free biotin, and extremely harsh procedures which cause denaturation of the biotinated proteins must be used to elute them from such columns.

However, avidin columns with decreased affinity for biotin and biotinated proteins can be readily and reproducibly prepared by conversion of avidin from its normal quaternary form to a monomeric form. Such monomer avidin columns are obtained by treatment of columns of immobilized avidin with guanidine solutions. This treatment partially and irreversibly denatures the avidin and converts most of the high affinity biotin binding sites to sites of lower affinity ($K_D$ ca $10^{-6}$ to $10^{-7}$M). The remaining high affinity sites can be blocked with biotin giving columns from which bound biotinated proteins can be quantitatively eluted with biotin-containing non-denaturing buffers.

References describing the preparation and properties of low affinity monomer avidin columns include: Green, *Adv. Protein Chem.*, 29, 85–133 (1975); Kohanski and Lane, *Ann. N. Y. Acad. Sci.*, 447, 373–385 (1984); Beaty and Lane, *J. Biol. Chem.*, 247, 924–929 (1982); Henrickson et al., *Anal. Biochem.*, 94, 366–370 (1979); Gravel et al., *Arch. Biochem. Biophys.*, 201, 669–673 (1980); Dimroth, *Meth. Enzymol.*, 125, 530–540 (1986); Buckel, *Meth. Enzymol.*, 125, 547–558 (1986); Shenoy et al., *FASEB J.*, 2, 2505–2511 (1988). These references also describe how to prepare avidin columns of normal affinity either expressly (see, e.g., Kohanski and Lane, *Ann. N. Y. Acad. Sci.*, 447, 373–385 (1984)), or indirectly since the preparation of materials suitable for use in such columns is an initial step in the preparation of the low affinity monomer avidin columns.

When a cell extract or cell culture medium is passed over a low affinity monomer avidin column, only the biotinated fusion protein and other biotinated proteins are bound. The bound biotinated proteins are eluted using a biotin-containing buffer. In this manner, the fusion protein will be eluted without being denatured, and the column may be reused.

The fusion protein may be separated from any other biotinated proteins and the biotin in the elution buffer by conventional separation procedures such as separations based on size, charge or antigenicity. Alternatively, the fusion protein may be cleaved at the cleavage site if one is present, and the mixture of proteins and biotin passed over an avidin or streptavidin (normal high affinity) column to which the other biotinated proteins and the biotin will bind. Again, if the cleavage site is unique to the junction between the segments of the fusion protein, only the selected protein or polypeptide of interest will be eluted from this column.

It should also be possible to prepare streptavidin columns of lower affinity. As noted in the Background section, the streptavidin gene has been cloned. Also, the crystal structure has recently been solved, and a low resolution avidin structure is essentially superimposable on the streptavidin structure. Weber et al., *Science*, 234, 85 (1989); Hendrickson et al., *Proc. Nat'l Acad. Sci. U.S.A.*, 86, 2190 (1989); W. A. Hendrickson, personal communication. These structures account for the decreased biotin binding affinity of monomeric avidin. In tetrameric avidin, one of the four tryptophan residues forming the hydrophobic biotin binding site of a given subunit is derived from a neighboring (cydad-related) subunit, and monomerization removes this residue from the biotin binding site, giving a lower affinity. Thus, appropriate expression of the streptavidin gene coupled with site-directed mutagensis guided by the crystal structure should produce tetrameric streptavidin molecules with the affinity of the monomer (or in principle any given affinity). Such tetrameric molecules should be more stable than monomers to proteases and denaturants and should provide a superior column-bound ligand.

The lipoyl residue on a lipoated protein contains an intramolecular disulfide bond. When the lipoated protein is reduced, the lipoyl residue forms dithiol dihydrolipoic acid, and lipoated fusion proteins may be purified using metal compounds that bind such dithiols much more tightly than monothiols.

The lipoated fusion proteins may be reduced with agents that reduce disulfide bonds to yield dithiols. Such agents and methods of using them are well known. Suitable reducing agents include borohydride, monothiols such as mercaptoethanol and thioglycollate, and 1,4-dithiols such as dithiothreitol. The 1,4-dithiols are preferred.

Organoarsenites bind dithiols much more tightly than monothiols if the thiol moieties are on adjacent carbon atoms or on carbon atoms separated by a methylene residue (e.g., a 1,2-dithiol or a 1,3-dithiol). Dihydrolipoic acid is 6,8-dithiol, and tight binding to organoarsenites is essentially unique to this compound in biological systems, making organoarsenites a preferred choice for use in purifying lipoated fusion proteins according to the invention.

Suitable organoarsenites have the formula: $RAs=O$, wherein $As=O$ is the arsenite radical (arsine oxide) and R is any organic radical including unsubstituted or unsubstituted straight-chain, branched or cyclic (including aromatic) hydrocarbon radicals and heteroatom radicals. R is preferably a higher molecular weight ($>75$) radical since such organoarsenites are less volatile than lower molecular weight compounds. The organoarsenites may be prepared as described in J. L. Webb, *Enzyme and Metabolic Inhibitors*, Vol. III, pp. 595–793 (Academic Press, New York 1966) and R. M. Johnstone, "Sulfhydryl Agents: Arsenicals," in *Metabolic Inhibitors, A Comprehensive Treatise*, Vol. II, pp. 99–118 (Academic Press, New York 1963).

The organoarsenites may be coupled to polymeric materials to form organoarsenite columns. In such a case, R must also comprise a functional ligand, such as $NH_2$, SH and COOH, for coupling the $RAs=O$ to the polymeric material. Methods of making such columns and polymeric materials suitable for use in the columns are those employed for making other affinity columns and are well known.

Columns of organoarsenites bound to agarose may be prepared as described in Hannestad et al., *Analytical Biochemistry*, 126, 200 (1982). When a cell extract or cell culture medium is reduced and then passed over such a column, only the lipoated fusion protein and other lipoated proteins will be bound. The bound lipoated proteins can be eluted from the columns using sodium hydroxide or 1,2- or 1,3-dithiols such as dithiopropylamine, dihydrolipoic acid, 2,3-dimercapto-2-propanol or 2,3-dimercapto-2-propane sulfonic acid. In this manner, the fusion protein will be eluted without being denatured, and the column may be reused.

The fusion protein may be separated from any other lipoated proteins in the elution buffer by conventional separation procedures such as separations based on size, charge or antigenicity. Alternatively, the fusion protein may be cleaved at the cleavage site if one is present, and the mixture of proteins passed over another organoarsenite column to which will bind the other lipoated proteins and the lipoated polypeptide cleaved from the fusion protein. If the cleavage site is chosen so that it is not present elsewhere on the fusion protein or on any of the other lipoated proteins, only the selected protein or polypeptide of interest will be eluted from the column.

Alternatively, while the lipoated fusion protein is still bound to the organoarsenite column, the fusion protein may be cleaved at the cleavage site, if one is present, so that the protein or polypeptide of interest may be eluted from the column while the polypeptide containing the lipoylation site is retained on the column. Again, if the cleavage site is unique to the junction between the segments of the fusion protein, only the selected protein or polypeptide of interest will be eluted from this column.

The use of organoarsenite columns is the preferred means of purifying the lipoated fusion proteins of the invention since the risk of denaturation sometimes encountered using antibody columns is avoided. Such columns are also cheaper to use than are antibody columns (about 100 to 1000 times less expensive). Further, organoarsenites are insensitive to proteolysis and denaturation unlike antibodies, and the column life of organoarsenite columns is much longer than that of antibody columns.

Finally, for certain proteins (e.g., insoluble proteins such as membrane proteins) or under certain circumstances (e.g., proteins produced by recombinant DNA techniques sometimes form aggregates), it may be necessary to use denaturing agents (e.g., detergent or strongly chaotrophic agents) to solubilize the fusion protein so that it can be isolated. Antibody columns often cannot be used in these situations.

However, normal affinity avidin and streptavidin may be used to isolate biotinated fusion proteins in such cases since avidin and streptavidin retain their biotin binding capacity in the presence of denaturants. See Swack et al., *Anal. Biochem.*, 87, 114 (1978) which teaches that biotinated proteins present in crude mixtures of proteins solubilized with sodium dodecyl sulfate (SDS) can be quantitatively bound to columns of avidin immobilized on agarose, washed free of contaminating proteins, and eluted by boiling the column matrix in SDS. We have used a variation of this technique which utilizes streptavidin bound to agarose by an eleven-carbon arm to purify biotinated proteins to homogeneity.

Similarly, organoarsenite columns and the lipoate moiety are unaffected by protein denaturants, and such columns may be used to purify fusion proteins when denaturing conditions must be used. Indeed, the organoarsenite columns are even more resistant to such denaturants than the avidin and streptavidin columns since the organoarsenites are not proteins like avidin and streptavidin. Further, organoarsenite columns are cheaper and more stable than are avidin and streptavidin columns. Thus, the use of lipoylation and organoarsenite columns is generally preferred when denaturing conditions must be employed in the purification of a fusion protein and may be desirable from an economic point of view for other applications.

However, there are other considerations in deciding whether to use the lipoylation system or the biotination system. First, the organoarsenites are toxic and, if they contaminate the fusion protein product (which seems unlikely since the organoarsenite is covalently bound to the column), the organoarsenite would have to be removed by dialysis which would add another purification step. Second, binding of biotin by avidin and streptavidin may be more specific than is the binding of dihydrolipoic acid to organoarsenites. Third, the agents used to reduce the lipoated proteins, and the dithiols used to elute them, may inactivate some proteins by reducing intra- or interchain disulfide bonds. This disadvantage is likely to be protein specific since many proteins lack disulfide bonds and such bonds, if present, are generally buried within the protein where reducing agents would be unable to penetrate. If inactivation due to reduction of disulfide bonds occurs, it is generally reversible, but another step would be added to the purification protocol.

EXAMPLES

The restriction and other enzymes used in the following examples were obtained from Bethesda Research Laboratories, New England Biolabs or Boehringer Mannheim Biochemicals. Phage T4 DNA ligase was used for all ligations and recircularizations. The buffers and reaction conditions used when employing these enzymes were those recommended by the supplier.

EXAMPLE 1

Preparation and Expression of DNA Sequences Encoding Fusion Proteins Having a Site For Post-Translation Biotination Hybrid DNA sequences were prepared comprising: 1) DNA sequences encoding fragments of the 1.3S subunit of *Propionibacterium shermanii* transcarboxylase that contain the sequence encoding the biotin attachment site; and 2) all or part of the β-galactosidase structural gene. The two DNA sequences were fused so that a fusion protein was encoded having β-galactosidase or β-galactosidase fragments at the amino terminal end and having the biotin-acceptor sequences located at the carboxyl terminal end. These hybrid DNA sequences, on suitable vectors were used to transform appropriate hosts. When cultured under conditions permitting expression, biotinated fusion proteins were produced.

A. Preparation of Vectors Comprising Hybrid DNA Sequences Coding for Beta-Galactosidase And Fragments of the 1.3S Subunit The amino acid sequence of the 1.3S subunit of *P. Shermanii* transcarboxylase is known, and the gene coding for it has been cloned and sequenced. Murtif, Bahler and Samols, *Proc. Natl. Acad. Sci. U.S.A.*, 82, 5617-21 (1985). The carboxyl terminus contains sequences involved in the post-translation addition of biotin to the subunit. Murtif and Samols, *The Journal of Biological Chemistry*, 262, 11813-16 (1987).

The gene coding for the 1.3S subunit contains a number of naturally occurring restriction sites in the DNA sequences lying upstream of the biocytin lysine codon. See Murtif, Bahler and Samols, *Proc. Natl. Acad. Sci. U.S.A.*, 82, 5617-21 (1985). These sites were used to construct a series of β-galactosidase fusions with various lengths of the carboxyl terminal of the 1.3S subunit.

The starting material for preparing these constructs was plasmid ptac1.3t containing the structural gene coding for the 1.3S subunit. This plasmid was obtained from V. Murtif and D. Samols, Department of Biochemistry, Case Western Reserve University, Cleveland, Ohio 44106.

Alternatively, plasmid ptac1.3t may be prepared by the following procedure, most of the steps of which are described in Murtif, Bahler and Samols, *Proc. Natl. Acad. Sci. U.S.A.*, 82, 5617-21 (1985) and Murtif and Samols, *The Journal of Biological Chemistry*, 262, 11813-16 (1987), the disclosures of which are incorporated herein by reference. First, a genomic minilibrary was prepared by digesting to completion with PstI the genomic DNA extracted from anaerobically grown *P. shermanii*, strain W52. This strain is available from American Type Culture Collection (ATCC), Rockville Maryland, accession number 6207.

The purified PstI fragments were inserted into the PstI site of pUC9 (available from the ATCC, accession number 3725), and the resulting plasmid was used to transform *Escherichia coli* HB101 (available from the ATCC, accession number 33694). Positive colonies were identified using labeled hybridization probes, and a plasmid pTCl.3 containing a 1.7-kb PstI fragment containing the gene coding for the 1.3S subunit in the PstI site of pUC9 was isolated.

Plasmid pTCl.3t was constructed from plasmid pTCl.3 as follows. Plasmid pTCl.3 was cut with PstI and SfaNI to obtain a shortened fragment coding for the 1.3S subunit. The SfaNI end of this fragment was made blunt with T4 DNA polymerase, and the fragment was inserted into the PstI and SmaI sites of pUC9. The shortened insert of plasmid pTCl.3t is 0.4 kilobase in length and consists of sequences coding for the 123 residues of the 1.3S subunit in addition to 40 base pairs of 5'-flanking sequence and 30 base pairs of 3'-flanking sequence.

In plasmid ptacl.3t, the 0.4 kilobase insert of pTCl.3t is located adjacent to the tac promoter of the expression vector pKK223-3 (available from Pharmacia LKB Biotechnology, Pistcataway, N.J.). Plasmid ptacl.3t was prepared by cutting plasmid pTCl.3t with HindIII and EcoRI. The ends were filled in with T4 DNA polymerase, and the resulting fragment was ligated into the SmaI site of plasmid pKK223-3 to form plasmid ptacl.3t.

Further description of the details of the procedures and of the properties and sources of the various materials used may be found in the Murtif and Samols and Murtif, Bahler and Samols articles cited above.

Figure 21:
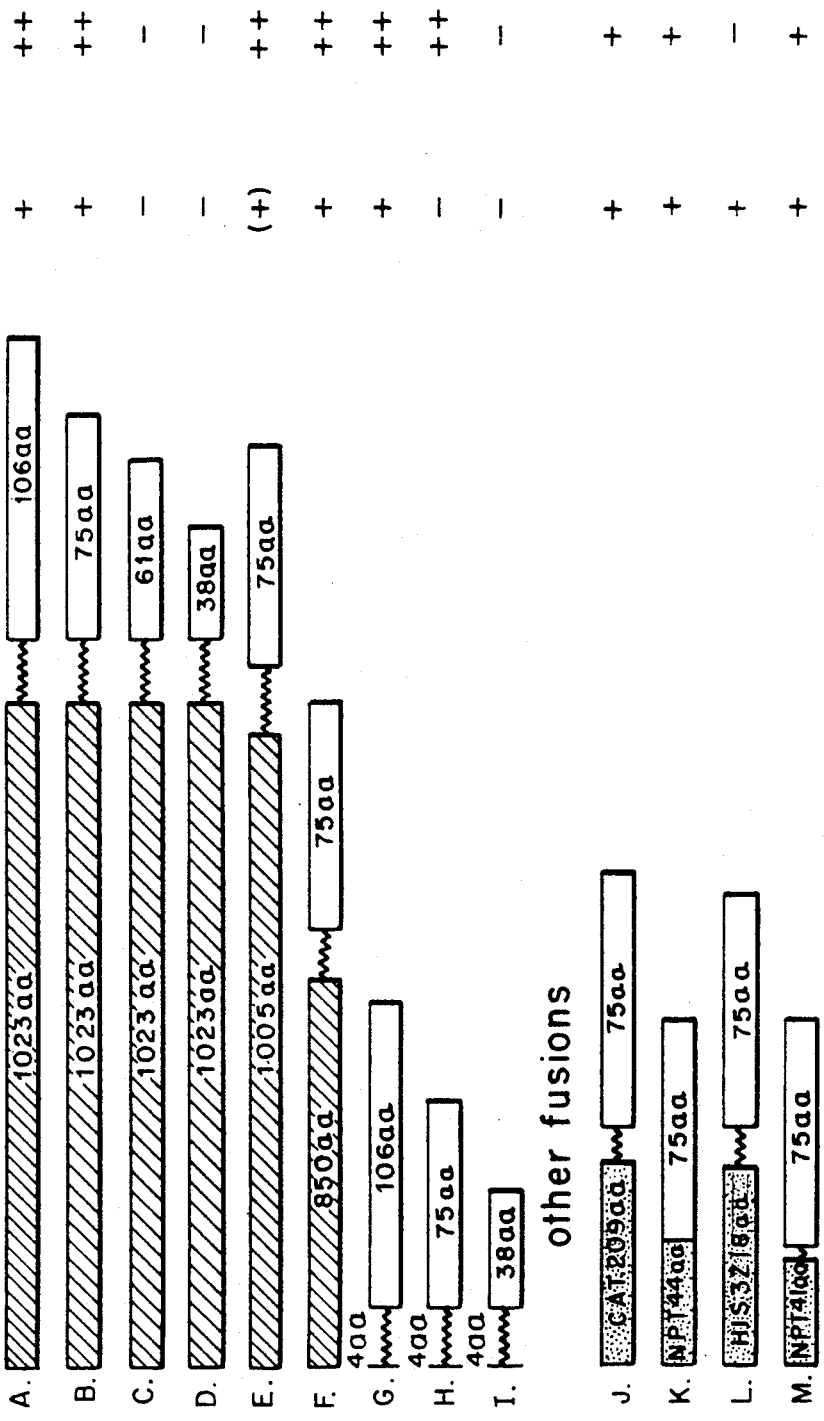
FIG. 21: Illustrates Fusions A-M and presents the results of culturing *E. coli* strains transformed with these fusions.

At the bottom of FIG. 21, the amino acid sequences coded for by the fragments of the 1.3S gene used in the hybrid DNA constructs are given. The four fragments used code for the carboxyl terminal 106 amino acids, the carboxyl terminal 75 amino acids, the carboxyl terminal 61 amino acids, and the carboxyl terminal 38 amino acids of the 1.3S subunit. These fragments were derived by cutting the 1.3S subunit structural gene in plasmid ptacl.3t with restriction enzymes SalI, NarI, NaeI, and XhoI, respectively, as further described below.

In addition to the fragments coding for these portions of the 1.3S subunit, the hybrid DNA sequences contained one of the following: 1) all of the β-galactosidase coding sequence, which on expression yields an active enzyme; 2) a DNA sequence encoding all of β-galactosidase except the last sixteen amino acids (an inactive enzyme); 3) a DNA sequence encoding the amino terminal 65% of the protein (an inactive enzyme); or 4) a DNA sequence encoding just the four amino terminal amino acids of the protein (also an inactive enzyme).

1. Preparation of Fusion A

Fusion A is a hybrid DNA sequence comprising the entire coding sequence of the beta-galactosidase gene linked in proper reading frame to a DNA sequence encoding the carboxyl terminal 106 amino acids of the 1.3S subunit. See FIG. 21.

Figure 3:
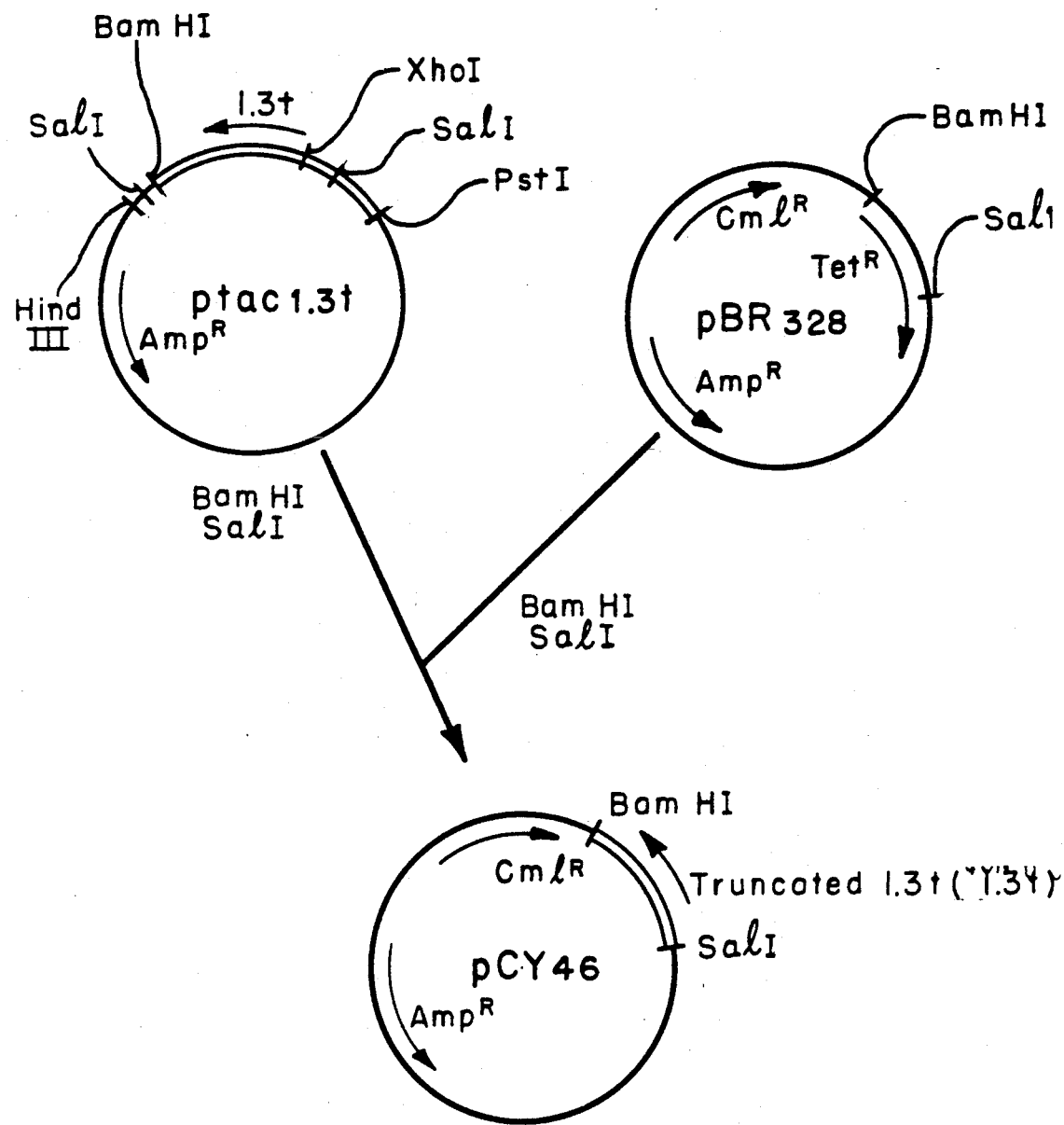
FIG. 3: Illustrates the preparation of vector pCY46.
Figure 4:
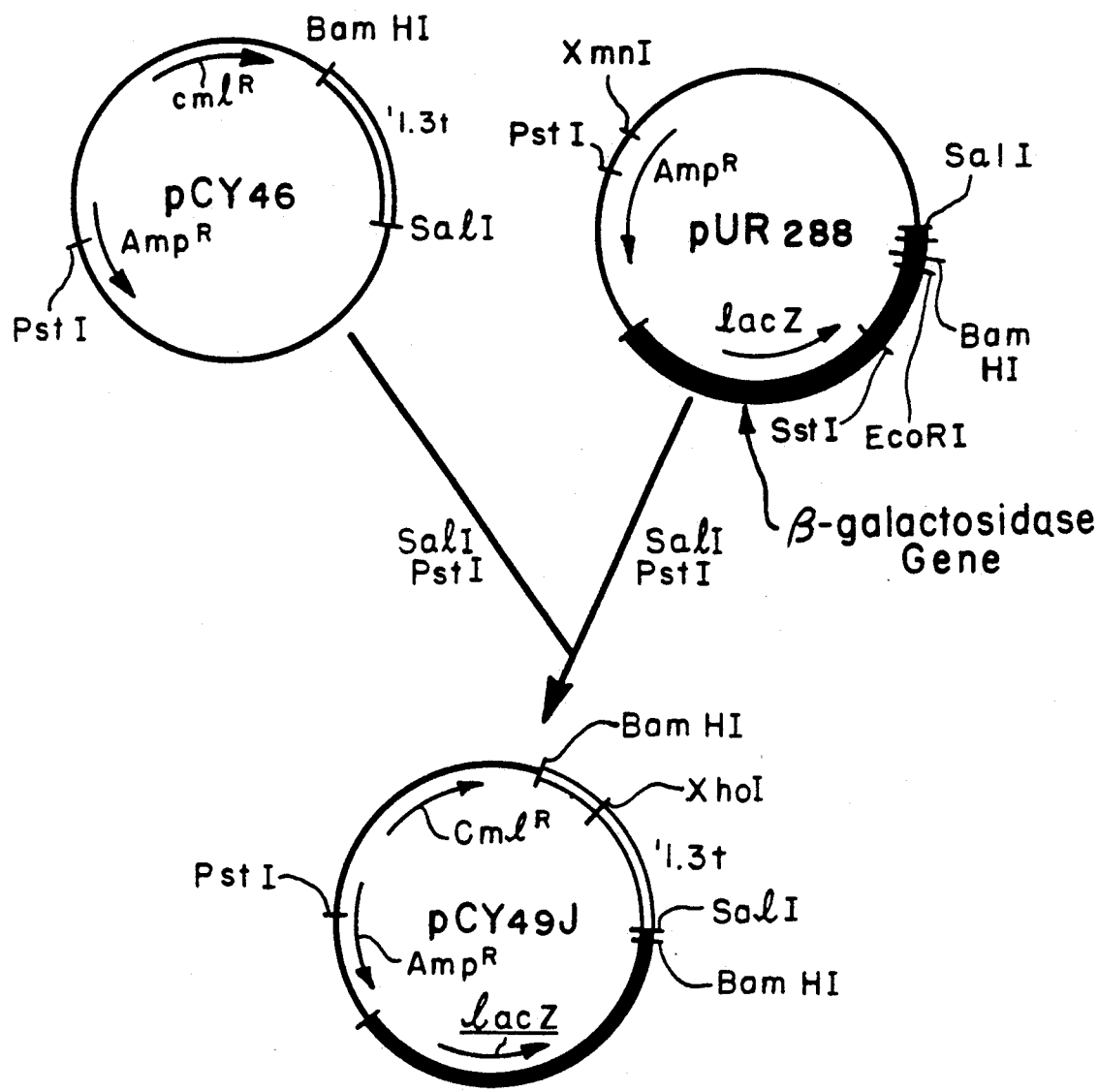
FIG. 4: Illustrates the preparation of vector pCY49J.

Plasmid pCY49J carrying Fusion A was prepared as shown in FIGS. 3 and 4. As shown there, plasmid ptacl.3t was digested with BamHI and SalI. This fragment was inserted into the BamHI and SalI sites of plasmid pBR328 to produce plasmid pCY46. Plasmid pBR328 is available from ATCC, accession number 37517. Next, plasmid pCY46 was digested with SalI and PstI, and the resulting fragment was ligated into the SalI and PstI sites of plasmid pUR288 to produce plasmid pCY49J carrying Fusion A.

Plasmid pUR288 carries a lacZ gene having unique cloning sites at the 3' end which are SalI, BamHI, XbaI and HindIII sites. The preparation of plasmid pUR288 and its properties are described in Ruther and Muller-Hill, *The EMBO Journal*, 2, 1791–94 (1983). It was obtained from Professor Muller-Hill, Universitat zu Köln, 5000 Köln 41, FRG. Portions of the linkers that create the unique cloning sites at the 3' end of the lacZ gene on pUR288 are retained in the Fusion A construction and are located between the sequences coding for beta-galactosidase and the 1.3S subunit fragment in Fusion A (represented by ~~~~~ in FIG. 21).

2. Preparation of Fusion B

Fusion B is a hybrid DNA sequence comprising the entire coding sequence of the beta-galactosidase gene linked in proper reading frame to a DNA sequence encoding the carboxyl terminal 75 amino acids of the 1.3S subunit. See FIG. 21.

Figure 5:
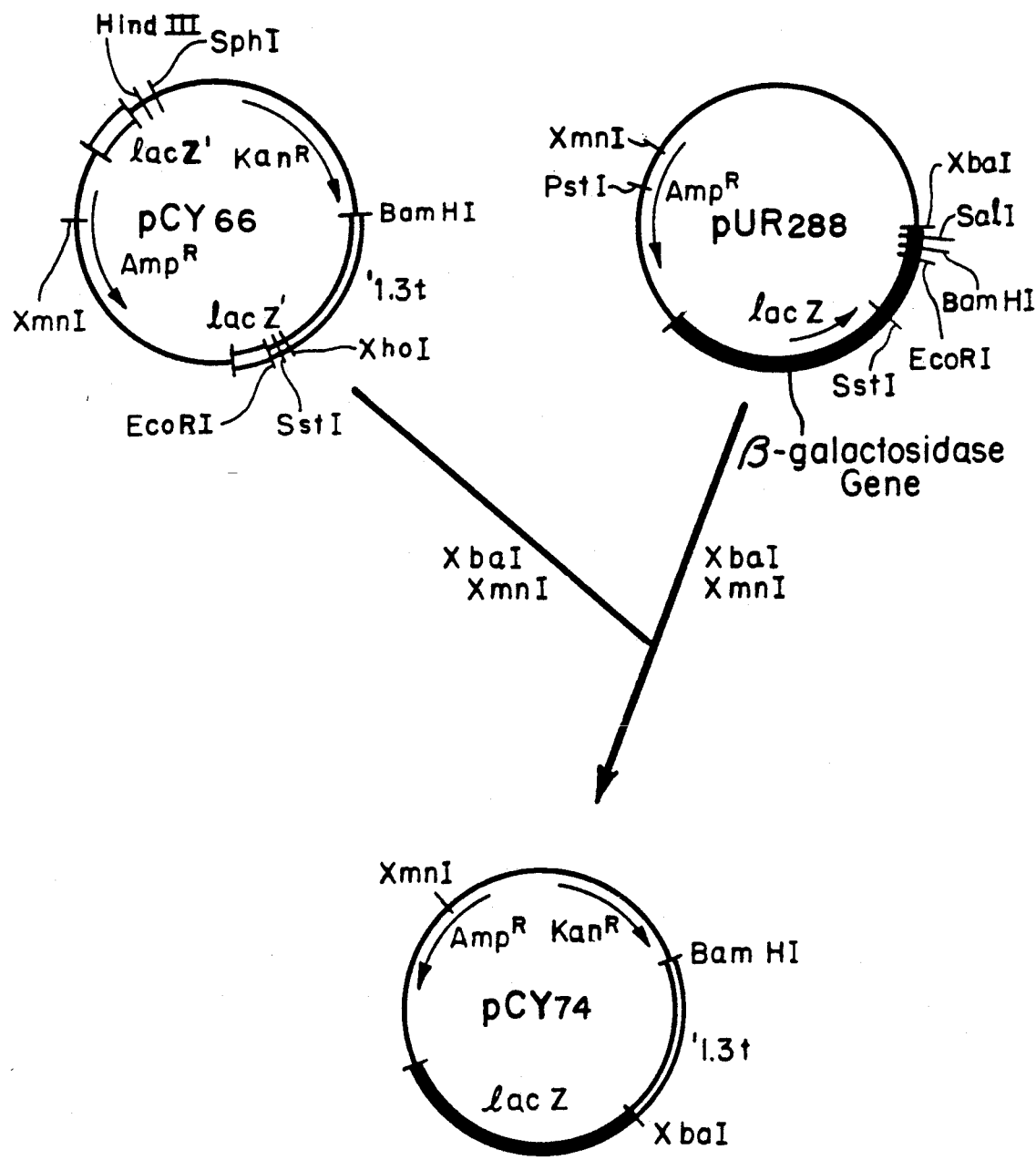
FIG. 5 Illustrates the preparation of vector pCY74.
Figure 11:
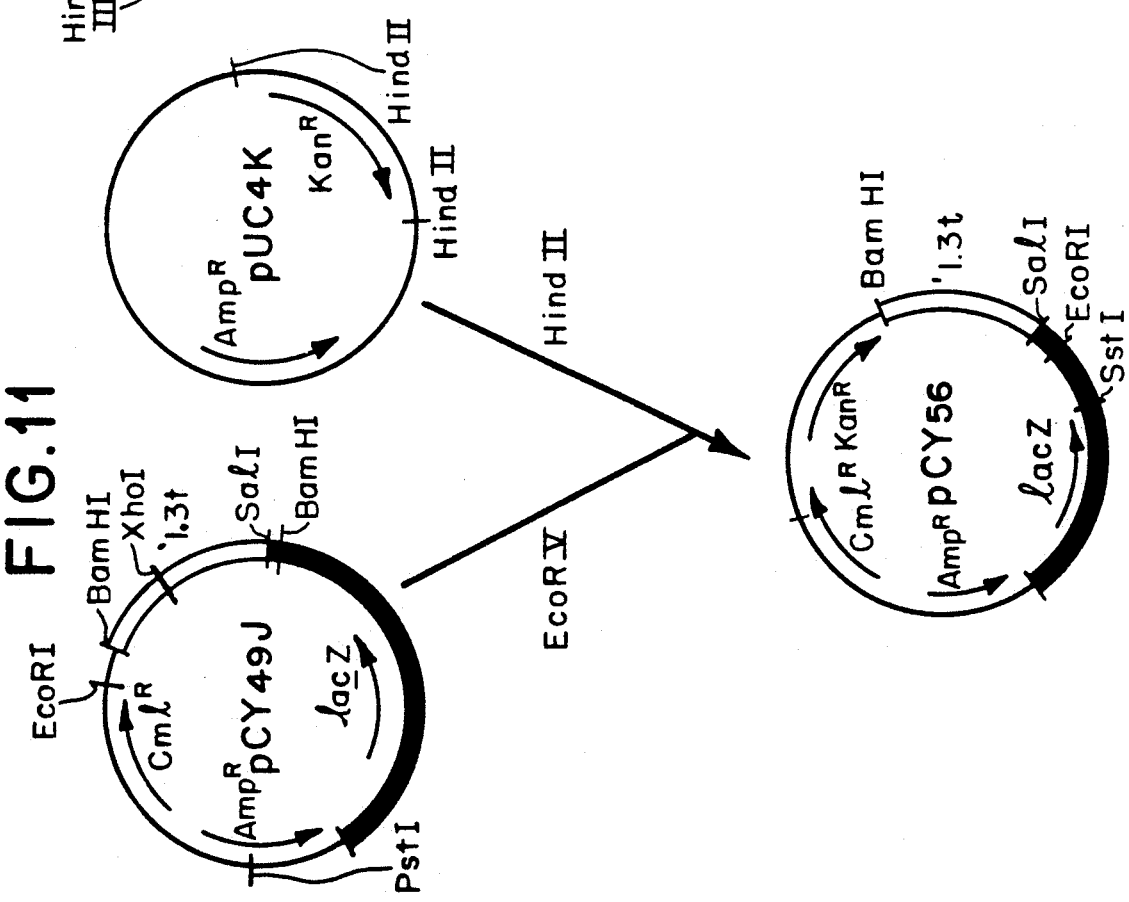
FIG. 11: Illustrates the preparation of vector pCY56.
Figure 12:
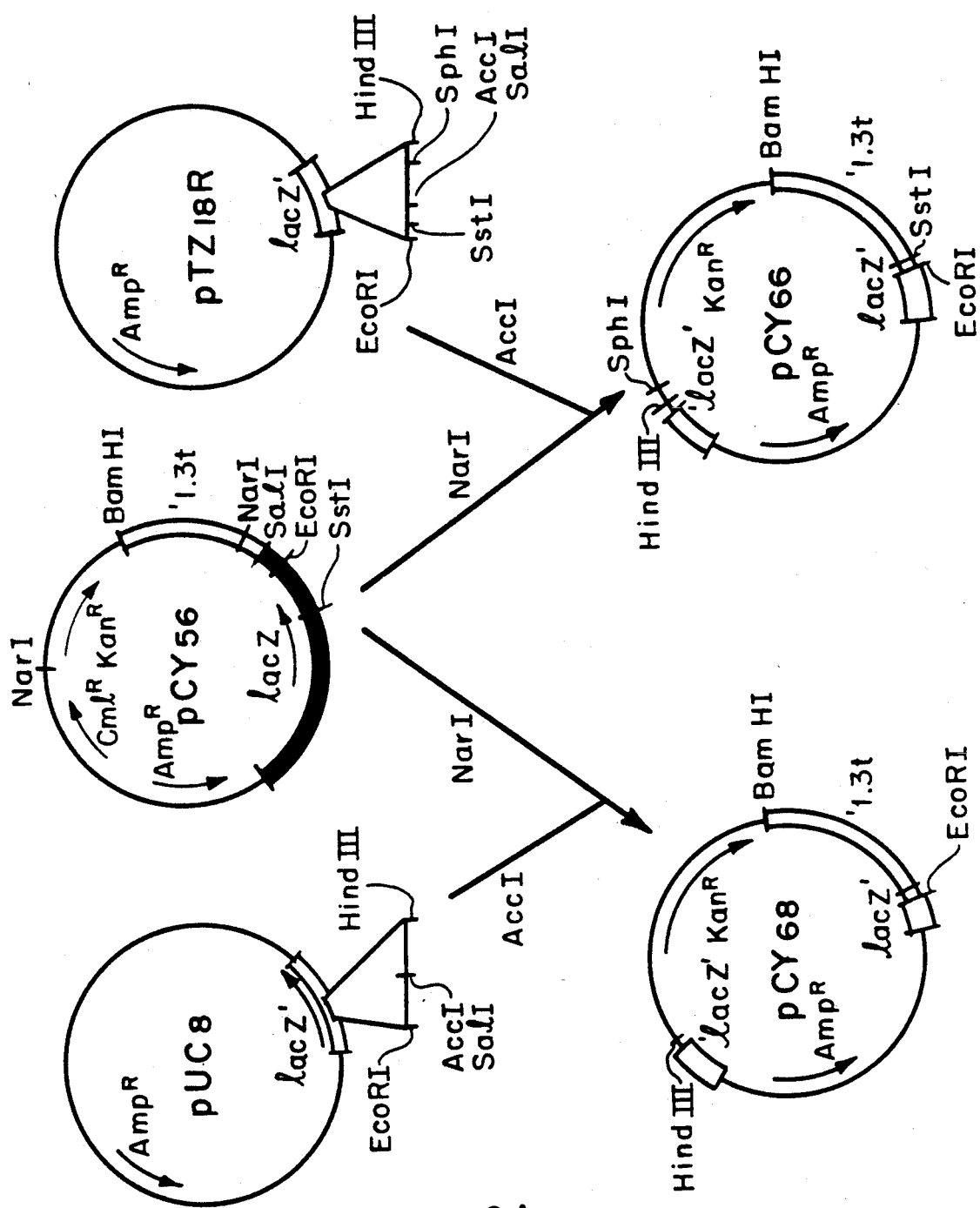
FIG. 12: Illustrates the preparation of vectors pCY66 and pCY68.

Plasmid pCY74 carrying Fusion B was prepared as shown in FIGS. 5, 11 and 12. First, plasmid pCY49J carrying Fusion A was linearized with EcoRV, and the HindII fragment from plasmid pUC4K carrying the kanamycin resistance gene was inserted into the EcoRV site on pCY49J to create plasmid pCY56 (see FIG. 11). Plasmid pUC4K is available from Pharmacia LKB Biotechnology, Pistcataway, N.J. Also see Viera and Messing, *Gene*, 19, 219 (1982).

Next, plasmid pCY56 was digested with NarI. Plasmid pTZ18R was linearized with AccI, and the NarI fragment from pCY56 was ligated into the AccI site of pTZ18R to produce plasmid pCY66 (see FIG. 12). AccI digestion gives protruding 5' ends complementary to the ends made by NarI.

Plasmid pTZ18R is available from Pharmacia LKB Biotechnology. Also see Mead et al., *Prot. Engineer* 1, 67 (1986).

Finally, plasmid pCY66 was digested with XbaI and XmnI, and the resulting fragment was ligated into the XbaI and XmnI sites of pUR288 to produce plasmid pCY74 carrying fusion B (see FIG. 5).

3. Preparation of Fusion C

Fusion C is a hybrid DNA sequence comprising the entire coding sequence of the beta-galactosidase gene linked in proper reading frame to a DNA sequence encoding the carboxyl terminal 61 amino acids of the 1.3S subunit. See FIG. 21.

Figure 6:
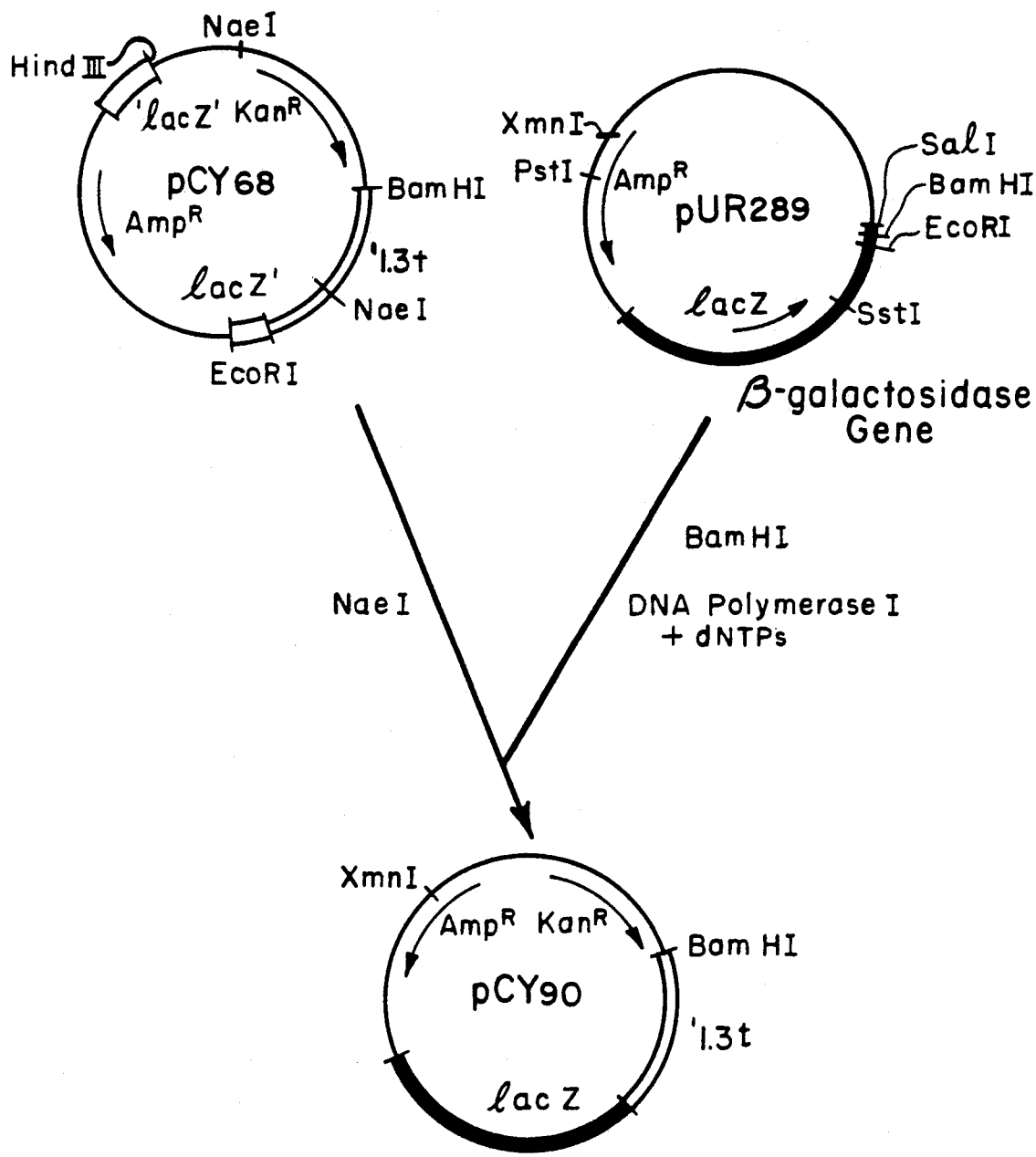
FIG. 6: Illustrates the preparation of vector pCY90.

Plasmid pCY90 carrying Fusion C was prepared as shown in FIGS. 6 and 12. Plasmid pUC8 was linearized with AccI, and plasmid pCY56 (prepared as described in FIG. 11) was digested with NarI. The NarI fragment from pCY56 was inserted into the AccI site of pUC8 to produce plasmid pCY68 (see FIG. 12).

Then, plasmid pCY68 was digested with NaeI. Plasmid pUR289 was cut with BamHI, and the ends were filled in with DNA polymerase I and dNTP's. The NaeI fragment of pCY68 was ligated to pUR289 treated as described to produce plasmid pCY90 carrying fusion C.

Plasmid pUR289 carries a lacZ gene having unique cloning sites at the 3' end which are SalI, BamHI, XbaI and HindIII sites. Portions of the linkers that create the unique cloning sites in pUR289 are retained in the Fusion C construction (represented by ~~~~~ in FIG. 21). The preparation of plasmid pUR289 and its properties are described in Ruther and Muller-Hill, *The EMBO Journal*, 2, 1791–94 (1983). It was obtained from Professor Muller-Hill.

Plasmid pUC8 is a well-known vector. It is available from Boehringer Mannheim Biochemicals and Pharmacia LKB Biotechnology. See also Viera and Messing, *Gene*, 19, 219 (1982).

4. Preparation of Fusion D

Fusion D is a hybrid DNA sequence comprising the entire coding sequence of the beta-galactosidase gene linked in proper reading frame to a DNA sequence encoding the carboxyl terminal 38 amino acids of the 1.3S subunit. See FIG. 21.

Plasmid pCY84 carrying Fusion D was prepared as shown in FIG. 7. Plasmid pCY84 was prepared by cutting pCY49J with SalI and XhoI and recircularizing to produce plasmid pCY84.

5. Preparation of Fusion E

Fusion E is a hybrid DNA sequence comprising a sequence coding for the 1006 amino terminal amino acids of beta-galactosidase linked in proper reading frame to a DNA sequence encoding the carboxyl terminal 75 amino acids of the 1.3S subunit. See FIG. 21.

Plasmid pCY72 carrying Fusion E was prepared as shown in FIG. 8. As shown there, this plasmid was prepared by digesting pCY66 (preparation shown in FIG. 12) with XmnI and EcoRI and ligating the resulting fragment into the XmnI and EcoRI sites of pUR288 to form plasmid pCY72.

6. Preparation of Fusion F

Fusion F is a hybrid DNA sequence comprising a sequence coding for the 650 amino terminal amino acids of beta-galactosidase linked in proper reading frame to a DNA sequence encoding the carboxyl terminal 75 amino acids of the 1.3S subunit. See FIG. 21.

Figure 9:
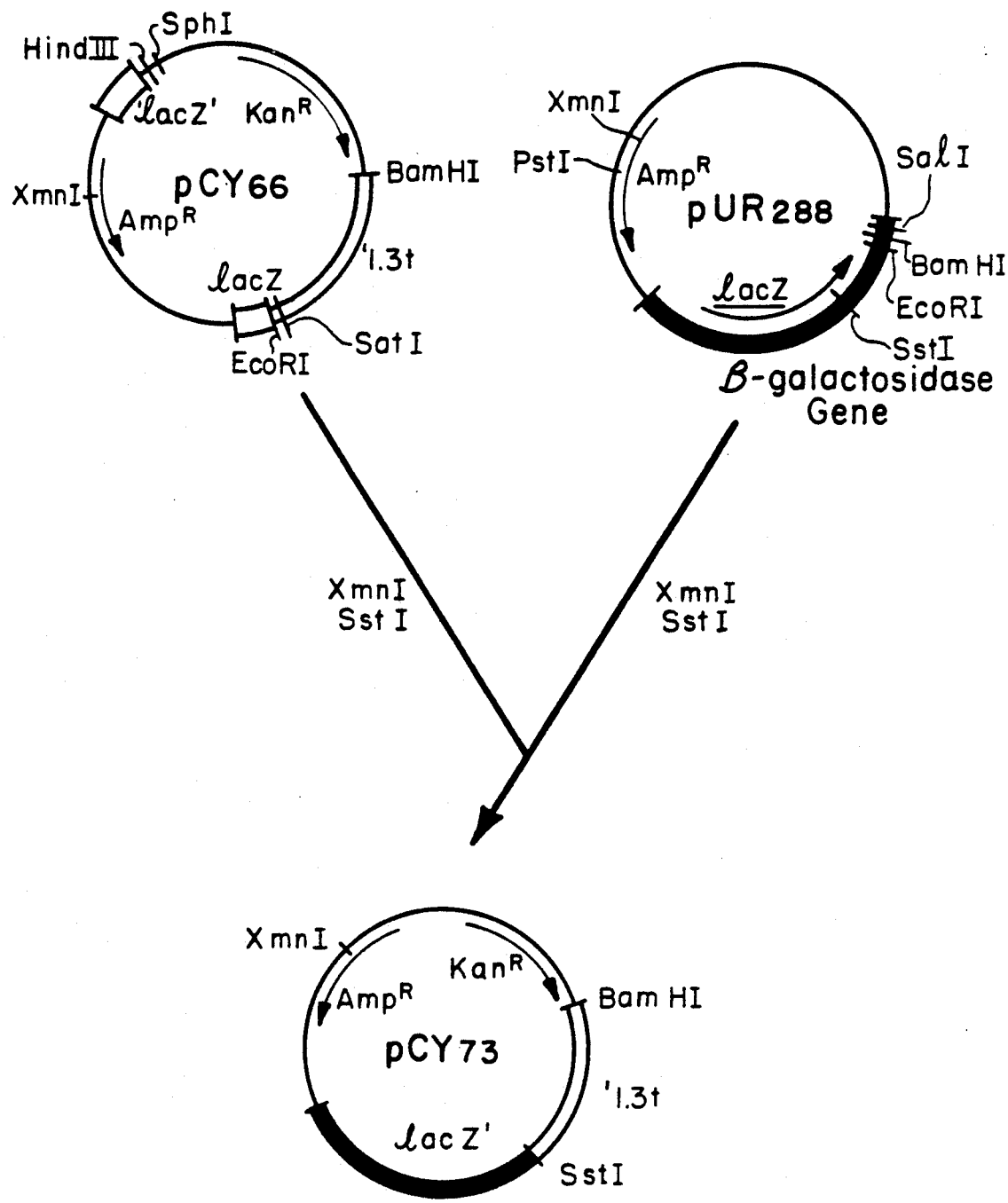
FIG. 9: Illustrates the preparation of vector pCY73.

Plasmid pCY73 carrying Fusion F was prepared as shown in FIG. 9. The preparation of plasmid pCY73 was accomplished by digesting plasmid pCY66 (preparation shown in FIG. 12) with XmnI and SstI and ligating the fragment produced thereby into the XmnI and SstI sites of pUR288 to produce plasmid pCY73.

7. Preparation of Fusion G

Fusion G is a hybrid DNA sequence comprising a sequence coding for the first 4 amino terminal amino acids of beta-galactosidase linked in proper reading frame to a DNA sequence encoding the carboxyl terminal 106 amino acids of the 1.3S subunit. See FIG. 21.

Figure 10:
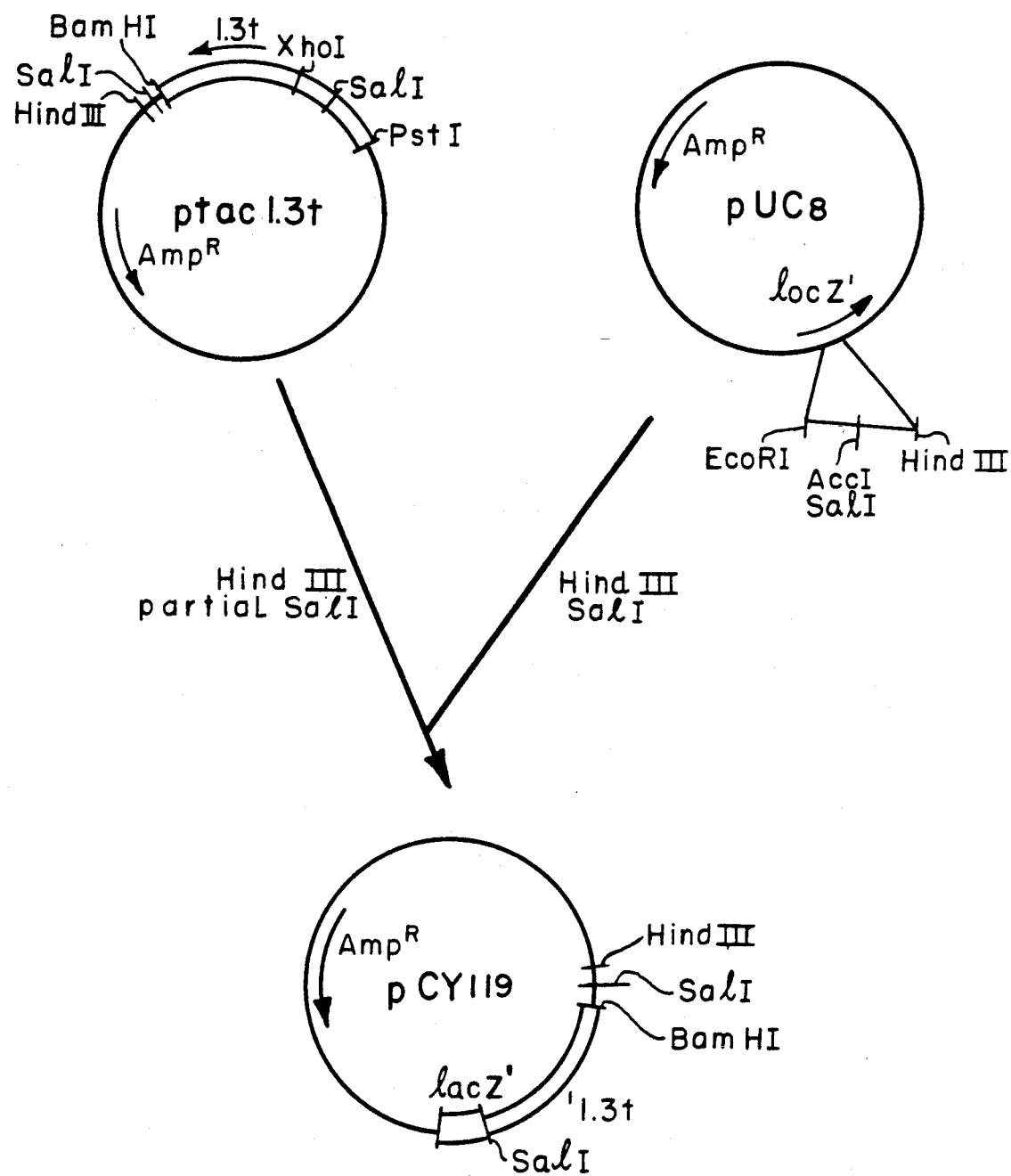
FIG. 10: Illustrates the preparation of vector pCY119.

Plasmid pCY119 carrying Fusion G was prepared as shown in FIG. 10. As shown there, plasmid ptac1.3t was digested with HindIII and then partially digested with SalI. The resulting fragment was inserted into the HindIII and SalI sites of pUC8 to form plasmid pCY119.

8. Preparation of Fusion H

Fusion H is a hybrid DNA sequence comprising a sequence coding for the first 4 amino terminal amino acids of beta-galactosidase linked in proper reading frame to a DNA sequence encoding the carboxyl terminal 75 amino acids of the 1.3S subunit. See FIG. 21.

Plasmid pCY68 carrying Fusion H was prepared as shown in FIG. 12. To prepare plasmid pCY68, plasmid pCY56 was cut with NarI, and plasmid pUC8 was cut with AccI. They were combined and recircularized to produce plasmid pCY68 carrying Fusion H.

9. Preparation of Fusion I

Fusion I is a hybrid DNA sequence comprising a sequence coding for the first 4 amino terminal amino acids of beta-galactosidase linked in proper reading frame to a DNA sequence encoding the carboxyl terminal 38 amino acids of the 1.3S subunit. See FIG. 21.

Figure 13:
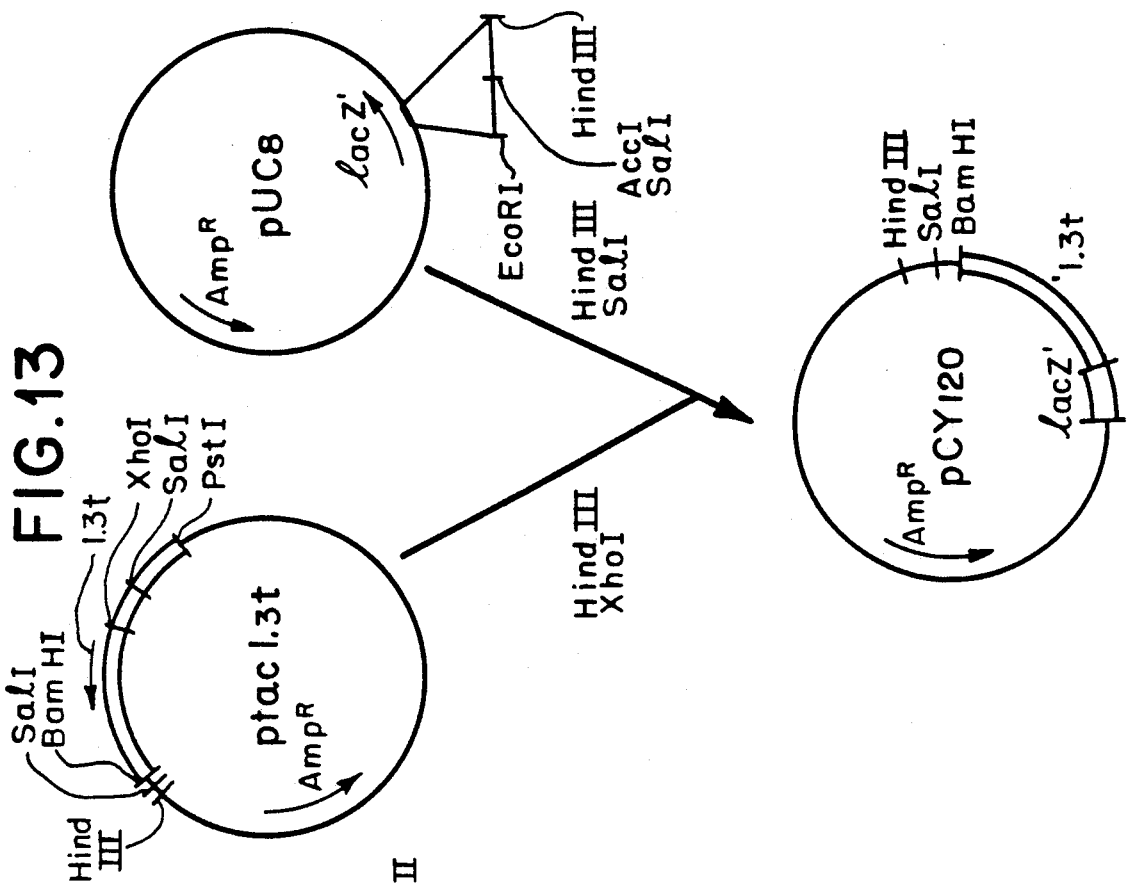
FIG. 13: Illustrates the preparation of vector pCY120.

Plasmid pCY120 carrying Fusion I was prepared as shown in FIG. 13. As shown there, plasmid ptac1.3t was digested with HindIII and XhoI. The resulting fragment was inserted into the HindIII and SalI sites of pUC8 to form plasmid pCY120 carrying Fusion I. XhoI digestion results in fragments with 5' protruding ends complementary to those produced by SalI.

B. Transformation Of Hosts And Expression and Detection of Biotinated Proteins

1. Transformation

Several *E. coli* strains were transformed with the vectors prepared as described above carrying Fusions A-I. The transformation was done as described by Maniatis et al., *Molecular Cloning*, pp. 403-433 (Cold Spring Harbor Press, Cold Spring Harbor, N.Y. 1982), modified by the inclusion of 20 mM $MgCl_2$ in all buffers as recommended by Hanahan, *J. Mol. Biol.*, 166, 557 (1983).

The strains of *E. coli* used were: NM522 and its restriction-positive parent BMH71-18; F'11recA: DH5α; F'M15recA: and MC1061. Strains BMH71-18 and F'11recA were gifts of Professor B. Muller-Hill, and are described in Ruther and Muller-Hill, *The EMBO J.*, 2, 1791-94 (1983). Strain DH5α was obtained from Bethesda Research Laboratories. Strains NM522, F'M15recA and MC1061 are available from the ATCC, accession numbers 47000, 33904 and 53338 respectively. The primary attribute of all five strains is the high frequency of transformation.

Strains DH5α, F'M15recA, NM522 and BMH71-18 carry a small deletion of the lacZ gene (called M15) which produces an inactive beta-galactosidase, the activity of which can be restored by the presence of a second inactive beta-galactosidase fragment encoded by vectors such as pUC8 and pTZ18R. This process of producing an active beta-galactosidase from two inactive proteins is called alpha-complementation, and it is in general use since insertion of a DNA fragment within the polylinker sequences placed in the lacZ sequences of pUC8, pTZ18R and similar vectors results in loss of beta-galactosidase activity. This loss of activity was ascertained by including 5-bromo-4-chloro-indoylbeta-galactoside (purchased from Sigma Chemical Co.) in the culture medium, the preparation of which is described below.

Strain F'11recA has a deletion of the entire chromosomal lactose operon, but contains an F' factor carrying the lacI*q* lesion which overproduces the lactose operon repressor protein. Strains BMH71-18 and NM522 also carry this F'lacI*q* factor. The lactose repressor regulates the expression of any lactose operon-derived fusion protein.

The medium used for the transformation procedures was a broth consisting of 1% Bacto tryptone (purchased from Difco Laboratories), 0.1% Bacto Yeast Extract (purchased from Difco Laboratories), and 0.5% NaCl. Solid medium contained 1.5% agarose.

Antibiotics were added as appropriate to select transformants. They were added to give final concentrations of: sodium ampicillin (100 ug/ml), kanamycin sulfate (50 ug/ml); and chloramphenicol (50 ug/ml). The antibiotics were added to liquid medium or to molten agar medium at 55° C. immediately before pouring it into Petri dishes. All antibiotics were purchased from Sigma Chemical Co.

2. Assay For Radioactively-Labeled Biotinated Proteins

The *E. coli* strains transformed with Fusions A-I as described above were cultured with tritiated biotin to label the fusion proteins. The bacteria were cultured at 37° C. to $1-2 \times 10^9$ cells/ml in minimal medium E containing 0.4% glycerol, 0.1% vitamin free casein hydrolysate, 41 nM tritiated biotin (1 µCi of $^3$H biotin/ml) (purchased from New England Nuclear or Amersham) and appropriate antibiotics to select for plasmid maintenance.

After overnight culture, 0.1 ml aliquots containing $1-2 \times 10^8$ cells were placed in test tubes containing 1.0 ml of the same medium supplemented with 1 mM isopropyl-thio-galactoside (IPTG) (purchased from Sigma Chemical Co.). The cells were cultured for 2 hours to obtain expression of the fusion proteins, after which the cells were harvested, lysed in a solution of 12.5mM Tris-HCl, pH 6.8, containing 8M urea and 1% sodium dodecyl sulfate (SDS). The cell extracts were separated on a 7.5% polyacrylamide gel run in the discontinuous mode in the presence of SDS. The gels were fluorographed by soaking them in Enhance (purchased from New England Nuclear) and then exposing them to preflashed film. The results are presented in FIG. 21.

The production of biotinated proteins can also be detected using a technique based on the binding of biotin by streptavidin or avidin. See Buckland, *Nature*, 320, 557 (1986); Wilchek and Bayer, *Anal. Biochem.*, 171, 1, (1988); Wilchek and Bayer, *Meth. Enzymol.*, 184, in press.

3. Assay For Bio Operon Derepression

Biotin (bio) operon derepression was also assayed for each of the fusions. The bio operon contains the genes coding for the enzymes that synthesize biotin. The rate of synthesis of the biotin biosynthetic enzymes is controlled by a repressor, the activity of which depends on the external supply of biotin and, in *E. coli*, is sensitive to the cellular level of biotin-acceptor proteins. Eisenberg, *Ann. N.Y. Acad. Sci.*, 447, 335-49 (1984); Cronan, *J. Biol. Chem.*, 263 10332-36 (1988).

However, the regulation of this operon differs from the usual repression system in two novel properties. First, the repressor protein and the biotin ligase are the same protein. That is, the protein contains both a biotin operator-specific DNA binding domain and the ligase active site. The second novel property is that the co-repressor that activates DNA binding is not biotin, but is biotinoyl-AMP, the product of the first half-reaction of the biotin ligase activity. Id. Biotinoyl-AMP remains enzyme bound until consumed in the biotination of an acceptor biotin protein.

Maximal rates of bio operon transcription (derepression) occurs when the biotin supply is severely limited (such as biotin starvation of a bio auxotroph). Since any biotinoyl-AMP synthesized is rapidly consumed in biotination of acceptor proteins, no appreciable amount of repressor ligase-biotinoyl-AMP complexes accumulate, the bio operator is very seldom occupied, and transcription is maximal. Thus, biotination consumes biotinoyl-AMP and results in derepression of the bio operon.

Derepression of the bio operon can be observed on indicator plates and quantitated by β-galactosidase activity as described below, thereby providing a means to assay for the synthesis of biotinated protein fusions in *E. coli*. This system also allows fusions that are biotinated, but degraded, to be distinguished from those which fail to be biotinated.

A qualitative assay was performed by transforming *E. coli* strain BM2661, described in Barker and Campbell, *J. Bacteriology*, 143, 789-800 (1988), with the vectors carrying Fusions A-I. Strain BM2661 carries a truncated beta-galactosidase gene fused to the promoter of the bio BCDF operon of *E. coli*. When biotin biosynthesis is derepressed, beta-galactosidase is produced, whereas very low expression is seen when high concentrations of exogenous biotin are present in the medium. Strain BM2661 was obtained from Dr. Campbell, Stanford University.

The indicator medium used was MacConkey lactose (purchased from Difco Laboratories), supplemented with 41 nM or 5 uM biotin. On this medium, repressed colonies are white, whereas derepressed colonies are pink or red depending on the extent of derepression. The results are given in FIG. 21.

A quantitative assay can be done by disrupting the cells and assaying for beta-galactosidase by hydrolysis of o-nitrophenyl-galactoside as described in Cronan, *J. Biol. Chem.*, 263, 10332-36 (1988) and Barker and Campbell, *J. Bacteriology*, 143, 789-800 (1988).

4. Results

The results of the two assays described above are shown in FIG. 21. A "+" in the biotinated protein column indicates that a tritiated fusion protein of the expected size and abundance was detected. A "+" in the derepression column indicates that transcription of the biotin operon was increased at least 10-fold in the presence of 41nM biotin (the minimal concentration giving maximal repression in wild type cells), whereas "++" indicates that at least 10-fold derepression was observed at 5 uM biotin.

As shown in FIG. 21, the protein produced by Fusion D coding only the carboxyl terminal 38 amino acids of the 1.3S subunit, which are the amino acid residues from the biocytin lysine residue to the carboxyl terminus, failed to be biotinated. This indicates that sequences upstream of the biocytin lysine are required for recognition of the protein by biotin ligase.

It seems likely that a required sequence is the pro-ala-pro sequence (residues 58-60) of the 1.3S subunit (a putative β-turn) since proteins produced by Fusions C and D lacking this segment failed to be biotinated (see FIG. 21), whereas Fusions A, B, and E-H that included this segment bound biotin (see FIG. 21). However, there may be more subtle structures in this region that are important for ligase recognition.

Of particular interest are Fusions B, E, F and H which have a biotination site consisting of the last 75 carboxyl terminal amino acids of the 1.3S subunit. This is the minimum amino acid sequence found to date which gives biotination.

It should be noted that some of the biotin fusions are degraded by intracellular proteases. Fusion E produced a very weak biotinated protein band at the expected migration position. This result is believed to be due to proteolytic clipping at the junction between the betagalactosidase and the biotin-binding sequence. The junction of the DNA segments is the EcoRI site of the β-galactosidase lacZ gene. This site has also been used in the λgt11 system, and proteolytic clipping at the fusion junction has been observed for many fusions. Carroll and Laufhon, in *DNA Cloning*, vol. 3, pp. 89-111 (Glover ed., IRL Press, Oxford, U.K. 1987). This problem of proteolytic cleavage should be solved by using protease deficient *E. coli* hosts or by altering the sequence at the junction of the two segments of a fusion protein.

However, degradation of fusions can be distinguished from a non-functional acceptor sequence by the derepression of the biotin operon given by a degraded fusion, but not by a fusion having a non-functional acceptor sequence. As can be seen in FIG. 21, there was a high level of derepression for Fusion E, indicating that the acceptor sequence was functional.

Figure 14:
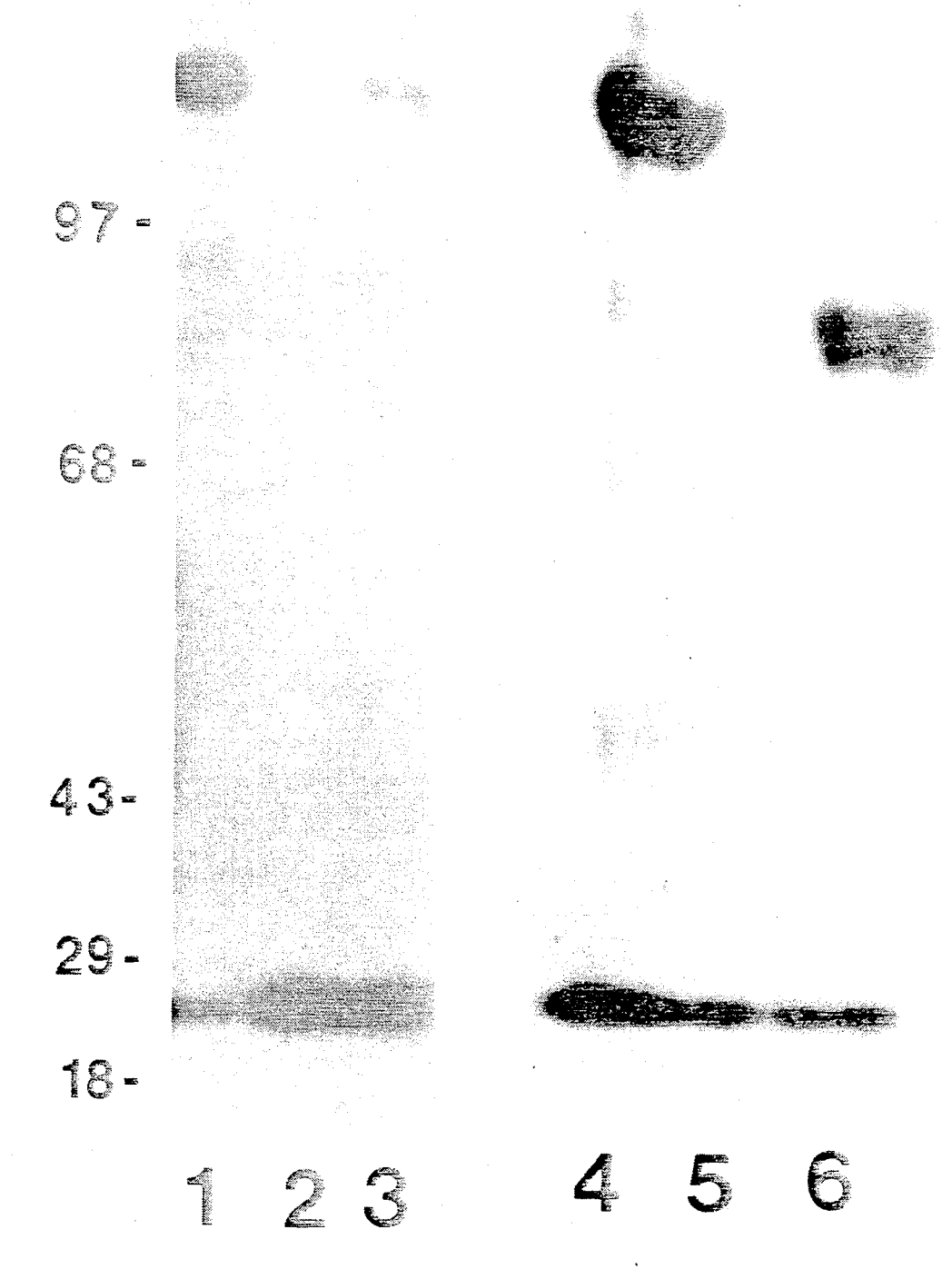

FIG. 14 shows a typical fluorograph obtained using the tritiated labeling procedure described above. In FIG. 14, Lane 1 contains the protein produced by Fusion A, Lane 2 contains no fusion protein; Lane 3 contains the protein produced by Fusion A but uninduced; Lane 4 contains the protein produced by Fusion B; Lane 5 contains the protein produced by Fusion E (a faint band was observed upon overexposure); and Lane 6 contains the protein produced by Fusion F. The lower band in all lanes is the endogenous *E. coli* biotin carboxyl carrier protein.

EXAMPLE 2

Preparation and Expression of DNA Sequences Encoding Fusion Proteins Having a Site For Post-Translation Biotination Fusion J is a hybrid DNA sequence encoding the amino terminal 209 amino acids of Tn9 chloramphenicol acetyltransferase and the DNA sequence encoding the carboxyl terminal 75 amino acids of the 1.3S subunit. See FIG. 21.

Figure 15:
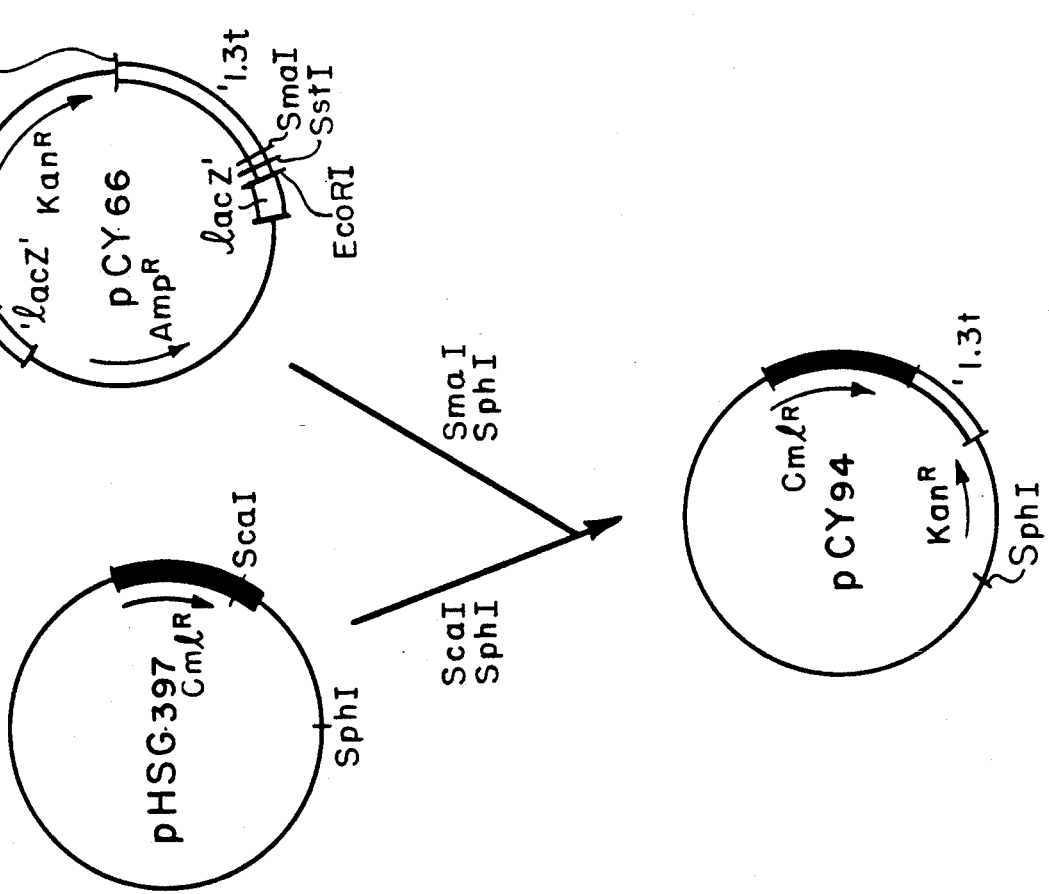
FIG. 15: Illustrates the preparation of vector pCY94.

Plasmid pCY94 carrying Fusion J was prepared as shown in FIG. 15. As shown there, plasmid pCY66 (preparation shown in FIG. 12) was digested with SmaI and SphI. The resulting fragment was inserted into the ScaI and SphI sites of plasmid pHSG397 to form plasmid pCY94 carrying Fusion J.

Plasmid pHSG397 was obtained from the Japanese Cancer Research Resource Bank, Tokyo. Also see Takeshita et al., *Gene*, 61, 63 (1987).

Plasmid pCY94 was used to transform *E. coli* strains DH5α and BM2661. Strain DH5α was incubated with tritiated biotin as described in Example 1, and strain BM2661 was tested for derepression as described in Example 1, except that no lactose operon inducer was added.

The results are shown in FIG. 21. As shown there, a biotinated fusion protein was produced in strain DH5α, and derepression was observed when pCY84 was introduced into strain BM2661.

EXAMPLE 3

Preparation and Expression of DNA Sequences Encoding Fusion Proteins Having a Site For Post-Translation Biotination Fusion K is a hybrid DNA sequence encoding the amino terminal 44 amino acids of Tn5 neomycin phosphotransferase and the DNA sequence encoding the carboxyl terminal 75 amino acids of the 1.3S subunit. See FIG. 21.

Figure 16:
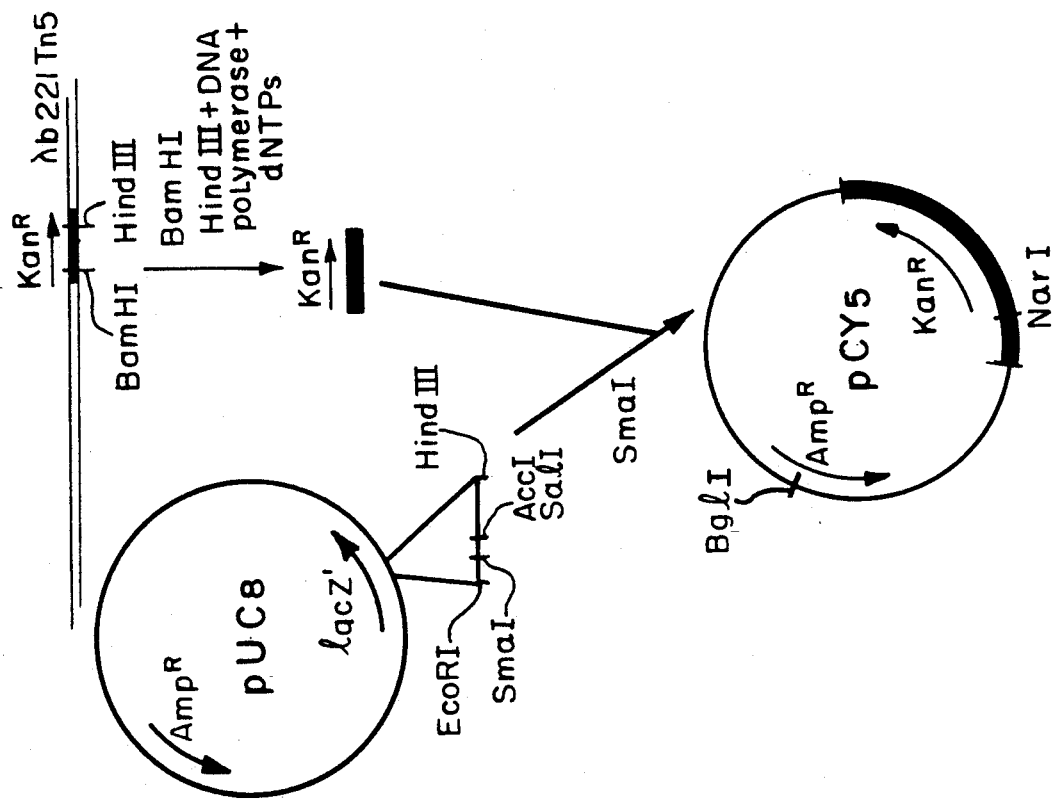
FIG. 16: Illustrates the preparation of vector pCY5.
Figure 18:
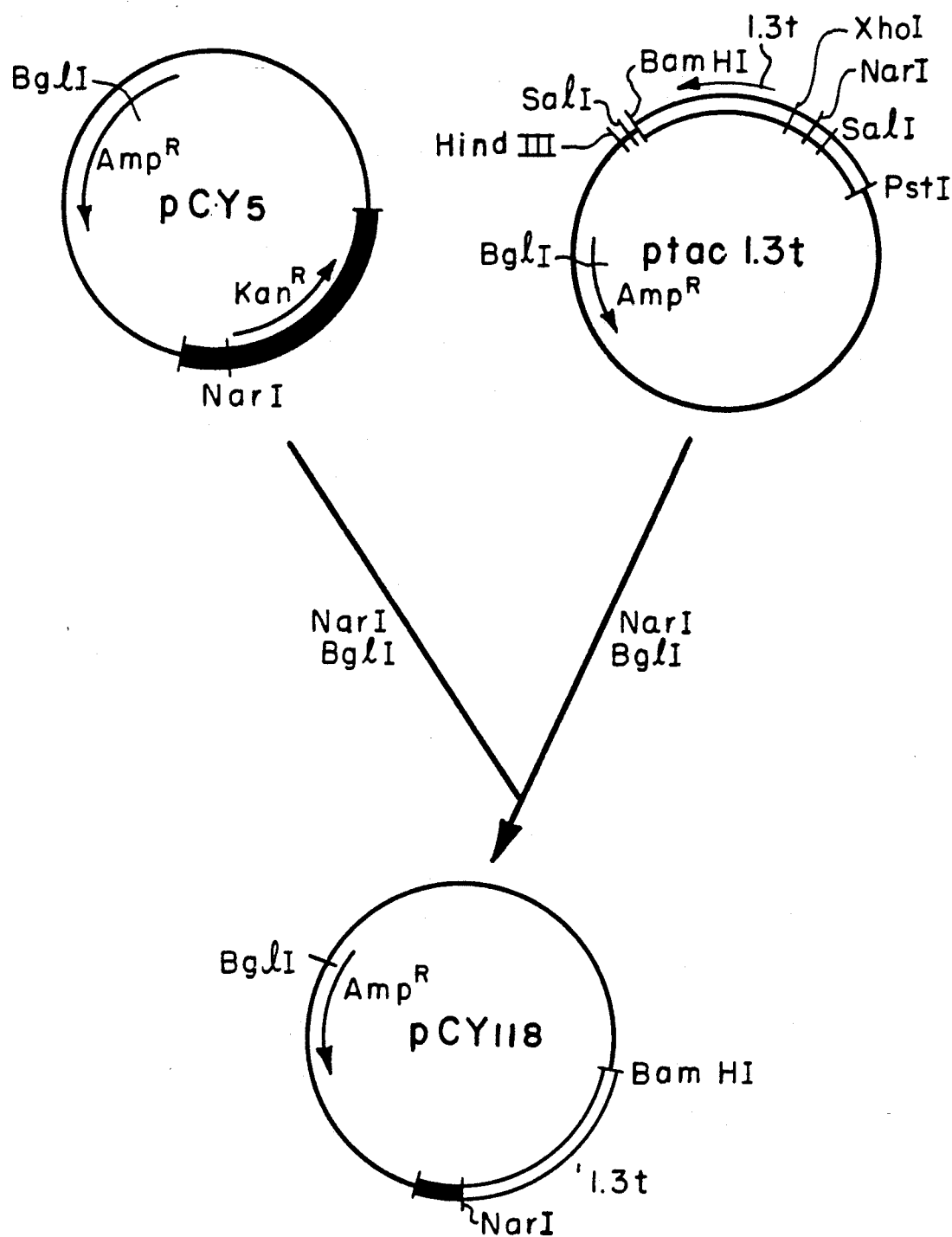
FIG. 18: Illustrates the preparation of vector pCY118.

Plasmid pCY118 containing Fusion K was prepared as shown in FIGS. 16 and 18. First, DNA from phage lambda b221 carrying transposon Tn5 was isolated and digested with BamHI and HindIII. The ends were filled in with *E. coli* DNA polymerase I (Klenow fragment) and dNTP's. Then this fragment was inserted into the SmaI site of pUC8 to produce plasmid pCY5. Next, pCY5 was digested with NarI and BglI, and the resulting fragment was inserted into the NarI and BglI sites of ptac1.3t to produce pCY118 carrying Fusion K.

Transposon Tn5 was obtained from D. Berg, Washington University, St. Louis, Mo. Its preparation is described in Berg et al., *Proc. Natl. Acad. Sci. U.S.A.*, 72, 3628-32 (1975). An anlogous DNA segment encoding the Tn5 neomycin phosphotransferase is available from Pharmacia Biotechnology.

Plasmid pCY118 was used to transform strain BMH71-18. This transformation was performed as described above in Example 1.

The transformed bacteria were incubated with tritiated biotin as described in Example 1 and assayed for derepression as described in Example 2. The results are shown in FIG. 21. As shown there, a biotinated fusion protein was produced, and derepression was observed.

EXAMPLE 5

Preparation and Expression of DNA Sequences Encoding Fusion Proteins Having a Site For Post-Translation Biotination Fusion M is a hybrid DNA sequence encoding the amino terminal 41 amino acids of the Tn903 neomycin phosphotransferase and the DNA sequence encoding the carboxyl terminal 75 amino acids of the 1.3S subunit. See FIG. 21.

Figure 19:
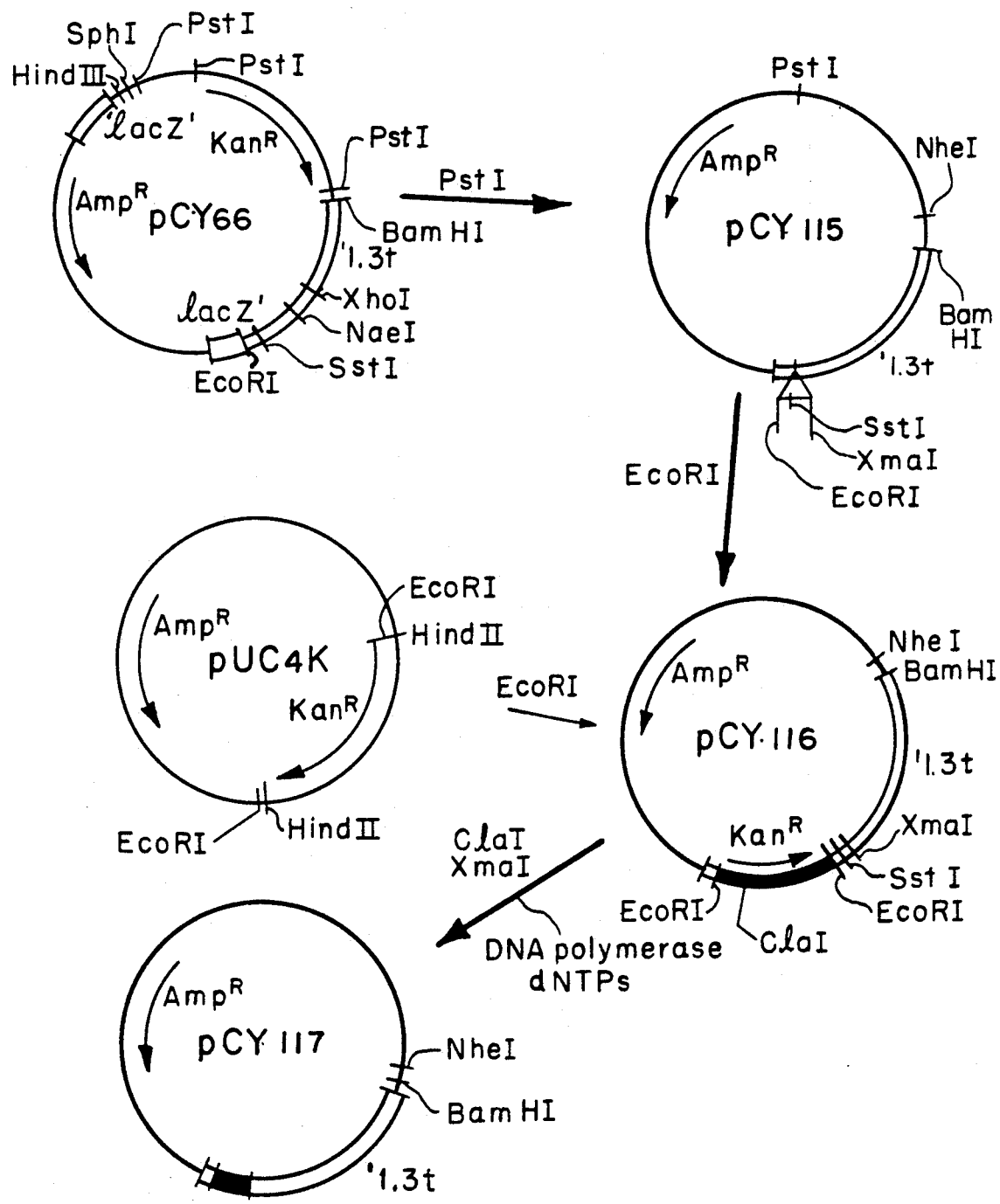
FIG. 19: Illustrates the preparation of vectors pCY116 and pCY117.

Plasmid pCY117 carrying Fusion M was prepared as shown in FIG. 19. First, plasmid pCY66 (prepared as shown in FIG. 12) was linearized with PstI and recircularized to form plasmid pCY115. Plasmid pUC4K was digested with EcoRI, and the resulting fragment was ligated into the EcoRI site of pCY115 to form plasmid pCY116. Finally, plasmid pCY116 was digested with ClaI and XmaI. The ends were filled in with *E. coli* DNA polymerase I (Klenow fragment) plus dNTP's, and the plasmid was recircularized to form plasmid pCY117 carrying Fusion M.

Plasmid pCY117 was used to transform *E. coli* strain MC1061. This transformation was performed as described above in Example 1. The transformed bacteria were incubated with tritiated biotin as described in Example 1 and assayed for derepression as described in Example 2. The results are shown in FIG. 21. As shown there, a biotinated fusion protein was produced, and derepression was observed.

EXAMPLE 6

Preparation of a Fusion Protein Comprising the HIS3 Protein Of Yeast And A Bacterial Biotination Sequence The gene coding for the HIS3 protein of yeast is also expressed in *E. coli* (due to the presence of adventitous sequences providing promoter and ribosome binding functions) where it complements *E. coli* hisB mutants. Struhl and Davis, *J. Mol. Biol.*, 136, 309-332 (1980). A hybrid DNA sequence which encodes the entire HIS3 protein, except the last six amino acids, fused to the sequence encoding the carboxyl terminal 75 amino acids of the 1.3S subunit was prepared which was expressed and biotinated in both *E. coli* and *S. cerevisiae*. This hybrid DNA sequence is Fusion L shown in FIG. 21.

Figure 17:
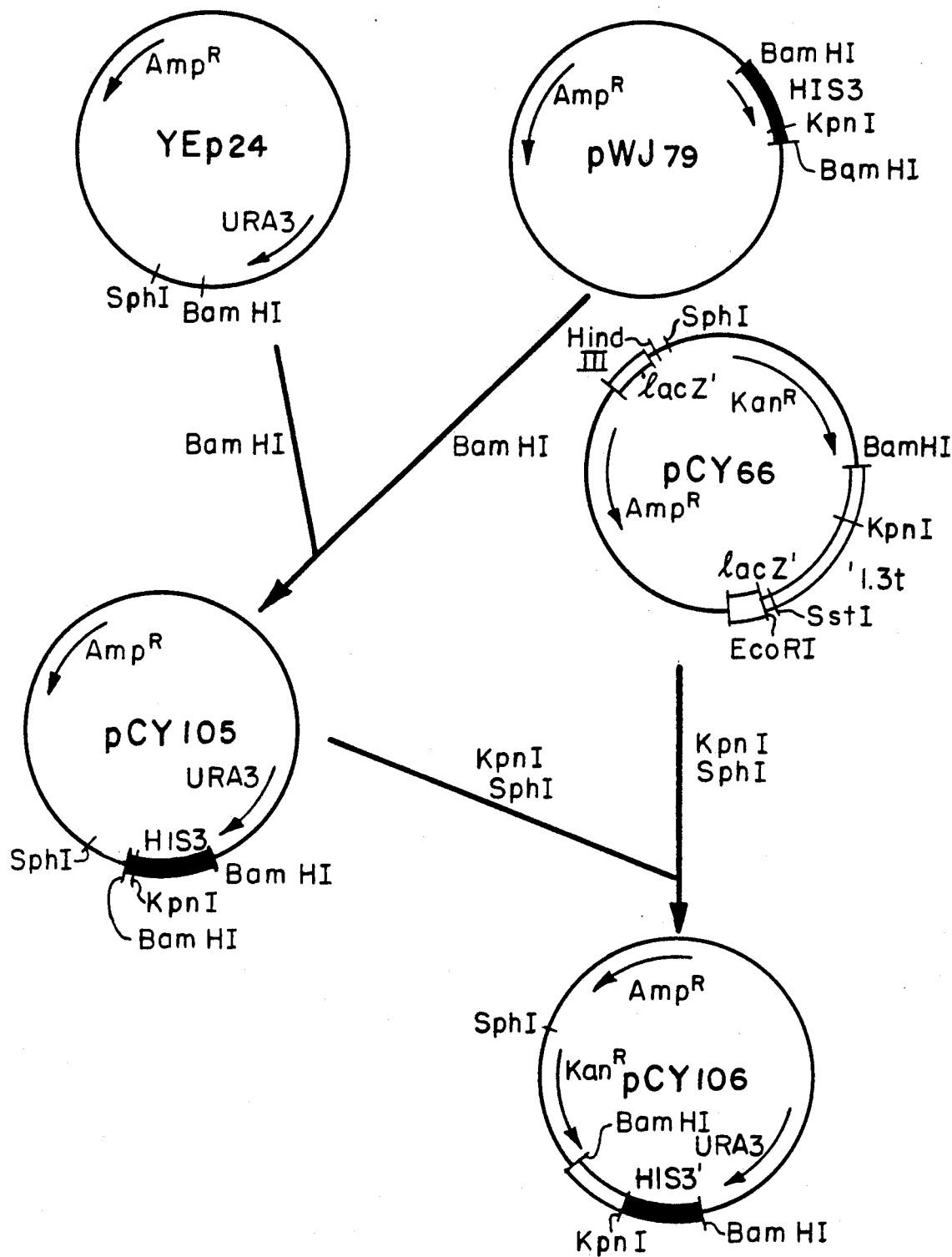
FIG. 17: Illustrates the preparation of vectors pCY105 and pCY106.

Plasmid pCY106 carrying Fusion L was prepared as shown in FIG. 17. First, plasmid pWJ79 was digested with BamHI, and this fragment was ligated into the BamHI site of plasmid YEp24 to produce plasmid pCY105.

Plasmid YEp24 is a shuttle vector able to replicate in both *E. coli* and *S. cerevisiae*. It was obtained from Dr. T. N. Davis, University of Washington, Seattle, Wash., but it is also available from the ATCC as pRB5, accession number 37051. Also see Botstein et al., *Gene*, 8, 17 (1979).

Plasmid pWJ79 was obtained from Dr. T. N. Davis, University of Washington, Seattle, Wash. It consists of the HIS3-containing BamHI fragment of Struhl and Davis (described in Struhl et al., *J. Mol Biol.*, 136 309-320 (1980)), cloned in the BamHI site of pBR322 (T. N. Davis, personal communication). Plasmid pBR322 is available from Pharmacia LKB Biotechnology and New England Biolabs and from ATCC, accession number 31344. The HIS3 DNA fragment is available from the ATCC as pRB14, accession number 37063.

Next, plasmid pCY66 was digested with KpnI and SphI, and the resulting fragment inserted into the corresponding sites on plasmid pCY105 to produce plasmid pCY106 carrying Fusion L.

Plasmid pCY106 was maintained in *E. coli* strain DH5α by selection for antibiotic resistance and in *S. cerevisiae* strain CTY186 by selection for uracil independence. Strain CTY186 carries a deletion of the chromosomal URA3 and HIS3 and a nonsense lesion in the LYS locus. Strain CTY186 was obtained from the collection of S. Emr, California Institute of Technology. It was prepared originally by Dr. V. Bankaitis, University of Illinois. A strain essentially identical to CTY186 is SHY1 available from ATCC, accession number 44769. Other essentially identical strains are available from Yeast Genetics Stock Culture Center, University of California, Berkeley, Calif.

Transformation of yeast strains was done as described by Ito et al., *J. Bacteriology*, 153, 163-68 (1983).

To label the biotinated proteins, the yeast were grown on a minimal medium supplemented with glucose (0.6%), 30 ug/ml lysine and biotin 20 nM (1 μCi/ml). Histidine-HCl was added at either 2.5 μg/ml or 50 μg/ml. The lower histidine concentration results in derepression of HIS3 transcription. Struhl, *Nature*, 300, 284-287 (1982).

The yeast cells were disrupted in a French pressure cell, and insoluble debris was removed by centrifugation. The proteins were recovered from the supernatant by trichloroacetic acid precipitation, washed free of acid, solubilized in SDS buffer (described in Example 1), and electrophoresed on a 12.5% polyacrylamide gel. The gel was fluorographed as described in Example 1.

The *E. coli* strain DH5α carrying pCY106 was labeled and prepared for electrophoresis as described in Example 1.

In both bacterial and yeast cells a new biotinated protein of the expected molecular weight (32 kDa) was found. See FIGS. 20 and 21. In yeast cells, the synthesis of this 32 kDa biotinated protein was regulated as is the normal HIS3 protein. Its synthesis was derepressed under conditions of histidine limitation and, upon derepression, the HIS3 fusion protein became the major biotinated protein of the yeast cells. See FIG. 20.

Figure 20:
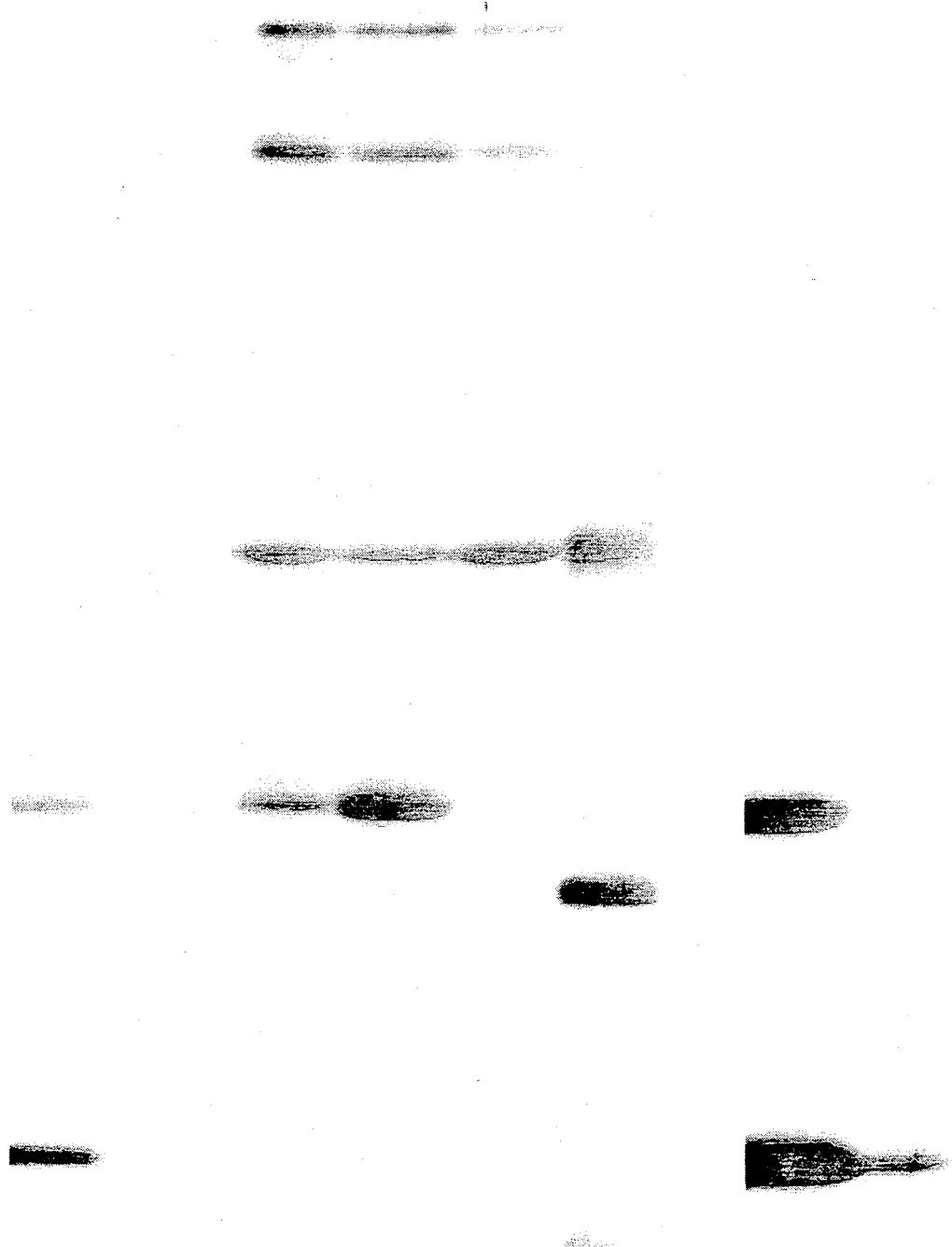
FIG. 20: A typical fluorograph of biotinated HIS3-1 3S fusion protein produced by *E. coli* and *Saccharomyces cerevisiae*.

In FIG. 20, Lane 1 contains the protein produced by *E coli* DH5α carrying Fusion L (pCY106); lane 2 contains the protein produced by *E. coli* DH5α carrying a YEp24 derivative with an intact HIS3 gene (pCY105); lanes 3 and 4 contain the protein produced by *S. cerevisiae* strain CTY186 carrying Fusion L (pCY106); Lane 5 contains the protein produced by yeast strain CTY186 carrying the intact HIS3 plasmid (pCY105); Lane 6 contains $^{14}$C-labeled molecular weight standards (ovalbumin-43kDa, carbonic anhydrase-29kDa, and betalactoglobulin-18.4kDa) purchased from Bethesda Research Laboratories. Lanes 7 and 8 are longer exposures of Lanes 1 and 2. In Lane 5, the labeled bands, in order of increasing mobility, are acetyl-CoA carboxylase (205 kDa), pyruvate carboxylase (130 kDa) and an unknown protein of 44kDa also observed by Lim et al., *Archives Biochem. and Biophys.*, 258, 259-64 (1987). The band in Lanes 2 and 8 is *E. coli* biotin carboxyl carrier protein (BCCP).

Bio operon derepression was not tested for in yeast since such a system is not known in yeast. The results for bio operon derepression shown in FIG. 21 are for *E. coli* which were assayed for derepression as described in Example 2.

EXAMPLE 7

Purification Of Biotinated Proteins

Low-affinity "monomer avidin" columns were purchased from Sigma Chemical Co. The guanidine treatment used to prepare their material partially and irreversibly denatures avidin and converts most of the high affinity biotin binding sites to sites of lower affinity as described above. The remaining high affinity sites were blocked with biotin to give columns from which bound biotinated proteins were quantitatively eluted with the biotin-containing non-denaturing buffer described in Shenoy et al., *FASEB J.*, 2, 2505-11 (1988).

*E. coli* BMH71-18 was transformed with the vectors carrying either Fusion A or Fusion B and was cultured to express biotinated proteins as described in Example 1. Cell extracts were prepared by disrupting the cells in a French pressure cell. Intact cells and insoluble debris were removed by centrifugation. The supernatants were passed over the monomer avidin columns, which were then washed with the Shenoy et al. buffer minus the biotin to remove unbound materials. The biotinated proteins were eluted from the columns using the Shenoy et al. biotin-containing buffer.

Biotinated fusion proteins were eluted along with endogenous *E. coli* biotin carboxyl carrier protein (BCCP). BCCP was readily separated from the biotinated fusion proteins by gel filtration on Sephacryl S-100 (purchased from Pharmacia LKB Biotechnology) due to the large difference in the molecular weights of the native molecules (about 500,000 daltons for beta-galactosidase versus 44,000 daltons for BCCP).

EXAMPLE 8

Purification of Biotinated Proteins

One hundred milliliter cultures of *E. coli* F'11 recA carrying either plasmid pCY74 encoding fusion B or vector pUR288 encoding beta-galactosidase were grown to early exponential phase in a broth medium, induced with 1 mM IPTG for 3 hours and harvested, as described in Example 1. F'11 recA also carries pBA11, a compatible plasmid that overproduces biotin ligase about ten-fold. See Barker and Campbell, *J. Mol. Biol.*, 146, 469 (1981).

The cells were harvested and disrupted in Z buffer prepared as described in Miller, *Experiments in Molecular Genetics* (Cold Spring Harbor Lab., New York, 1972). The resulting lysate was centrifuged at 48,000×g for 1 hour, and the supernatants (containing about 2 mg protein each) were applied to 0.5 ml columns of monomer avidin linked to Sepharose (prepared as described in Hendrickson et al., *Anal. Biochem.*, 94, 366 (1979)) having an exchangeable biotin binding capacity of 35 nmol/ml Sepharose. The columns were eluted with Z buffer or Z buffer containing 20 mM biotin. Fractions of about 250 μl were collected and assayed for β-galactosidase activity as described in Miller, *Experiments in Molecular Genetics*, and for protein concentration (adsorbance at 280 nm of a twenty-fold dilution).

Figure 22A:
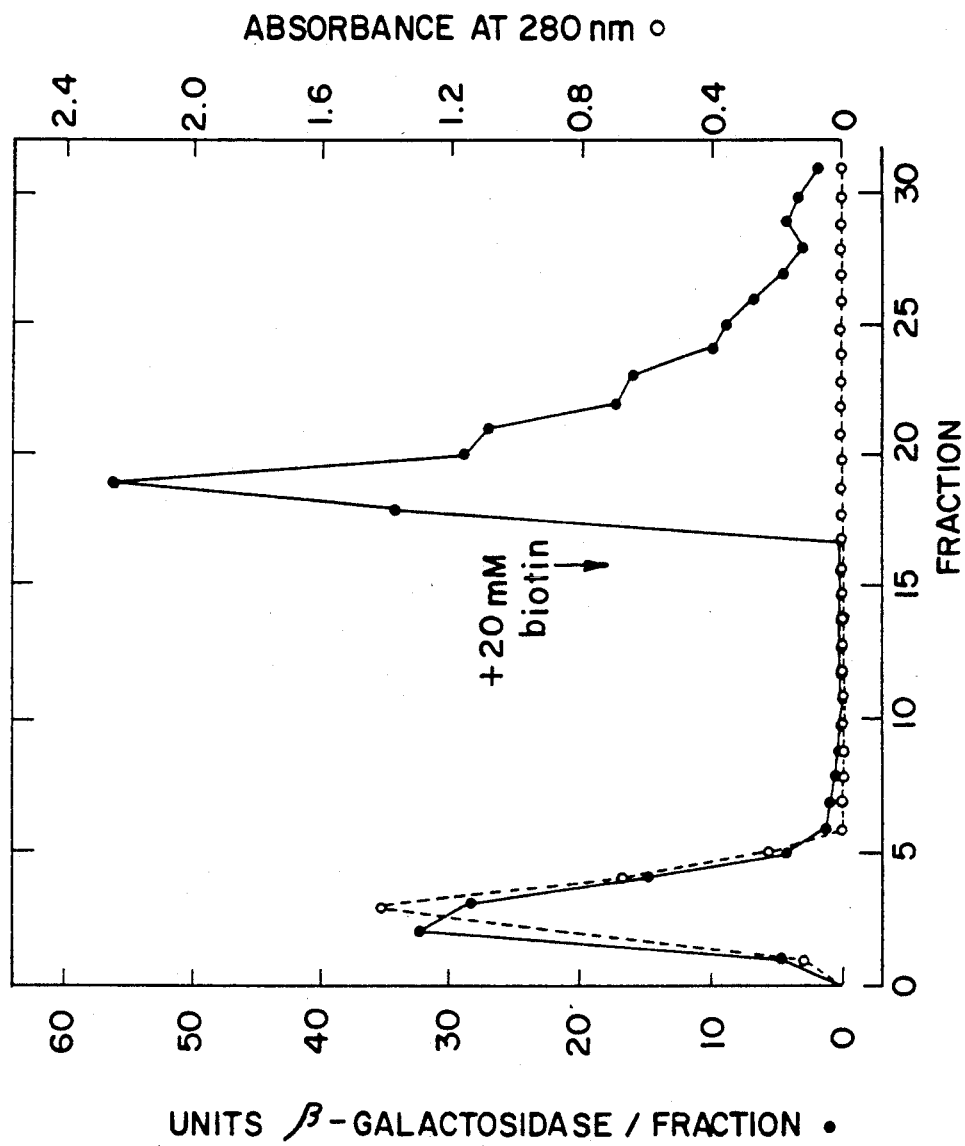
FIG. 22A–C: Graphs of beta-galactosidase activity and protein concentration versus fraction number of materials eluted from monomer avidin columns.
Figure 22B:
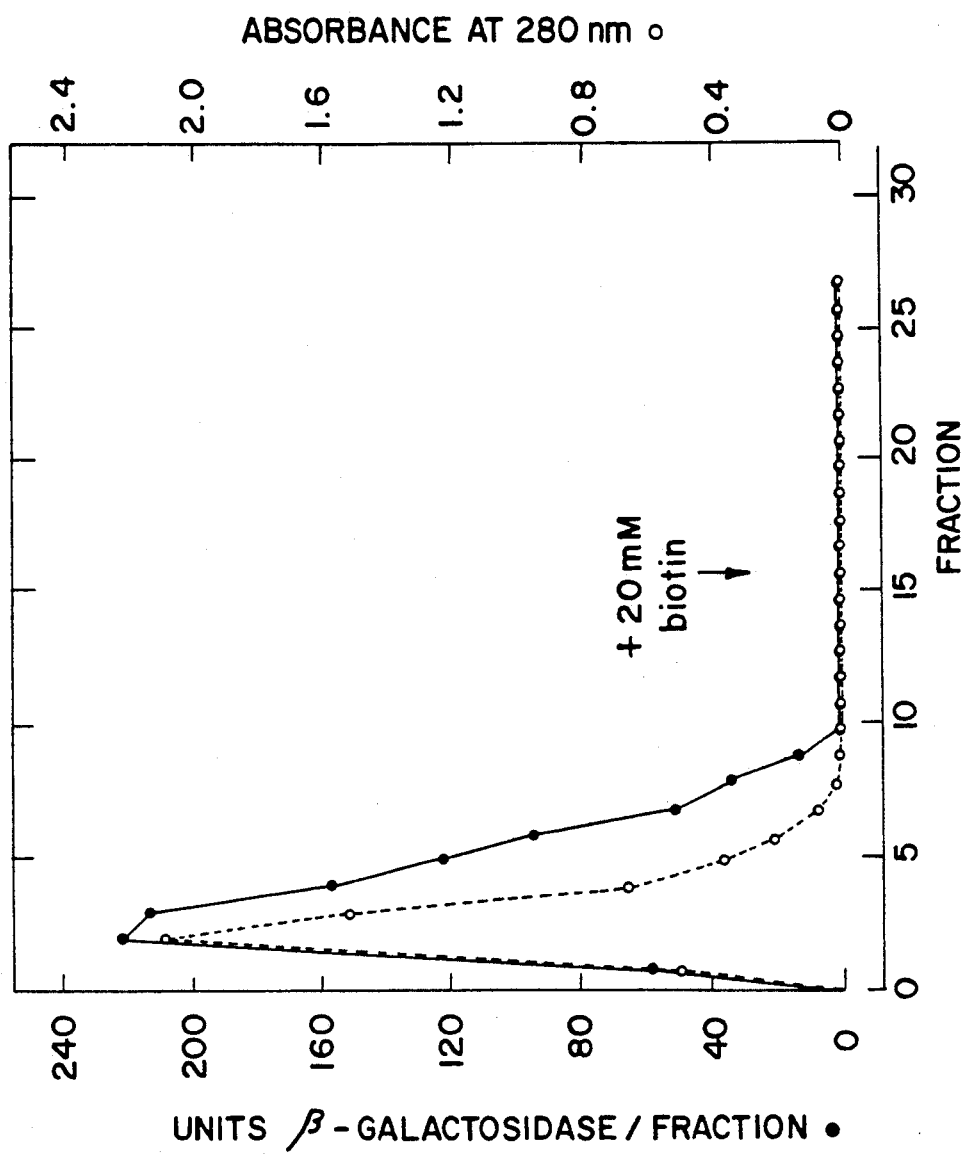
Figure 22C:
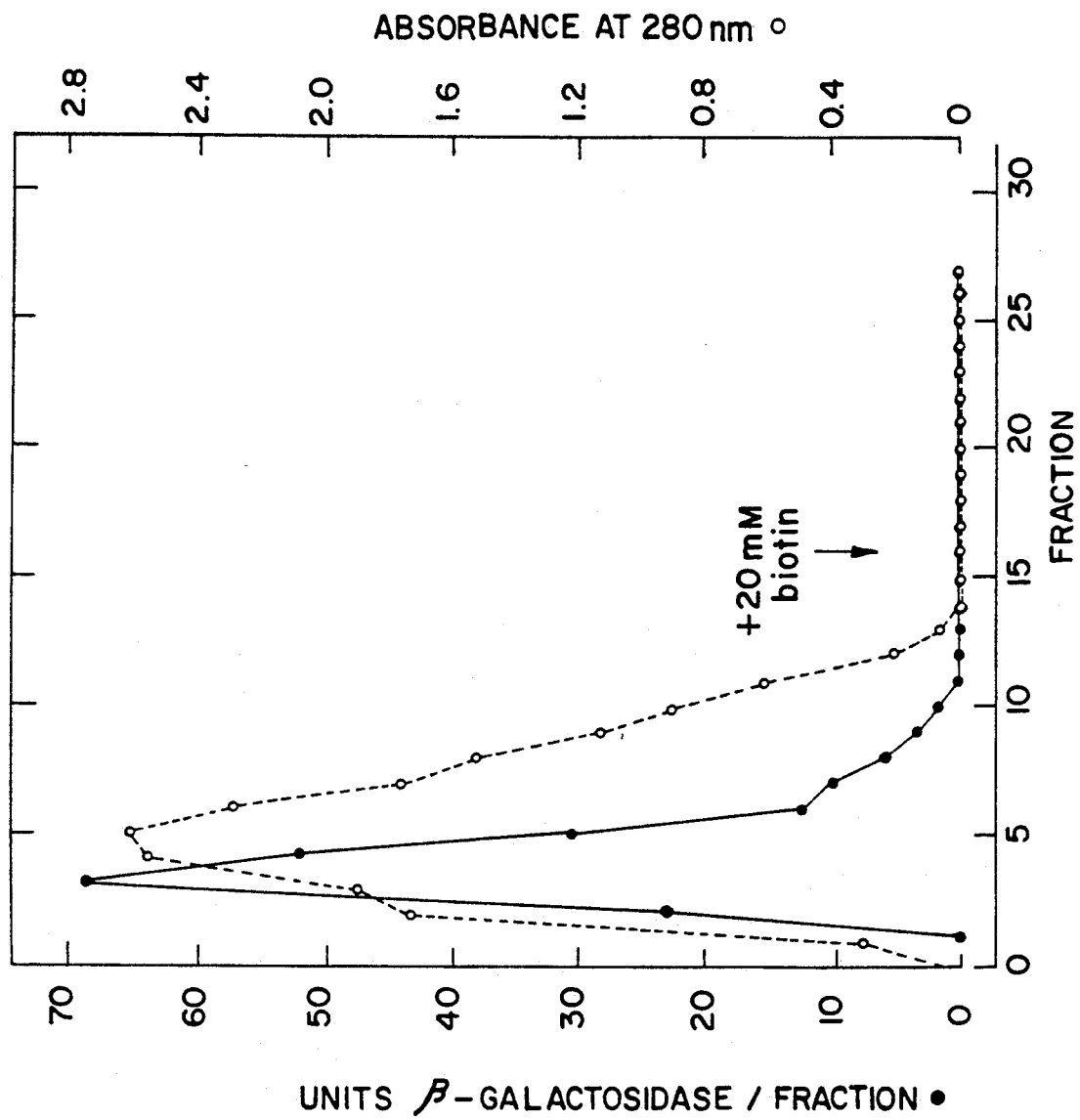

The results are shown in FIGS. 22A-C. FIG. 22A shows a graph of beta-galactosidase activity and protein concentration versus fraction number for a supernatant harvested from cells carrying plasmid pCY74 coding for Fusion B. FIG. 22C is the same as FIG. 22A, except that the column was washed with Z buffer containing 20mM biotin before the supernatant was loaded onto the column. FIG. 22B shows the elution profile for a supernatant harvested from cells carrying pUR288 which produce beta-galactosidase but no fusion protein. As can be seen, the fusion protein is retained on the column and is subsequently eluted by the addition of 20mM biotin.

The purified fusion proteins eluted from the monomer avidin columns were electrophoresed on 8% polyacrylamide gels in the presence of SDS. The gels were stained with Coumassie Blue R.

*E coli* F'11 recA carrying plasmid pCY100 plus either plasmid pCY74 or pUR288 was also cultured, and the protein harvested as described above in this example. The resulting supernatants were applied to monomer avidin columns, and the eluates were electrophoresed on polyacrylamide gels, also as described above.

Plasmid pCY100 was prepared by ligating the BamHI-ScaI fragment of pMBR10 to the large BamHI-EcoRV fragment of pACYC184 as described in Maniatis et al., *Molecular Cloning, A Laboratory Manual* (Cold Spring Harbor Lab., New York 1982). Also see Barker and Campbell, *J. Mol. Biol.*, 146, 469 (1981). Plasmid pMBR10 was the gift of A. Otsuka, and its preparation is described in Buoncristrani and Otsuka, *J. Biol. Chem.*, 263, 1013 (1988). Plasmid pACYC184 was obtained from the ATCC, accession number 37033.

Figure 23:
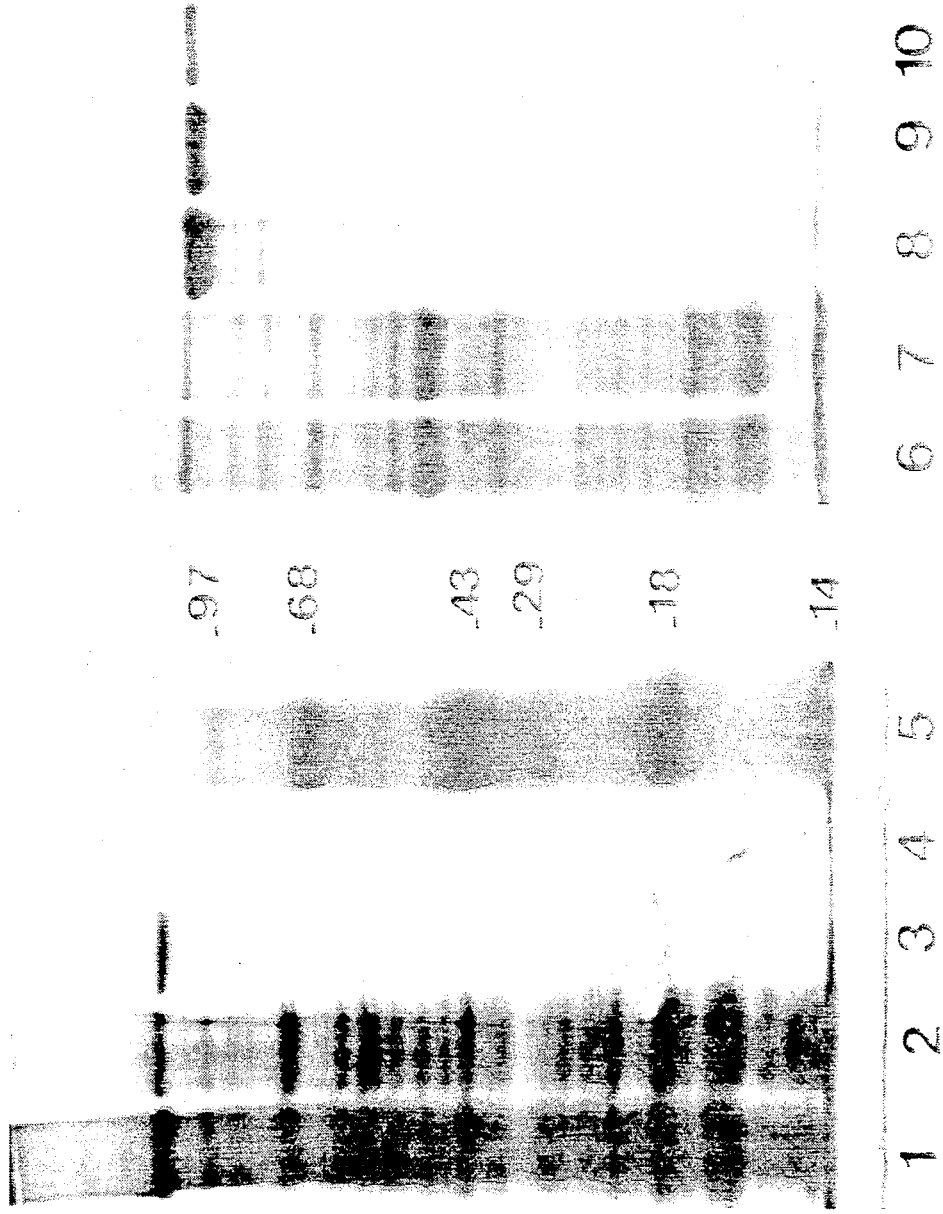
FIG. 23: A stained polyacrylamide gel on which biotinated fusion proteins and controls eluted from monomer avidin columns were electrophoresed.

The results of the electrophoresis are shown in FIG. 23 where Lanes 1-5 contain materials associated with the chromatography of about 20 mg total protein extracted from cells carrying pCY74 encoding fusion B on a 2.5 ml monomer avidin column. A sample of the original supernatant applied to the column was electrophoresed in Lane 1. A sample of the unbound protein (flow-through) was electrophoresed in Lane 2, and a sample of the eluate obtained by elution with 20 mM biotin was electrophoresed in Lane 3. In lane 4 a sample identical to that of lane 3 was electrophoresed, except that the sample was treated with a monoclonal anti-β-galactosidase (from Promega, Madison, Wis.) followed by absorption with protein A-agarose and centrifugation; the resulting supernatant was the material loaded on the gel. The faint bands visible in the lower half of the lane are unabsorbed immunoglobulin chains. Lane 5 contains molecular weight standards (phosphorylase B-97kDa, bovine serum albumin-68kDA, ovalbumin-43kDa, carbonic anhydrase-29kDa, and betalactoglobulin-18.4kDa) purchased from Bethesda Research Laboratories.

Lanes 6-10 contain materials associated with the chromatography of about 5 mg of total protein extracted from cells carrying pCY74 encoding fusion B on a 1.6 ml monomer avidin column. Samples of the original supernatant and unbound protein were electrophoresed in lanes 6 and 7, respectively. A sample of the peak region of the 20 mM biotin eluate was electrophoresed in lane 8, and samples of the tailing regions of the eluate peak were electrophoresed in lanes 9 and 10. The minor bands in lanes 8-10 were removed by absorption with anti-β-galactosidase (data not shown), except for the band of greatest mobility which is a protease-cleaved form of BCCP. See Fall, *Meth. Enzymology*, 62, 390 (1979).

As noted above, some of the host cells carried pCY74 plus either of two birA (biotin ligase overproducing) plasmids. The strain used to produce the materials electrophoresed in lanes 1-5 carried plasmid pCY100 which overproduces the birA protein >100-fold, and the strain used to produce the materials electrophoresed in lanes 6-10 carried pBA11 which overproduced ligase activity about ten-fold.

As can be seen in FIG. 23, elution with biotin produced a single band (lane 3). and this band disappeared after treatment with monoclonal anti-beta-galactosidase (lane 4), showing that the band contained the biotinated fusion protein. By comparing lane 3 with lanes 8-10, it can be seen that the amount of the biotinated fusion protein produced was increased substantially when the host cell carried pCY100 as compared to pBA11.

EXAMPLE 9

Figure 2:
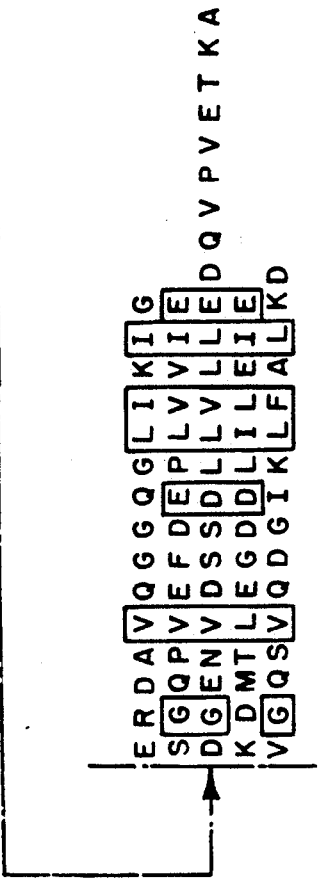
FIG. 2: Sequences of the carboxyl termini of biotinated proteins.

Preparation and Expression of DNA Sequences Encoding Fusion Proteins Having a Site For Post-Translation Biotination Hybrid DNA sequences were prepared comprising DNA coding for a fragment of beta-galactosidase linked in proper reading frame to DNA encoding either the tomato cDNA biotin protein sequence shown in FIG. 2 or the alpha subunit of *Klebsiella pneumoniae* oxalacetate decarboxylase. Each of these two latter DNA sequences encodes a polypeptide having a biotination site. The two DNA sequences were fused so that a fusion protein was encoded having the β-galactosidase fragment at the amino terminal end and having the biotin-acceptor sequences located at the carboxyl terminal end.

Suitable vectors encoding these hybrid DNA sequences were prepared as described below. The vectors were used to transform various strains of *E. coli* (the strains and the method used are described in Example 1). When cultured under conditions permitting expression in the presence of tritiated biotin as described in Example 1, biotinated fusion proteins were produced. Further, when tested for derepression of the bio operon as described in Example 1, derepression was also observed.

A. Preparation of A Vector Comprising Hybrid DNA Sequences Coding for Beta-Galactosidase and Biotinated Tomato Protein A cDNA segment encoding a biotin tomato protein was obtained as an unnamed plasmid from Dr. Neil Hoffman, Department of Biology, University of Pennsylvania, Philadelphia, Pa. The plasmid was derived by SstI digestion of the original lambda Charon 16 phage as described in Hoffman et al., *Nucleic Acid Res.*, 15, 3928 (1987). The phage was isolated from the tomato cDNA bank described in Alexander et al., *Gene*, 31, 79–89 (1984).

The plasmid obtained from Dr. Hoffman was digested with SstI and SalI, and the resulting fragment was ligated to SstI-SalI digested pUR278 (bearing the lacZ gene) to produce plasmid pKR2 encoding Fusion N. Fusion N comprises DNA encoding the N-terminal 651 amino acids of beta-galactosidase fused to the tomato sequence given in FIG. 2. The fusion junction is lacZ residue 651 with PPPPPPPGTV between the lacZ sequence and the tomato sequence of FIG. 2. Plasmid pUR278 was obtained from Professor Muller-Hill, Universitat zu Köln, 5000 Köln 41, FRG. Its preparation and its properties are described in Ruther and Muller-Hill, *The EMBO Journal*, 2, 1791–94 (1983).

B. Preparation of A Vector Comprising Hybrid DNA Sequences Coding for Beta-Galactosidase and Oxalacetate Decarboxylase Alpha Subunit Plasmid pSC3 was obtained from Dr. E. Schwarz, Max-Planck Institut fur Biochemie, Martinsreid, West Germany. Its preparation is described in Laussermair et al., *J. Biol. Chem.*, 264, 14710–15 (1989) and Schwarz et al., *J. Biol. Chem.*, 263, 9640–45 (1988). Plasmid pSC3 encodes the gamma, alpha and part of the beta subunits of *Klebsiella pneumoniae* oxalacetate decarboxylase. Laussermair et al. and Schwarz et al. together disclose the DNA sequence of the alpha, gamma and beta genes.

Plasmid pSC3 was digested with SalI and the resulting 3.2 Kb fragment coding for the alpha subunit was ligated to pHSG398 digested with SalI to form pKR5. The sequence encoding the alpha subunit was then further subcloned by digestion of pKR5 with SalI and BamHI and ligation of the resulting 1.7 Kb fragment to pMTL21 digested with the same enzymes to produce pKR11. Next, plasmid pKR11 was digested with PstI plus BssHII, and the resulting fragment was ligated to pMTL20 digested with PstI plus MluI to give pKR28. Finally, plasmid pKR28 was digested with AatII and ligated to AatII digested pUR278 to give pKR30 carrying Fusion O.

Fusion O comprises DNA encoding 100 residues of the alpha subunit of *Klebsiella pneumoniae* oxalacetate decarboxylase and DNA encoding the N-terminal 210 residues of beta-galactosidase. The amino acid sequence of the 100 residues of the alpha subunit is:

DVSQLTAAAPAPAPAPAPASAPAAAAPAGAGTPVTAPLAGFIWKVLASEGQTVA-
AGEVLLILEAMKMETEIRAAQAGTVRGIAVKAGDAVAVGDTLMTLA.

Plasmid pHSG398 was from obtained the Japanese Cancer Research Resource Bank, Tokyo. Also see Takeshita et al., *Gene*, 61, 63 (1987). Plasmids pMTL20 and pMTL21 were obtained from Dr. S. P. Chambers, PHLC Centre for Applied Microbiology, Salisbury, Wiltshire, England. Their preparation is described in Chambers, Prior, Barstow and Minton, *Gene*, 68 139–149 (1988).

EXAMPLE 10

Preparation and Expression of DNA Sequences Encoding Fusion Proteins Having a Site For Post-Translation Biotination A DNA sequence encoding *E. coli* BCCP was obtained by screening a clone bank with a probe comprising a synthetic oligonucleotide sequence corresponding to residues 17–82 of the amino acid sequence of BCCP reported in Sutton et al., *J. Biol. Chem.*, 252, 3934–3940 (1977). The clone bank was composed of 1.6 Kb HindIII-PstI fragments of the *E. coli* chromosome inserted between the HindIII and PstI sites of phage M13 mp 11 as described in Yanisch-Perron et al., *Gene*, 33, 103–119 (1985). The clone bank may be obtained from Dr. John E. Cronan, Jr., University of Illinois, Champaign, Ill. A HindIII site is located within the coding sequence of BCCP. The DNA sequence of the isolated clone gave a deduced amino acid sequence that exactly matched the Sutton et al. sequence except for D at residue 39 instead of N as reported by Sutton et al.

The double-stranded replicative form of the BCCP clone was digested with HindIII and PstI to release the fragment coding for BCCP, and this fragment was ligated to pTZ18U (carrying an ampicillin resistance gene) digested with the same enzymes. The resulting plasmid, pLS1, was digested with HindIII and ligated to the fragment released from HindIII-digested pCY82. This HindIII fragment codes for chloramphenicol acetyltransferase (CAT).

The resulting mixture was used to transform *E. coli*, and transformants resistant to both ampicillin and chloramphenicol were selected. One of these recombinant plasmids having the CAT gene fused to and in the same orientation as the BCCP gene was digested with NcoI and religated to form pLS2. The effect of this treatment was to remove part of the C-terminal of the CAT gene and part of the N-terminal of BCCP gene and form a new fusion junction between them.

Resultant plasmid pLS2 encodes a fusion protein consisting of the N-terminal 1273 amino acids of the CAT gene fused to the C-terminal 93 amino acids of BCCP (Fusion P). The BCCP sequence is that given in FIG. 2 plus the additional BCCP sequence EAPAAA-GISGHIVRSPMVGT between the CAT sequence and the BCCP sequence given in FIG. 2. Also, the resultant sequence contains D instead of N at BCCP residue 39 as noted above.

Plasmid pTZ18U is available from Pharmacia LKB Biotechnology. Also see Mead et al., *Prot. Engineer*, 1, 67 (1986). The CAT gene of pCY82 is that of transposon Tn9 and is a common component of commercially available cloning vectors such as those available from Pharmacia LKB Biotechnology, Piscataway, New Jersey, Clontech Laboratories, Palo Alto, Calif., Stratagene, Inc., La Jolla, Calif. Also, plasmid pCY82 is available from Dr. John E. Cronan, Jr., University of Illinois, Champaign, Ill.

Plasmid pLS2 was used to transform various strains of *E. coli* (the strains and the method used are described in Example 1). When cultured under conditions permitting expression in the presence of tritiated biotin as described in Example 1, biotinated fusion proteins were produced. When tested for derepression of the bio operon as described in Example 1, derepression was also observed.

EXAMPLE 11

Preparation and Expression of DNA Sequences Encoding Fusion Proteins Having a Site(s) for Lipoic Acid Addition Hybrid DNA sequences were prepared comprising fragments of the *E. coli* aceF gene which encode one or more lipoyl attachment sites and DNA coding for all but the first eight of the amino acids of the β-galactosidase structural gene. The two DNA sequences were fused so that a fusion protein was encoded having the lipoyl-acceptor sequences at the amino terminal end and the β-galactosidase sequence at the carboxyl terminal end.

A. Preparation of Vectors Comprising Fragments of the aceF Gene and the lacZ Structural Gene The aceF gene, which encodes the E2p subunit of *E. coli* pyruvate dehydrogenase, has been cloned and sequenced. See Stephens, Darlison, Lewis and Guest, *Eur. J. Biochem.*, 133, 481-489 (1983). As discussed in the Background section, the amino acid sequence shows three homologous segments of approximately 100 amino acid residues tandemly repeated at the N-terminal half of the E2p polypeptide chain, and each repeat forms a domain which contains a lipoylation site. The repeating segments of the E2p polypeptide chain and of the aceF gene are designated lip1 to lip3 and lipl to lip3, respectively.

Figure 24:
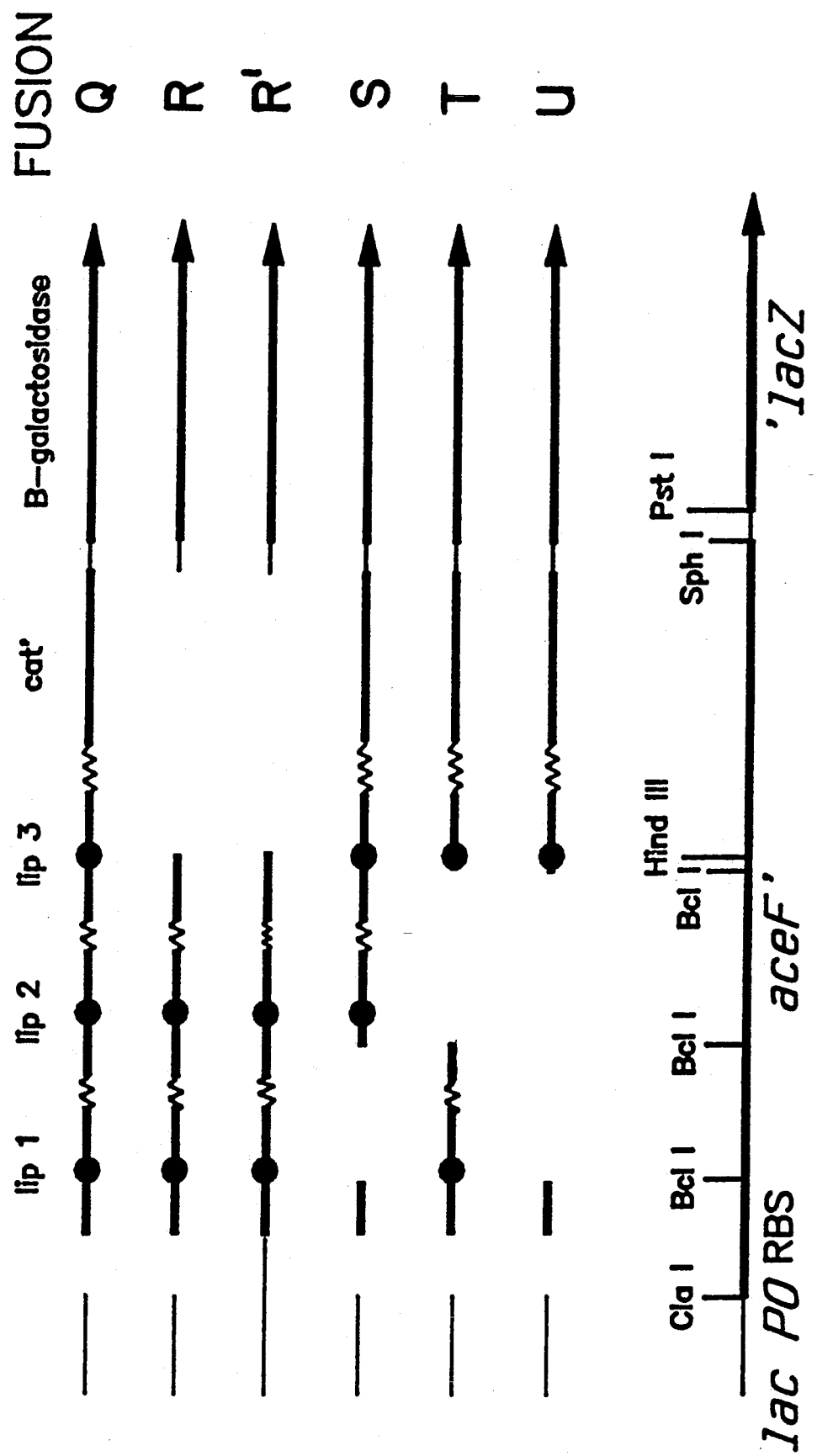
FIG. 24: Illustrates Fusions Q-R.

The aceF gene contains several naturally occurring restriction sites which can be utilized to construct fusions to beta-galactosidase. There are three Bcl I sites at analogous positions in the coding sequence which can be used to generate in-frame deletions equivalent to one or two domains (see FIG. 24).

The starting material for constructing such fusions was plasmid pGS101 which contains the 3' end of the aceF gene and whose preparation is described in Guest, Lewis, Graham, Packman and Perham, *J. Mol. Biol.*, 185, 743-754 (1985). This plasmid was obtained from Professor J. Guest, Department of Microbiology, University of Sheffield, Sheffield S10ZTN, England. In plasmid pGS101, the aceEF coding region is transcribed from the tet promotor of the vector, but possesses its own translation initiation region.

Figure 25:
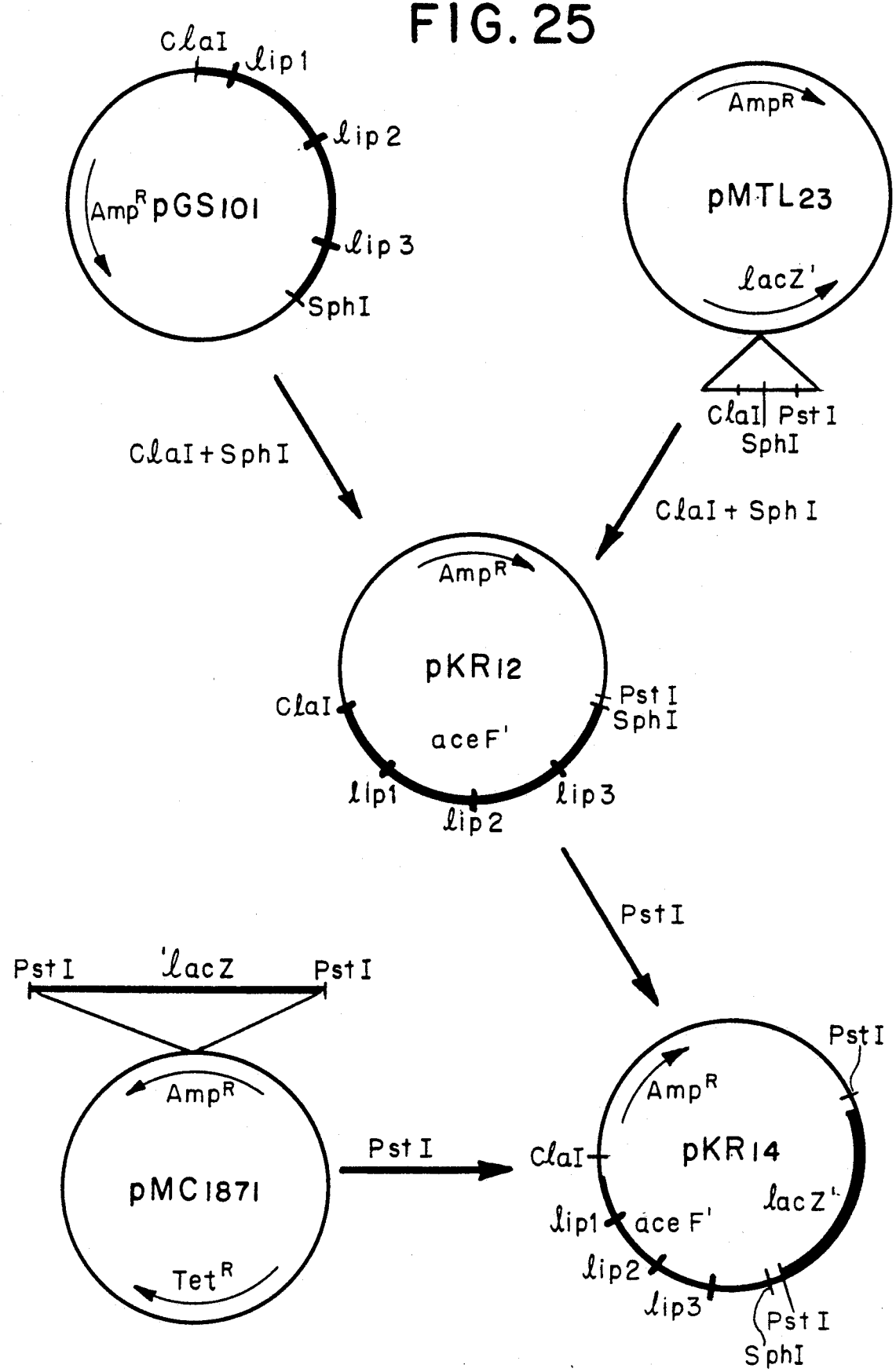
FIG. 25: Illustrates the preparation of vector pKR14.

The lip coding region of pGS101 was subcloned into pMTL23 by ligating the purified 1.2 Kb ClaI/SphI fragment from pGS101 into the ClaI and SphI sites of pMTL23 to produce plasmid pKR12 (see FIG. 25). This step served to place the lip coding region adjacent to a lacZ promotor and also to remove all but 10 codons of the upstream aceE coding region.

Plasmid pMTL23 was the gift of Dr. S. P. Chambers, PHLC Centre for Applied Microbiology, Salisbury, Wiltshire, England. Its preparation is described in Chambers, Prior, Barstow and Minton, *Gene*, 68 139-149 (1988).

Plasmid pKR12, which contains all three lipoyl domains, served as a starting material for additional constructs which contain a subset of the three lipoyl domains. A cassette which contains a DNA sequence encoding all of beta-galactosidase except the first eight amino acids (an active enzyme) was inserted in frame at the 3' end of each lip coding segment of the various constructs. The preparation of these additional hybrid DNA sequences is described below.

1. Preparation of Fusion Q

Fusion Q is a hybrid DNA sequence comprising DNA encoding all three lip domains of E2p linked in the proper reading frame to DNA encoding all but the first eight amino-terminal amino acids of β-galactosidase. See FIG. 24.

Plasmid pKR14 carrying Fusion Q was prepared as shown in FIG. 25. Plasmid pMC1871 was digested with PstI, and the resulting 3 Kb fragment was inserted into the PstI site of pKR12 (preparation described above). Plasmid pMC1871 contains a lacZ cartridge without the control region of the promotor, operator and translation initiation region. See Casadaban, Martinez-Arias, Shapira and Chou. *Methods Enz.*, 100, 293-308 (1983). Plasmid pMC1871 is available from Pharmacia LKB Biotechnology, Piscataway, N.J.

2. Preparation of Fusion R

Fusion R is a hybrid DNA sequence comprising DNA encoding the first two lipoyl domains (lip1 and lip2) and part of third lipoyl domain (lip3) of E2p linked in the proper reading frame to DNA encoding all but the first eight amino acids of β-galactosidase. See FIG. 24.

Figure 26:
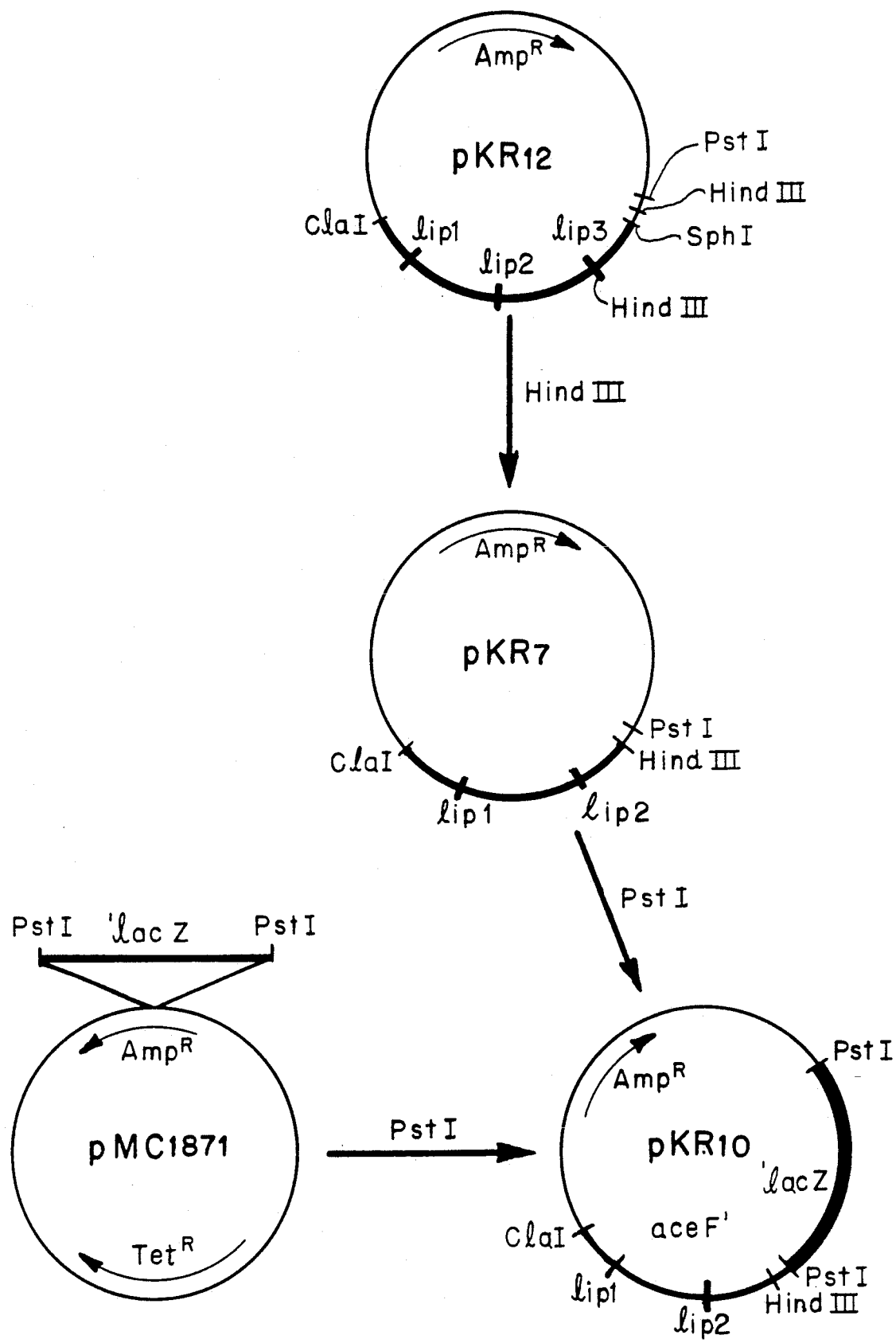
FIG. 26: Illustrates the preparation of vector pKR10.

Plasmid pKR10 carrying Fusion R was prepared as shown in FIG. 26. Plasmid pKR12 carrying lip1, lip2 and lip3 was digested with HindIII and religated. This removed a 450 bp fragment from pKR12 to create plasmid pKR7 (see FIGS. 24 and 26). Plasmid pMC1871 was digested with PstI, and the resulting 3 Kb fragment was inserted into the PstI site of pKR7 to create pKR10.

3. Preparation of Fusions S and T

Fusions S and T both contain DNA coding for hybrid lip domains of E2p fused in the proper reading frame to DNA encoding all but the first eight amino acids of β-galactosidase. Fusion S contains DNA encoding two lip domains consisting of a hybrid lip1-2 domain and lip3. The DNA encoding the lip1-2 domain is formed by fusing in the proper reading frame DNA coding for the amino terminal region of lip1 to DNA encoding the carboxyl terminal region of lip2. See FIG. 24.

Fusion T contains DNA coding for two lip domains consisting of lip1 and a hybrid lip2-3 domain. The DNA encoding the lip2-3 domain is formed by fusing in proper reading frame DNA coding for the amino terminal region of lip2 to DNA encoding the carboxyl terminal region of lip3. See FIG. 24.

Figure 27:
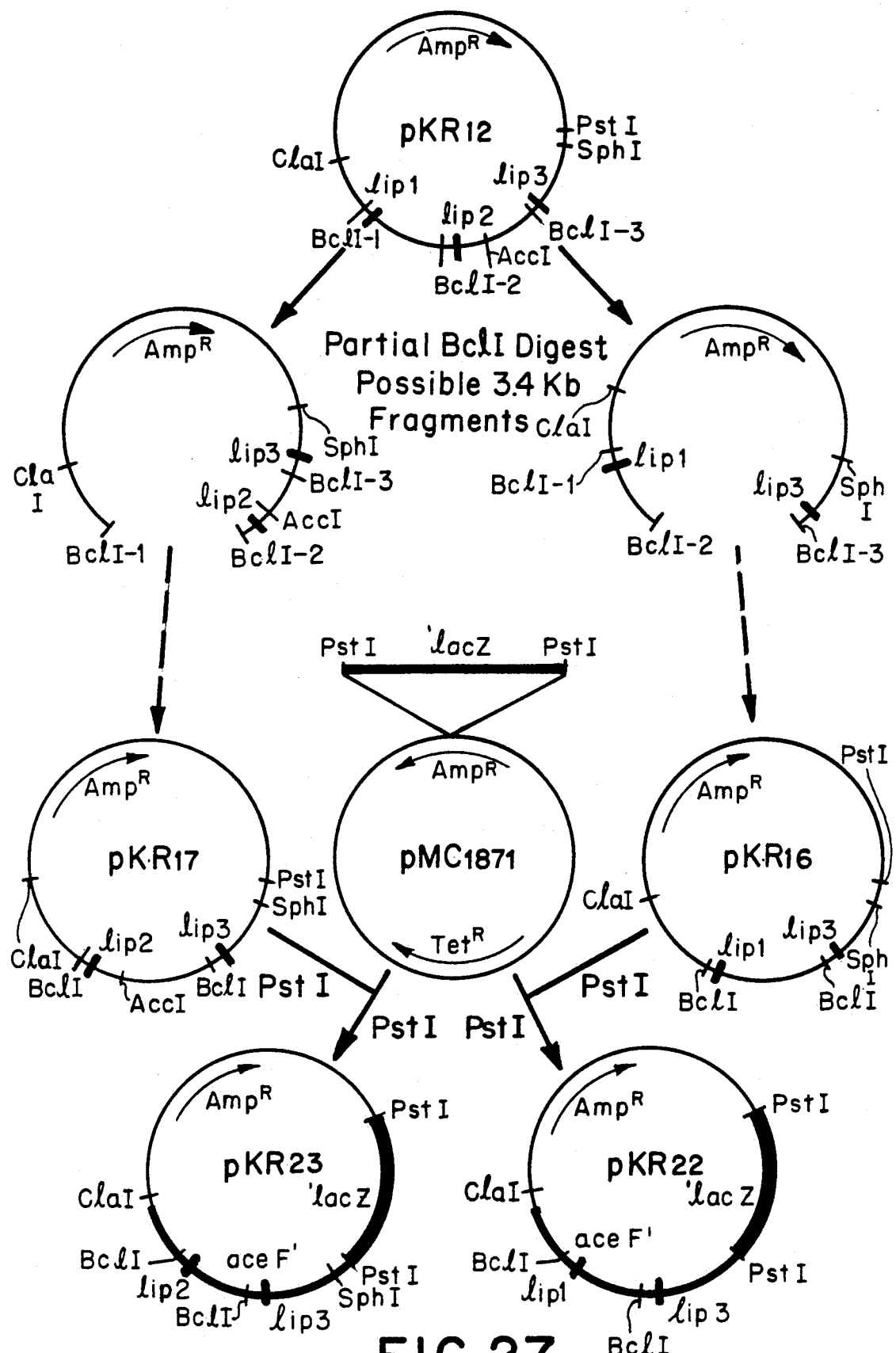
FIG. 27: Illustrates the preparation of vectors pKR22 and pKR23.

Plasmid pKR23 carrying Fusion S and plasmid pKR22 carrying Fusion T were prepared as shown in FIG. 27. First, plasmid pKR12 was partially digested with BclI. The resulting 3.4 Kb fragment which represents either a deletion from BclI-1 (i.e., the BclI site in lip1) to BclI-2 or a deletion from BclI-2 to BclI-3 (see Guest et al., *J. Mol. Biol.*, 185, 743-54 (1985) and FIG. 24) was purified and religated to produce pKR16 and pKR17. The resulting species were distinguished from each other by digesting with AccI since there is an AccI site between BclI-2 and BclI-3 but not between BclI-1 and BclI-2. Next, plasmid pMC1871 was digested with PstI, and the resulting 3 Kb fragment was inserted into the PstI site of pKR16 and pKR17 to form pKR22 and pKR23, respectively.

4. Preparation of Fusion U

Fusion U contains DNA encoding a hybrid lip1-3 domain of E2p fused in the proper reading frame to DNA encoding all but the first eight amino acids of betagalactosidase. The DNA encoding the lip1-3 domain is formed by fusing in the proper reading frame DNA encoding the amino terminal region of lip1 to DNA encoding the carboxyl terminal region of lip3. See FIG. 24.

Plasmid pKR21 carrying Fusion U was prepared as shown in FIG. 28. First, plasmid pKR12 was completely digested with BclI and then religated to form plasmid pKR18. Plasmid pMC1871 was then digested with PstI, and the resulting 3 Kb fragment was inserted into the PstI site of pKR18 to form pKR21.

5. Preparation of Fusion R'

Fusion R' is a hybrid DNA sequence comprising DNA encoding the first two lipoyl domains of E2p and part of the third linked in the proper reading frame to DNA encoding all but the first eight amino acids of beta-galactosidase. See FIG. 24. The coding sequence for Fusion R' is identical to that of Fusion R. The difference is that the translational control region adjacent to the coding sequence of Fusion R' was altered in an attempt to increase expression of Fusion R.

In the native aceEF operon the translational termination site for aceE is approximately five codons upstream of the translational initiation site for aceF. In plasmids pKR10, pKR14, pKR21, pKR22 and pKR23, a small hybrid peptide is formed in addition to the large fusion proteins having sites for post-translational lipoylation. This small peptide is formed as a result of translation of the first 14 codons of the alpha-peptide of $\beta$-galactosidase encoded on the pMTL23 vector plasmid and the first three codons from the cloned insert. This peptide terminates 13 codons before the translational initiation site for aceF.

Figure 29:
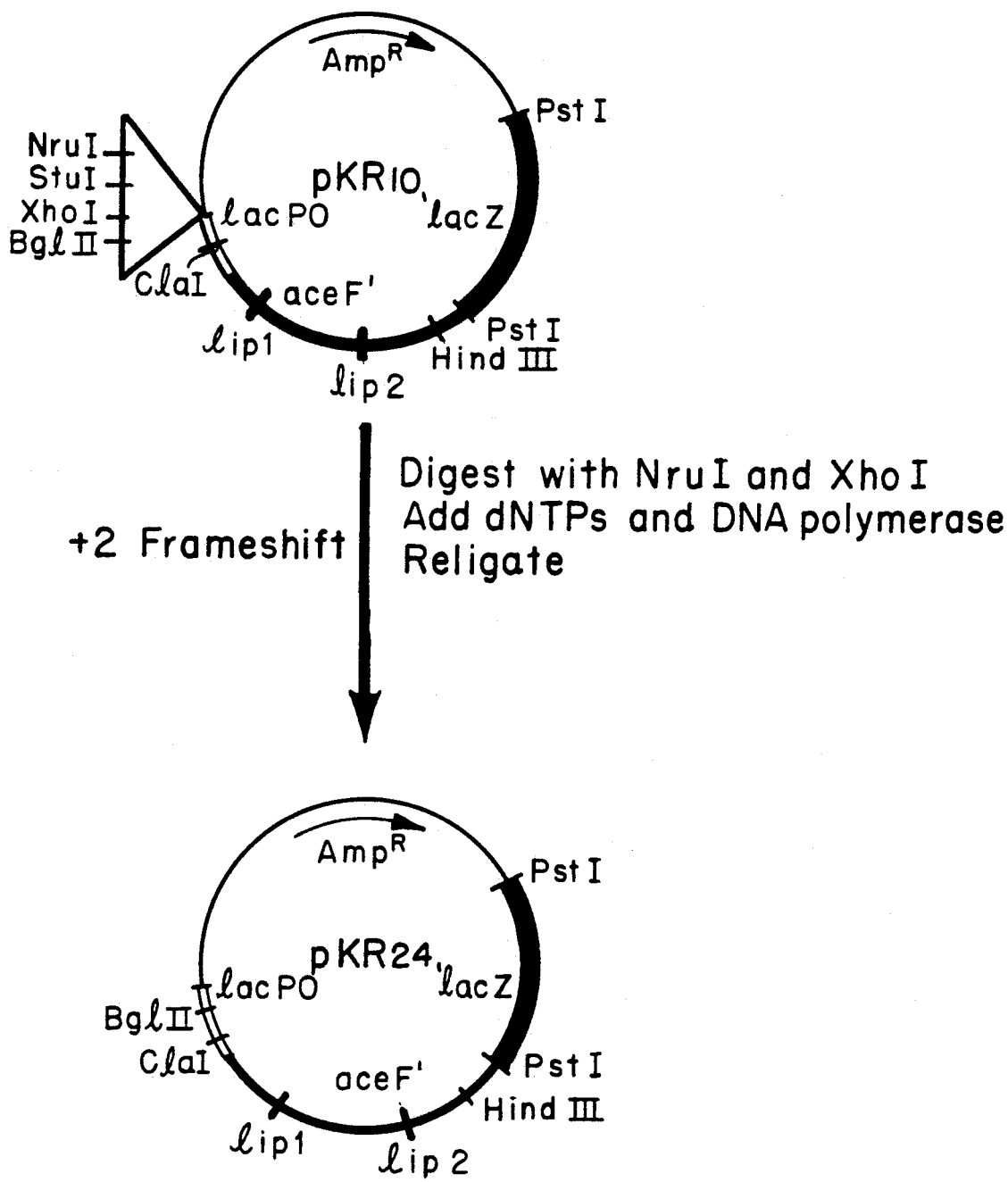
FIG. 29: Illustrates the preparation of vector pKR24.

Plasmid pKR24 carrying Fusion R' was prepared as shown in FIG. 29. First, plasmid pKR10 was digested with XhoI and NruI. The cohesive end was completely filled by incubation with dNTPs and DNA polymerase I (Klenow fragment), and the plasmid religated. This procedure formed a +2 frameshift within the alpha-peptide of $\beta$-galactosidase on the vector plasmid. This frameshift placed the first 14 codons of the alpha-peptide in frame with the last ten codons of aceE. This placed the translational initiation site of Fusion R' five codons downstream of the translational termination site of the small hybrid peptide. This is identical to the translational control region observed at the junction between aceE and aceF in the native operon. This manipulation resulted in a five fold increase in beta-galactosidase activity of Fusion R' over Fusion R.

B. Transformation of Hosts and Expression and Detection of Lipoylated Proteins

1. Transformation

Several E. coli strains were transformed with the vectors prepared as described above carrying Fusions Q-U. The strains used were DH5α, CY487 and CY565. Transformation was performed as described in Example 1.

Strain DH5α was described in Example 1. Strain CY487 was prepared by transduction of strain JM103 to chloramphenicol resistance with P1 vir grown on strain GM2199 as described in Marinus, Carrway, Frey, Brown and Arraj, *Mol. Gen. Genetics,* 192, 288-289 (1983). Strain CY487 possesses a dcm phenotype which allows plasmids to be digested with BclI.

Strain CY565 was obtained by curing strain NK5830 of the F'lacI$^Q$ L8 proAB episome. This strain has a deletion of the chromosomal lactose operon.

Strains JM103, GM2199 and NK5830 were obtained from the Coli Genetic Stock Center, Yale University, New Haven, Conn.

2. Synthesis of $^{35}S$ Lipoic Acid $^{35}S$-lipoic acid was synthesized as described for the non-radioactive compound by Elliott, Steele and Johnson, *Tetrahedron Letters,* 26, 3535-38 (1983). The di-(t-butyl dimethylsilyl) derivative of (6S)-isopropyl-6,8-dihydrooxyoctanoate, a side-product of the published synthesis, was the gift of W. S. Johnson, Department of Chemistry, Stanford University, Stanford, Calif. The t-butyl dimethylsilyl moieties were removed to generate isopropyl-6,8-dihydroxyoctanoate by treatment with Dowex 50X-8 ion-exchange resin (H$^+$ form) as described by Corey, Ponder and Uhrich, *Tetrahedron Letters* 21, 137-140 (1980). The remainder of the synthesis was as described by Elliott et al., supra, except for the substitution of $^{35}S$ elemental sulfur (Amersham Corp., Arlington Heights, Ill.) for a portion of the non-radioactive sulfur. The final product had a specific activity of 0.8 Ci/mmol when quantitated by bioassay with *E. coli* strain JRG26 as described in Herbert and Guest, *Methods in Enzymology,* 18, 269-272 (1970). *E. coli* JRG26 (also called W1485 lip-2) was obtained from the Coli Genetic Stock Center, Yale University, New Haven, Conn.

3. Assay for Radioactively-Labeled Lipoylated Proteins

*E. Coli* strains DH5α, CY487 and CY565 transformed with plasmids pKR10, pKR14, pKR21, pKR22, pKR23 and pKR24 were cultured with $^{35}S$ lipoic acid to label the fusion proteins. The bacteria were cultured at 37° C. to $1-2 \times 10^9$ cells/ml in minimal medium E containing 0.4% glycerol, 1 μg/ml thiamine, 1 mM cysteine, 0.4% vitamin free casein hydrolysate, 8 ng of $^{35}S$-lipoic acid and appropriate antibiotics to select for plasmid maintenance.

After overnight culture, 0.1 ml aliquots containing $1-2 \times 10^8$ cells were placed in test tubes containing 1.0 ml of the same medium supplemented with 1 mM isopropyl-thio-galactoside. The cells were cultured for 2-3 hrs to obtain expression of the fusion proteins. The cells were harvested and lysed in a solution of 0.1M Tris-HCl, pH 7.5, containing 8M urea and 1% SDS. The cell extracts were separated on a 7.5% polyacrylamide gel run in the discontinuous mode in the presence of SDS. The gels were fluorographed by soaking them in Enlightening (purchased from New England Nuclear, Boston, Mass.) and then used to expose preflashed film.

Figure 30:
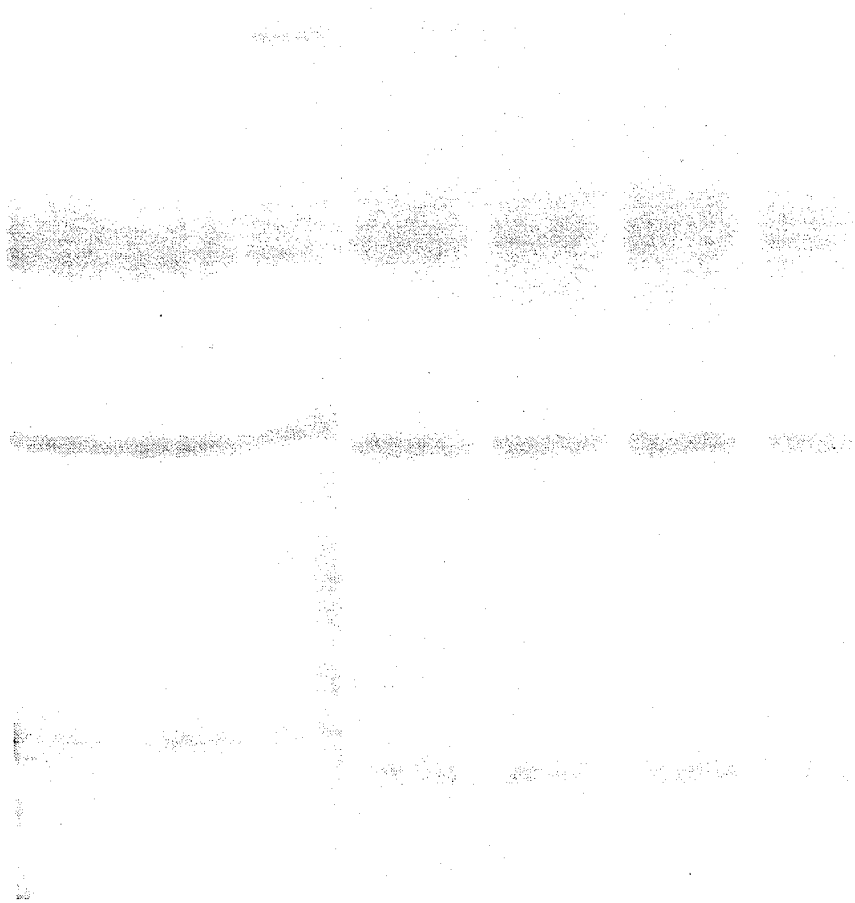
FIG. 30: A typical fluorograph of lipoylated proteins prepared using a $^{35}$S-labeling procedure.

FIG. 30 shows a typical fluorograph obtained using the $^{35}S$-labeling procedure described above. Lane 1 contains no fusion protein; Lane 2 contains an extract from cells carrying Fusion R; Lane 3 contains an extract from cells carrying Fusion R'; Lane 4 contains an extract from cells carrying Fusion Q; Lane 5 contains an extract from cells carrying Fusion S; Lane 6 contains an extract from cells carrying Fusion T; and Lane 7 contains an extract from cells carrying Fusion U.

In all lanes of FIG. 30, bands are found at 30 kDa, 56 kDa and 80 kDa. The bands at 56 kDa and 80 kDa have been positively identified as the dihydrolipoyl transacetylase subunits (E2) of pyruvate dehydrogenase and α-ketoglutarate dehydrogenase, respectively. The band at 30 kDa has been identified as a lipoylated protein which is involved in the glycine cleavage system.

The faint bands appearing at approximately 150 kDa in all lanes except Lane 1 represent the lipoylated fusion proteins. Fusion R' is darker than Fusion R, showing the increased expression of Fusion R' as compared to that of Fusion R (compare Lanes 2 and 3).

More efficient labelling of fusion proteins is expected when fusions are placed in a strain harboring deletions in aceF, sucB and the gene encoding the lipoylated protein involved in the glycine cleavage system. A strain carrying such deletions can be supplemented with acetate and succinate so that a fusion introduced into this strain would become the only lipoylated protein present.

In FIG. 31, Lane 1 contains an extract of *E. coli* JRG26 which is a lipoate auxotroph; Lane 2 contains an extract of TD3K01 which possesses a deletion which extends into sucB; and Lane 3 contains an extract of *E. coli* CY265 which possesses a deletion which extends through aceF. The genes aceF and sucB encode the E2 subunits of pyruvate dehydrogenase and alphaketoglutarate dehydrogenase, respectively.

Strain CY265 was obtained from the Coli Genetic Stock Center, Yale University, New Haven, Conn., and strain TD3K01 was obtained from Dr. John Guest, Dept. Microbiology, University of Sheffield, Sheffield S10ZTN, England. All strains were cultured as described above, but with proper supplementation.

As can be seen in FIG. 31, strain CY265 does not produce E2p, and strain TD3K01 does not produce E2o. The absence of the production of these proteins should make it possible to obtain larger amounts of lipoated fusion proteins using such bacteria.

EXAMPLE 12

Purification of Lipoylated Proteins

Para-aminophenylarsine oxide (PAPAO) was purchased from Aldrich Chemical Co., Milwaukee, Wis. PAPAO-Sepharose was prepared as described in Hannestad, Lundqvist and Sorbo, *Anal Biochem.*, 126, 200–204 (1982). PAPAO-Sepharose was shown by Hannestad et al. to have a higher affinity for 1,2-dithiols (such as 2,3-dimercapto-1-propanol (DMP)) and 1,3-dithiols (such as dihydrolipoic acid (DHLA)) than monothiols (such as cysteine) and 1,4-dithiols (such as dithiothreitol (DTT)).

*E. coli* strain CY565 (described in Example 11) was transformed with pKR10 which carries Fusion R and was cultured to express lipoylated proteins as described in Example 11. A cell extract was prepared by disrupting the cells in a French pressure cell. Intact cells and cellular debris were removed by centrifugation.

The supernatant fraction was reduced with 50 μM DTT in 0.1M sodium phosphate, pH 7.0. The reduced supernatant fraction was applied to a PAPAO-Sepharose column and allowed to absorb for 1 hour at 4° C. The column was then washed with about 20 column volumes of 0.1M sodium phosphate buffer, pH 8.5, containing 0.01M cysteine and 0.5M NaCl. The cysteine served to remove any weakly bound monothiols or dithiols from the column.

Lipoylated proteins were eluted from the column with either 50 μM DTT, DHLA, 2,3-dimercapto-2-propanol (DMP) or 2,3-dimercapto-2-propane sulfonic acid (DMPSO$_3$) in 0.1M sodium phosphate buffer, pH 8.0. The DHLA was prepared by reduction of lipoic acid with sodium borohydride as described in Hannestad et al., supra.

DMP, lipoic acid and DMPSO$_3$ were purchased from Aldrich Chemical Co., Milwaukee, Wis. Sepharose 6B, cysteine and DTT were obtained from Sigma Chemical Co., St. Louis, Mo.

Figure 32:
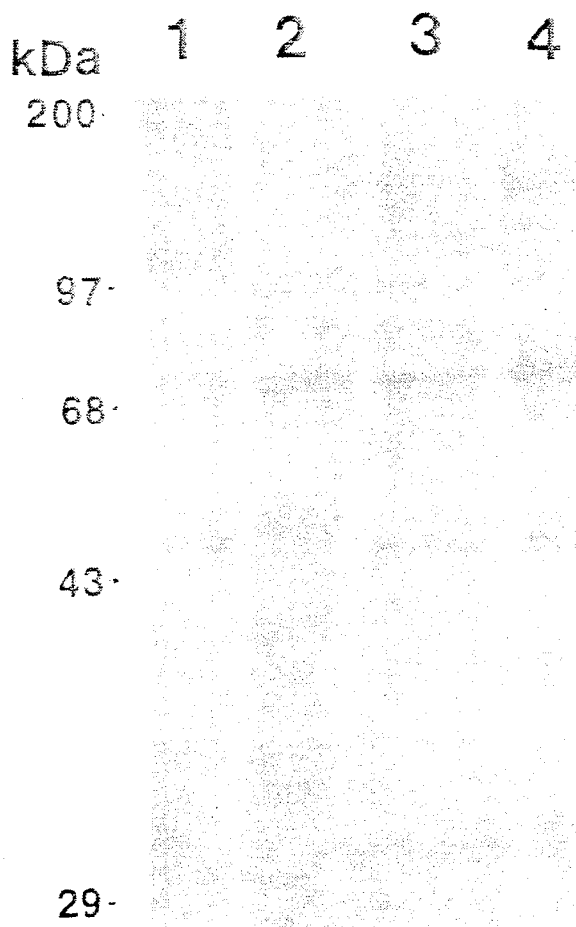
FIG. 32: A stained polyacrylamide gel on which lipoylated proteins were electrophoresed.

Lipoylated proteins eluted from the columns were electrophoresed on 7.5% polyacrylamide gels in the presence of SDS. FIG. 32 shows an SDS-polyacrylamide gel stained with Fast Stain (purchased from Zoion Research Inc., Alston, Mass.), of lipoylated proteins eluted from PAPAO-Sepharose. In FIG. 32, Lane 1 contains proteins eluted from a column loaded with an extract of a prototrophic strain that carries a chromosomal copy of lacZ, and Lanes 2-4 contain proteins eluted from columns loaded with extracts of strain CY565 carrying Fusion R (pKR10). Lane 2 contains proteins eluted with DTT, Lane 3 contains proteins eluted with DHLA, and Lane 4 contains proteins eluted with DMPSO$_3$. In every lane, the bands appearing at 56 kDa and 82 kDa are E2o and E2p, respectively. The band at 116 kDa in Lane 1 is native beta-galactosidase. The band appearing at 155 kDa in Lanes 3 and 4 is the fusion protein produced by Fusion R.

Elution of the fusion protein from the column was also monitored by assay of beta-galactosidase activity (assay described in Example 8). The results are shown in Table II below. As can be seen from the data in Table II, DMPSO$_3$ is the best eluant tested.

TABLE II

ELUTION OF FUSION B FROM PAPAO-SEPHAROSE WITH VARIOUS DITHIOLS

| Dithiol | % Fusion Protein Eluted |
|---|---|
| DTT | 11 |
| DHLA | 50 |
| DMP | 55 |
| DMPSO$_3$ | 98 |

EXAMPLE 13

Secretion Of A Biotinated Fusion Protein

A hybrid DNA sequence was prepared comprising DNA coding for a fragment of *E. coli* BCCP linked in proper reading frame to DNA coding for a fragment of pre-beta-lactamase. The BCCP DNA sequence encodes a polypeptide having a biotination site, and the prebeta-lactamase DNA encodes a polypeptide having a signal sequence which provides for secretion of beta-lactamose. The two DNA sequences were fused so that a fusion protein was encoded having the pre-beta-lactamase fragment at the amino terminal and having the BCCP fragment at the carboxyl terminal end.

Figure 33:
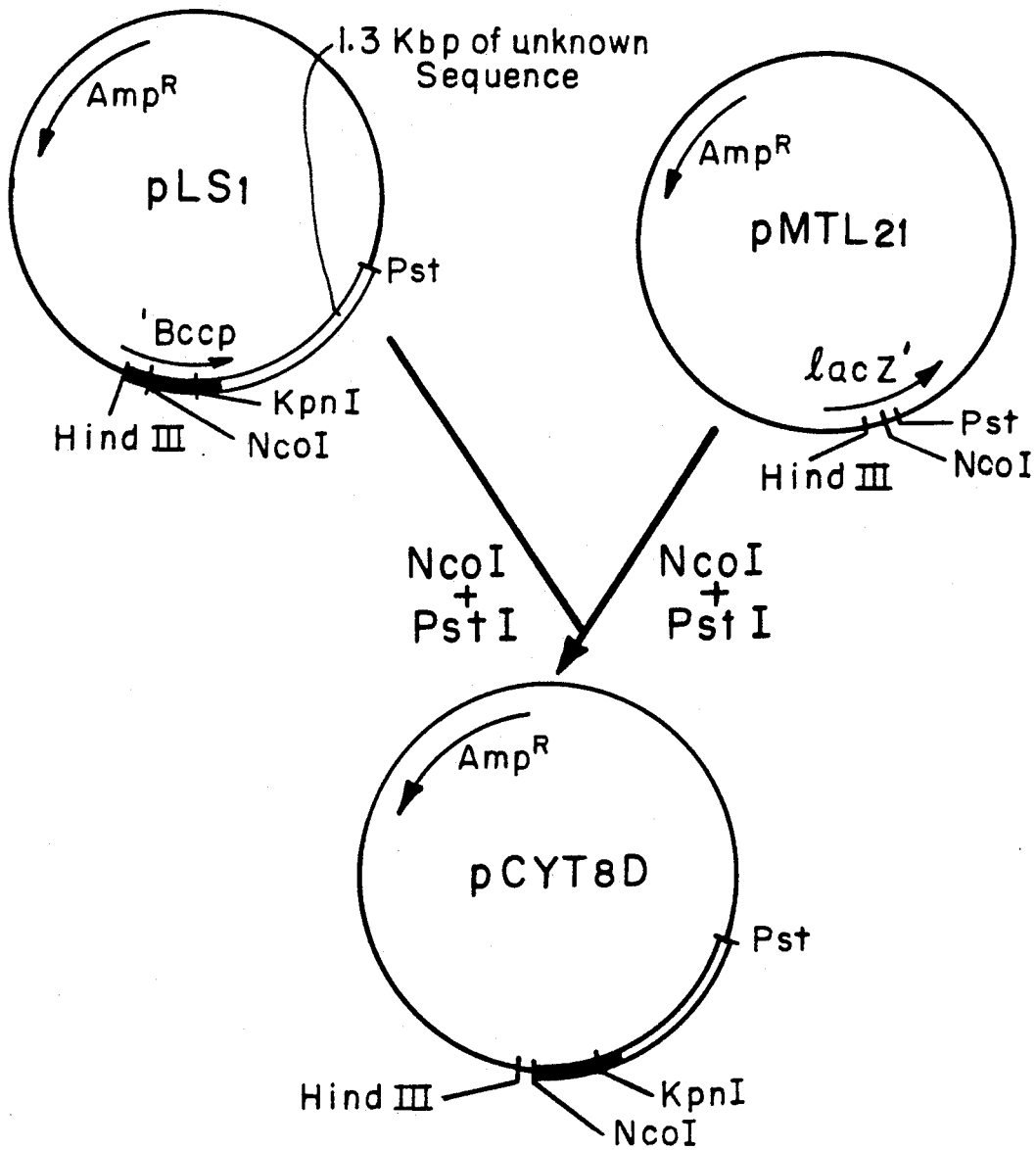
FIG. 33: Illustrates the preparation of vector pCYT8D.

Plasmids pLS1 and pMTL21 were digested with PstI and NcoI and ligated to give pCYT8D as shown in FIG. 33. The preparation of plasmid pLSI is described in Example 10, and plasmid pMTL21 was obtained from Dr. S. P. Chambers as set forth in Example 9.

Plasmid pCY151 was prepared by replacing the KpnI-PstI segment of plasmid pCYT8D with a segment of synthetic DNA that encodes the C-terminal 23 amino acids of *E. coli* BCCP. This manipulation eliminated the approximately 1.3 Kbp of DNA of unknown sequence located downstream of the BCCP coding sequence and, due to the degeneracy of the genetic code, allowed introduction of two new six-base restriction sites into the BCCP gene (CfrlOI and EcoRI), together with a BclI site spanning the translation termination codon and a SalI site located immediately downstream of the termination codon.

The synthetic DNA fragment was assembled from four synthetic oligonucleotides of 41, 33, 37, and 45 bases (oligos A to D respectively) as described in Cronan, Narasimhan, and Rawlings, *Gene,* 70, 161-169 (1988). The four oligonucleotides had the following sequences:

(A) CGTTAAAGCTATCCTTGTTGTT-GAATCTGGTCAGCCGGTTGAAT
(B) TCGACGAACCGCTTGTTGTTATCGAAT-GATCAG
(C) CATGGCAATTTCGATAGGAACAACT-TAGACCAGTCGG
(D) CCAACTTAAGCTGCTTGG-CGAACAACAATAGCTTACTAGTCAGCT

See FIG. 2 for the amino acid sequence of BCCP. The assembled synthetic DNA was designed to give the 3' protruding single stranded ends of KpnI and the 5' protruding ends of SalI, the KpnI ends lying within the BCCP coding sequence.

Figure 34:
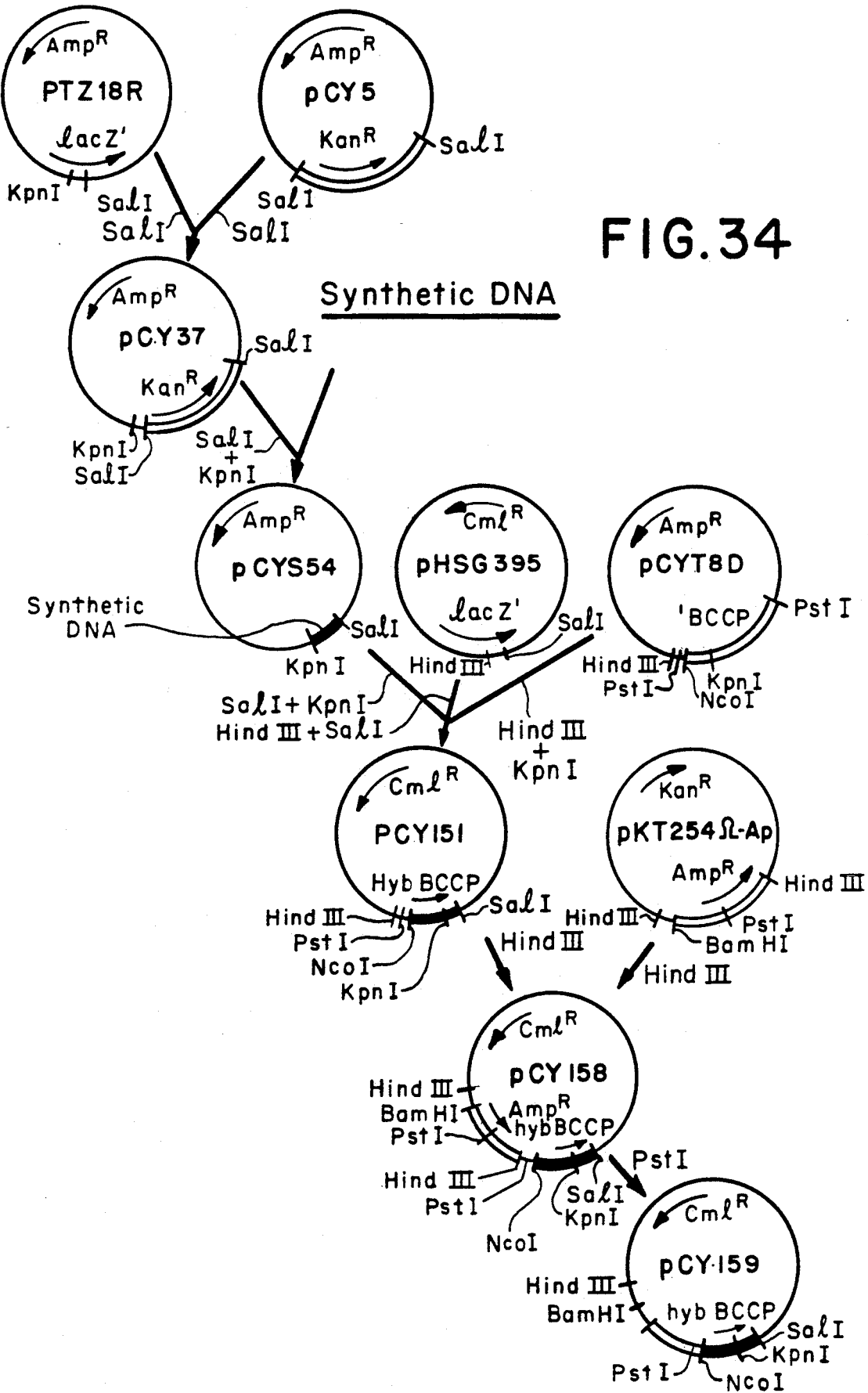
FIG. 34: Illustrates the preparation of vector pCY159.

The assembled synthetic DNA was then ligated to plasmid pCY37 digested with KpnI and SalI as shown in FIG. 34. The resulting transformants were screened for plasmids containing the expected restriction sites, and one of these, pCYS54, was shown to contain the expected sequence by DNA sequence analysis.

Plasmid pCY37 was constructed by insertion of the Kan ® gene of pCY5 into pTZ18R as shown in FIG. 34. Plasmid pCY5 was prepared as described in Example 3. Plasmid pTZ18R was obtained from Pharmacia LKB Biotechnology, Piscataway, N.J.

Plasmid pCY151 was constructed by digestion of pCYT8D with HindIII and KpnI and of pCYS54 with KpnI and SalI. These digests were combined and ligated to pHSG395 digested with HindIII and SalI to give pCY151 as shown in FIG. 34. Plasmid pCY151 therefore contained a BCCP gene fragment composed of the NcoI to KpnI segment of the natural BCCP gene and the KpnI to SalI segment originating from the synthetic DNA. Plasmid pHSG395 was obtained from the Japanese Cancer Research Resources Bank, Tokyo.

To fuse the beta-lactamase sequence to the BCCP sequence, the beta-lactamase gene of pKT254Ω-Ap (prepared as described in Fellay, Frey, and Krisch, *Gene,* 52, 147-154 (1987)) was excised with HindIII and ligated to HindIII-digested pCY151 to give pCY158 (see FIG. 34). Plasmid pCY158 was then digested with PstI and recircularized by ligation to give pCY159. Plasmid pCY159 encodes a fusion protein consisting of the N-terminal 182 amino acids of pre-beta-lactamase fused to the C-terminal 87 amino acids of BCCP. Three amino acids (L, G, T) encoded by the pMTL21 polylinker sequences are present at the junction of the two polypeptides.

It should be noted that the beta-lactamase gene used is the same as that found in pBR322 which can be obtained from ATCC, accession number 31344. Plasmid pKT254Ω-Ap was obtained from Dr. J. Frey, Institute of Veterinary Bacteriology, CH-3012, Switzerland.

Plasmid pCY159 was transformed into four different *E. coli* K-12 strains obtained from Dr. K. Strauch and Professor J. Beckwith, Department of Microbiology, Harvard medical School. Two of these strains (KS474 and KS476) lack a major protease (DegP) normally present in the periplasmic space. Two strains (KS303 and KS474) lack the major outer membrane lipoprotein. Such lpp⁻ strains have an altered outer membrane through which periplasmic proteins can escape to the extracellular milieu (see Suzuki, Nishimura, Yasuda, Nishimura, Yamada, and Hirota, *Molecular and General Genetics,* 167, 1-9 (1978)).

The strains and relevant genotypes used are:

| Strain | Genotype | Designation of Derivative Carrying pCY159 |
|---|---|---|
| KS272 | wild type | CY742 |
| KS303 | lpp-5508 | CY743 |
| KS474 | degP41 | CY744 |
| KS476 | lpp-5508, degP41 | CY745 |

Strains KS272, KS303, and KS474 are described in Strauch, Johnson, Beckwith, *J. Bacteriol.,* 171, 2689-2697 (1989) and Strauch and Beckwith, *Proc. Nat'l Acad. Sci. U.S.A.,* 85, 1576-80 (1988). Strain KS476 was constructed from KS474 and KS303 by K. Strauch.

Strains CY742 to 745 were grown and labeled with ³H-biotin as described in Example 1. The cells were collected by centrifugation (12,000×g from 10 min), the pellets were washed with 10 mM tris-HCl, pH 8.0, and then prepared for SDS polyacrylamide gel electrophoresis. The culture supernatants from the centrifugation steps were retained and any proteins present were collected by precipitation with trichloroacetic acid and also analyzed by gel electrophoresis.

The results of the gel electrophoresis showed that the culture supernatants from the degP⁺ strains (KS272 and KS303) did not contain a biotinated protein of the molecular weight (about 30,000) expected for the beta-lactamase-BCCP fusion protein. Instead, a biotin-labeled protein of about 14,000 Da was observed. In contrast, supernatants from both depP⁻ strains which lack the DegP protease (KS474 and KS476) contained a biotinated protein of the expected size of the fusion protein.

From these data it is clear that the betalactamase-BCCP fusion is a substrate for the DegP protease. In cells containing DegP protease, the fusion protein was cleaved close to the fusion junction, whereas no cleavage product was seen in cells lacking DegP protease. DegP protease functions only in the periplasm, and loss of this protease fails to stabilize fusion proteins located in the cytoplasm (see Strauch and Beckwith, *Proc. Natl. Acad. Sci. U.S.A.,* 85, 1576-1580 (1988)). It, therefore, follows that the beta-lactamase-BCCP fusion must be secreted through the *E. coli* inner membrane to the periplasm, the location of the DegP protease. Consistent with this interpretation, culture supernatants of the lpp⁻ deqP⁻ strain KS476 contained a considerable amount of biotinated fusion protein, whereas no fusion protein was observed in the culture supernatants of the 1 pp⁺ strains (KS272, KS474). Thus, as expected from the properties of the 1 pp mutation, biotinated fusion proteins leaked from the periplasm of strain KS476 into the culture medium. Roughly half of the total biotinated fusion protein of strain KS476 was found in the medium; the remainder was cell-associated. Moreover, although no 30,000 Da biotinated protein was observed in cell pellets of strain KS303, some of this protein species was found in the culture medium (about 20% of the amount seen in the KS476 medium). Thus, in an lpp⁻ strain, a portion of the fusion protein apparently can escape the DegP protease as a result of leakage from the periplasm into the culture medium. It should be noted that the degP protease has recently been purified and shown to be an endoprotease (see Lipinska, Zylicz, Georgopoulas, *J. Bacteriol.*, 172, 1791–1797 (1990)).

I claim:

1. A transformed host cell into which DNA has been introduced, or progeny of said transformed host cell, the introduced DNA comprising:
   (a) DNA coding for a fusion protein comprising:
      (i) a first DNA sequence which codes for a protein or polypeptide having an amino acid sequence that allows for post-translation biotination of the fusion protein; and
      (ii) a second DNA sequences joined end to end with the first DNA sequence and in the same reading frame, the second DNA sequence encoding a selected protein or polypeptide; and
   (b) DNA coding for biotin ligase;
   the DNA coding for the fusion protein and the DNA coding for biotin ligase being operatively linked to expression control sequences.

2. The host cell of claim 1 wherein the DNA coding for the fusion protein further comprises a third DNA sequence which codes for a cleavage site, the third DNA sequence being located between the first and second DNA sequences, all three DNA sequences being in the same reading frame.

3. The host cell of claim 11 wherein the first DNA sequence codes for the 1.3S subunit of *Propionibacterium shermanii* transcarboxylase, tomato biotin protein, the alpha subunit of *Klebsiella pneumoniae* oxalacetate decarboxylase, *Escherichia coli* biotin carboxyl carrier protein or fragments of these proteins that allow for post-translation biotination of the fusion protein.

4. The host cell of claim 3 wherein the first DNA sequence codes for the final 75 amino acids of the 1.3S subunit of *Propionibacterium shermanii* transcarboxylase.

5. The host cell of claim 3 wherein the first DNA sequence codes for the alpha subunit of *Klebsiella pneumoniae* oxalacetate decarboxylase, or fragments thereof that allow for post-translation biotination of the fusion protein.

6. The host cell of claim 5 wherein the first DNA sequence codes for the potion of the alpha subunit of *Klebsiella pneumoniae* oxalacetate decarboxylase having the following amino acid sequence:

DVSQLTAAAPAPAPAPAPASAPAAAAPAGAGTPVTAPLAGFIWKVLASEGQTVAA
GEVLLILEAMKMETEIRAAQAGTVRGIAVKAGDAVAVGDTLMTLA.

7. A method of producing a fusion protein comprising culturing the transformed host cell of any one of claims 1–6 under conditions permitting expression of the fusion protein and the biotin ligase and permitting biotination of the fusion protein.

8. The host cell of any one of claims 1–6 wherein the DNA coding for the fusion protein further comprises an additional DNA sequence which codes for a signal or signal-leader peptide, or fragment thereof, the additional DNA sequence being located upstream of the first and second DNA sequences and being operatively linked to them so as to provide for secretion of the fusion protein.

9. A method of producing a fusion protein comprising culturing the transformed host cell of claim 8 under conditions permitting expression of the fusion protein and the biotin ligase and permitting biotination of the fusion protein.

* * * * *

UNITED STATES PATENT AND TRADEMARK OFFICE
CERTIFICATE OF CORRECTION

PATENT NO. : 5,252,466
DATED : October 12, 1993
INVENTOR(S) : John E. Cronan, Jr.

Page 1 of 3

It is certified that error appears in the above-indentified patent and that said Letters Patent is hereby corrected as shown below:

On the title page, item [56]:
IN THE REFERENCES CITED

On page 2, column 1, under "OTHER PUBLICATIONS", on line 21, for Barker and Campbell, delete "4679" and substitute therefor --469--.

On page 2, column 2, under "OTHER PUBLICATIONS", on line 10, for Green, delete "85-113" and substitute therefor --85-133--.

On page 3, column 2, under "OTHER PUBLICATIONS", on line 5, for Swack et al., delete "115" and substitute therefor --114--.

In column 3, line 24, delete "(PS 3S)" and substitute therefor --(PS 1.3S)--.

In column 10, line 56, delete "promotor" and substitute therefor --promoter--.

In column 11, line 17, after "derivatives", delete "of".

In column 12, line 55, delete "Sacchromyces" and substitute therefor --Saccharomyces--.

UNITED STATES PATENT AND TRADEMARK OFFICE
CERTIFICATE OF CORRECTION

PATENT NO. : 5,252,466
DATED : October 12, 1993
INVENTOR(S) : John E. Cronan, Jr.

It is certified that error appears in the above-indentified patent and that said Letters Patent is hereby corrected as shown below:

In column 12, line 67, delete "catalyses" and substitute therefor --catalyzes--.

In column 19, line 21, delete "Pistcataway" and substitute therefor --Piscataway--.

In column 20, line 27, delete "Pistcataway" and substitute therefor --Piscataway--.

In column 26, line 16, delete "anlogous" and substitute therefor --analogous--.

In column 31, line 63, delete "from obtained" and substitute therefor --obtained from--.

In column 32, line 30, delete "pLSI" and substitute therefor --pLS1--.

In column 33, line 49, delete "promotor" and substitute therefor --promoter--.

In column 33, line 56, delete "promotor" and substitute therefor --promoter--.

In column 34, line 16, delete "promotor" and substitute therefor --promoter--.

In column 38, line 17, after "lacZ", delete "." and substitute therefor --,--.

UNITED STATES PATENT AND TRADEMARK OFFICE
CERTIFICATE OF CORRECTION

PATENT NO. : 5,252,466
DATED : October 12, 1993
INVENTOR(S) : John E. Cronan, Jr.

It is certified that error appears in the above-indentified patent and that said Letters Patent is hereby corrected as shown below:

In column 38, lines 52-53, delete "beta-lactamose" and substitute therefor --beta-lactamase--.

In column 38, line 59, delete "pLSI" and substitute therefor --pLS1--.

In column 39, line 32, delete "Kan®" and substitute therefor --Kan$^r$--.

In column 39, line 67, delete "medical" and substitute therefor --Medical--.

Column 41:
In claim 3, line 34, delete "11" and substitute therefor --1--,

Signed and Sealed this

Eleventh Day of October, 1994

Attest:

BRUCE LEHMAN

Attesting Officer    Commissioner of Patents and Trademarks